United States Patent
Modak et al.

(10) Patent No.: US 11,033,654 B2
(45) Date of Patent: *Jun. 15, 2021

(54) METHODS AND COMPOSITIONS FOR ACHIEVING HEMOSTASIS AND STABLE BLOOD CLOT FORMATION

(71) Applicant: Endomedix, Inc., Montclair, NJ (US)

(72) Inventors: Piyush Modak, Kearny, NJ (US);
Malavika Nadig, Harrison, NJ (US);
Richard Russo, Morristown, NJ (US)

(73) Assignee: Endomedix, Inc., Montclaire, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/697,717

(22) Filed: Nov. 27, 2019

(65) Prior Publication Data

US 2020/0353121 A1    Nov. 12, 2020

Related U.S. Application Data

(63) Continuation of application No. 16/194,917, filed on Nov. 19, 2018, now Pat. No. 10,517,988.

(51) Int. Cl.
| | | |
|---|---|---|
| *A61L 24/00* | (2006.01) | |
| *A61L 24/04* | (2006.01) | |
| *A61L 24/08* | (2006.01) | |
| *C08B 37/02* | (2006.01) | |
| *C08B 37/08* | (2006.01) | |

(52) U.S. Cl.
CPC ............ *A61L 24/08* (2013.01); *A61L 24/0005* (2013.01); *A61L 24/0015* (2013.01); *A61L 24/0031* (2013.01); *A61L 24/0036* (2013.01); *A61L 24/043* (2013.01); *C08B 37/003* (2013.01); *C08B 37/0021* (2013.01); *A61L 2400/04* (2013.01)

(58) Field of Classification Search
CPC .. A61L 24/08; A61L 24/0005; A61L 24/0015; A61L 24/043; A61L 24/0036; A61L 2400/04; C08B 37/0021; C08B 37/003
See application file for complete search history.

(56) References Cited

U.S. PATENT DOCUMENTS

| | | |
|---|---|---|
| 3,879,376 A | 4/1975 | Vanlerberghe et al. |
| 3,953,608 A | 4/1976 | Vanlerberghe et al. |
| 4,394,373 A | 7/1983 | Malette et al. |
| 4,454,110 A | 6/1984 | Caslaysky et al. |
| 4,528,283 A | 7/1985 | Lang et al. |
| 4,532,134 A | 7/1985 | Malette et al. |
| 4,619,995 A | 10/1986 | Hayes |
| 4,822,598 A | 4/1989 | Lang et al. |
| 4,902,281 A | 2/1990 | Avoy |
| 4,996,307 A | 2/1991 | Itoi et al. |
| 5,093,319 A | 3/1992 | Higham et al. |
| 5,607,918 A | 3/1997 | Eriksson et al. |
| 5,888,988 A | 3/1999 | Elson |
| 6,162,241 A | 12/2000 | Coury et al. |
| 6,165,488 A | 12/2000 | Tardy et al. |
| 6,166,130 A | 12/2000 | Rhee et al. |
| 6,458,889 B1 | 10/2002 | Trollsas et al. |
| 6,458,938 B1 | 10/2002 | Cha et al. |
| 6,503,527 B1 | 1/2003 | Whitmore et al. |
| 6,534,591 B2 | 3/2003 | Rhee et al. |
| 6,602,952 B1 | 8/2003 | Bentley et al. |
| 6,616,869 B2 | 9/2003 | Mathiowitz et al. |
| 6,699,484 B2 | 3/2004 | Whitmore et al. |
| 6,730,735 B2 | 5/2004 | Davis et al. |
| 6,773,723 B1 | 8/2004 | Spiro et al. |
| 6,806,260 B1 | 10/2004 | Hirofumi et al. |
| 6,818,018 B1 | 11/2004 | Sawhney |
| 6,833,408 B2 | 12/2004 | Sehl et al. |
| 6,884,788 B2 | 4/2005 | Bulpitt et al. |
| 6,896,904 B2 | 5/2005 | Spiro et al. |
| 6,899,889 B1 | 5/2005 | Hnojewyj et al. |
| 6,921,532 B1 | 7/2005 | Austin et al. |

(Continued)

FOREIGN PATENT DOCUMENTS

| | | |
|---|---|---|
| EP | 1462123 A1 | 9/2004 |
| EP | 1555035 A2 | 7/2005 |

(Continued)

OTHER PUBLICATIONS

U.S. Appl. No. 11/379,182, Restriction Requirement dated Aug. 6, 2008, 8 pgs.
U.S. Appl. No. 11/379,182, Restriction Requirement dated Oct. 2, 2007, 7 pgs.
U.S. Appl. No. 11/379,182, Final Office Action dated Aug. 21, 2009, 17 pgs.
U.S. Appl. No. 11/379,182, Response filed May 18, 2009 to Non Final Office Action dated Dec. 12, 2008, 26 pgs.
U.S. Appl. No. 11/425,280, Response filed Nov. 6, 2008 to Restriction Requirement dated Oct. 30, 2008, 7 pgs.
U.S. Appl. No. 11/425,280 Non-Final Office Action dated Jan. 23, 2009, 31 pgs.

(Continued)

*Primary Examiner* — Alma Pipic
(74) *Attorney, Agent, or Firm* — Goodwin Procter LLP

(57) ABSTRACT

Provided is tunable biopolymer hydrogel produced from two processed natural polysaccharides for use as a hemostat. If desired, the hydrogel formation can be tuned so that the hydrogel forms within seconds when applied to a tissue lesion. The resulting hydrogel can adhere to tissue and, without swelling, produce hemostasis within seconds after application to tissue of interest. The hydrogel also captures, aggregates and concentrates platelets and red blood cells at the site of the tissue lesion thereby initiating a clotting cascade at the site of the lesion. The hemostat can be used to prevent blood loss during surgical procedures, for example, during brain, spine or other surgical procedures where hemostasis is desirable, and is particularly useful during surgical procedures where swelling of the hemostat (e.g., in the brain or spine) would be detrimental to the subject.

32 Claims, 8 Drawing Sheets

(56) References Cited

U.S. PATENT DOCUMENTS

| | | | |
|---|---|---|---|
| 6,936,276 B2 | 8/2005 | Spiro et al. |
| 6,939,562 B2 | 9/2005 | Spiro et al. |
| 7,053,068 B2 | 5/2006 | Prinz |
| 7,115,588 B2 | 10/2006 | Vournakis et al. |
| 7,456,267 B2 | 11/2008 | Elson et al. |
| 7,854,923 B2 * | 12/2010 | Chen |
| 8,513,217 B2 | 8/2013 | Chen et al. |
| 9,198,997 B2 | 12/2015 | Myntti et al. |
| 9,259,434 B2 | 2/2016 | Chen et al. |
| 9,364,578 B2 | 6/2016 | Zhu et al. |
| 9,433,636 B2 | 9/2016 | Tijsma et al. |
| 9,731,044 B2 | 8/2017 | Chen et al. |
| 9,801,812 B1 | 10/2017 | Girdhar et al. |
| 9,846,163 B2 | 12/2017 | McGrath et al. |
| 9,855,372 B2 | 1/2018 | Ladet |
| 9,861,701 B2 | 1/2018 | Sershen et al. |
| 10,517,988 B1 * | 12/2019 | Modak |
| 2002/0082215 A1 | 6/2002 | Frey |
| 2003/0078234 A1 | 4/2003 | Vournakis et al. |
| 2004/0052850 A1 | 3/2004 | Schankereli |
| 2004/0091540 A1 | 5/2004 | Desrosiers et al. |
| 2004/0156904 A1 | 8/2004 | Saltman et al. |
| 2004/0166158 A1 | 8/2004 | Davis et al. |
| 2004/0228794 A1 | 11/2004 | Weller et al. |
| 2004/0229784 A1 | 11/2004 | Vesely |
| 2004/0258727 A1 | 12/2004 | Liu et al. |
| 2004/0258747 A1 | 12/2004 | Ponzoni et al. |
| 2005/0002893 A1 | 1/2005 | Goldmann |
| 2005/0186243 A1 | 8/2005 | Hunter et al. |
| 2005/0214255 A1 | 9/2005 | Elson et al. |
| 2005/0226938 A1 | 10/2005 | Borbely et al. |
| 2005/0238702 A1 | 10/2005 | Ishihara et al. |
| 2005/0271729 A1 | 12/2005 | Wang |
| 2005/0281880 A1 | 12/2005 | Wang |
| 2006/0014861 A1 | 1/2006 | Geesey et al. |
| 2006/0029571 A1 | 2/2006 | Karageozian et al. |
| 2006/0159733 A1 | 7/2006 | Pendharkar et al. |
| 2007/0003525 A1 | 1/2007 | Moehlenbruck et al. |
| 2007/0031467 A1 | 2/2007 | Abrahams et al. |
| 2007/0031468 A1 | 2/2007 | Abrahams et al. |
| 2007/0243130 A1 | 10/2007 | Chen et al. |
| 2008/0063617 A1 | 3/2008 | Abrahams et al. |
| 2008/0075657 A1 | 3/2008 | Abrahams et al. |
| 2008/0124395 A1 | 5/2008 | Chen et al. |
| 2009/0010982 A1 | 1/2009 | Abrahams et al. |
| 2011/0311632 A1 | 12/2011 | Roorda et al. |
| 2014/0005375 A1 | 1/2014 | Tramontano et al. |
| 2014/0274944 A1 | 9/2014 | Ohri et al. |
| 2014/0336147 A1 | 11/2014 | Berman et al. |
| 2016/0058904 A1 | 3/2016 | Kirsch et al. |
| 2016/0206773 A1 | 7/2016 | Mousa et al. |
| 2017/0100427 A1 | 4/2017 | Medina et al. |
| 2017/0106118 A1 | 4/2017 | Ladet et al. |
| 2017/0189573 A1 | 7/2017 | Rubin et al. |
| 2017/0224868 A1 | 8/2017 | Bristow et al. |
| 2017/0246113 A1 | 8/2017 | Blaskovich et al. |
| 2017/0258954 A1 | 9/2017 | Conrad et al. |
| 2017/0258967 A1 | 9/2017 | Haggard et al. |
| 2017/0304487 A1 | 10/2017 | Hissong et al. |

FOREIGN PATENT DOCUMENTS

| | | |
|---|---|---|
| EP | 1704225 A2 | 9/2006 |
| EP | 1837041 A1 | 9/2007 |
| EP | 2101830 A1 | 9/2009 |
| EP | 2920240 A2 | 9/2015 |
| EP | 3003412 A1 | 4/2016 |
| EP | 3281646 A1 | 2/2018 |
| WO | WO-2001097872 | 12/2001 |
| WO | WO-2003035122 | 5/2003 |
| WO | WO-2004006961 A1 | 1/2004 |
| WO | WO-2004096152 | 11/2004 |
| WO | WO-2005113608 | 12/2005 |
| WO | WO-2006013337 A1 | 2/2006 |
| WO | WO-2007027849 A1 | 3/2007 |
| WO | WO-2007124198 A2 | 11/2007 |
| WO | WO-2007149130 A1 | 12/2007 |
| WO | WO-2009017753 A2 | 2/2009 |
| WO | WO-2010070458 A2 | 6/2010 |
| WO | WO-2014191739 A1 | 12/2014 |
| WO | WO-2016164903 A1 | 10/2016 |
| WO | WO-2016178829 A1 | 11/2016 |
| WO | WO-2016200886 A1 | 12/2016 |
| WO | WO-2016209198 A1 | 12/2016 |
| WO | WO-2018005145 A1 | 1/2018 |
| WO | WO-2020106703 A1 | 5/2020 |

OTHER PUBLICATIONS

U.S. Appl. No. 11/425,280, Preliminary Amendment dated Feb. 19, 2007, 13 pgs.

U.S. Appl. No. 11/425,280, Response filed Jul. 16, 2008 to Restriction Requirement dated Jun. 24, 2008, 7 pgs.

U.S. Appl. No. 11/425,280, Restriction Requirement dated Jun. 24, 2008, 10 pgs.

U.S. Appl. No. 11/425,280, Restriction Requirement dated Oct. 30, 2008, 6 pgs.

U.S. Appl. No. 11/425,958, Non-Final Office Action dated Mar. 11, 2009, OARN, 33 pgs.

U.S. Appl. No. 11/447,794, Non-Final Office Action dated Jan. 8, 2009, 14 pgs.

U.S. Appl. No. 11/447,794, Non-Final Office Action dated Jul. 22, 2008, 12 pgs.

U.S. Appl. No. 11/447,794, Response filed Apr. 9, 2008 to Restriction Requirement dated Mar. 19, 2008, 7 pgs.

U.S. Appl. No. 11/447,794, Response filed Sep. 22, 2008 to Non-Final Office Action dated Jul. 22, 2008, 12 pgs.

U.S. Appl. No. 11/447,794, Restriction Requirement dated Mar. 19, 2008, 8 pgs.

U.S. Appl. No. 11/530,362, Non-Final Office Action dated Dec. 19, 2008, 22 pgs.

U.S. Appl. No. 11/530,362, Preliminary Amendment dated Feb. 19, 2007, 13 pgs.

U.S. Appl. No. 11/530,362, Response file Sep. 22, 2008 to Restriction requirement dated Sep. 4, 2008, 15 pgs.

U.S. Appl. No. 11/530,362, Restriction Requirement dated Sep. 4, 2008, 12 pgs.

Freier, T., et al., "Controlling Cell Adhesion and Degradation of Chitosan Films by N-Acetylation," *Biomatenals*, 2005, vol. 26, pp. 5872-5878.

Moisturizer, http://en.wikipedia.org/wiki/Moisturizer, (2006), 2 pgs.

Sezer, A. D., et al., "Release Characteristic of Chitosan Treated Alginate Beads: II. Sustained Release of a Low Molecular Drug from Chitosan Treated Alginate Beads," *J Microencapsul.*, 1999, vol. 16(6), pp. 687-696.

Abrahams, J. M., et al., "Delivery of Human Vascular Endothelial Growth Factor with Platinum Coil Enhances Wall Thickening and Coil Impregnation in a Rat Aneursym Model," *Am. J. Neuroradiol.*, 2001, 22, pp. 1410-1417.

Agnihotri, et al., "Degradation of Chitosan and Chemically Modified Chitosan by Viscosity Measurements," Journal of Applied Polymer Science, (2006), vol. 102, No. 4, pp. 3255-3258.

Aiba, "Studies on chitosan: 4. Lysozymic hydrolysis of partially N-acetylated chitosans," Int J Biol Macromol, (1992), vol. 14, No. 4, pp. 225-228.

Aiba, Sei-ichi, et al., "Application of Chitin and Chitosan to Functional Materials; Organo-and Water-Soluble Chitosan Derivatives and N-Acetyl-D-Glucosamine," *National Institute of Advanced Industrial Science and Technology (AIST)*, Ikeda, Osaka Japan, 2004, 2 pgs.

Amano, et al., "The Action of Lysozyme on Partially Deacetylated Chitin," European Journal of Biochemistry, (1978), vol. 85, pp. 97-104.

U.S. Appl. No. 11/379,182, Non-Final Office Action dated Dec. 12, 2008, 12 pgs.

U.S. Appl. No. 11/379,182, Non-Final Office Action dated Dec. 21, 2007, OARN, 10 pgs.

(56) References Cited

OTHER PUBLICATIONS

U.S. Appl. No. 11/379,182, Response filed Aug. 22, 2008 to Restriction Requirement dated Aug. 6, 2008, 18 pgs.
U.S. Appl. No. 11/379,182, Response filed Nov. 1, 2007 to Restriction Requirement dated Oct. 2, 2007, 12 pgs.
U.S. Appl. No. 11/379,182, Response to Non-Final Office Action filed Apr. 9, 2008, 19 pgs.
U.S. Appl. No. 11/530,362, Final Office Action dated Jul. 30, 2009, 15 pgs.
U.S. Appl. No. 11/530,362, Response filed May 18, 2009 to Final Office Action dated Dec. 9, 2008, 20 pgs.
Athanasiadis, Theo, et al., "Effects of a Novel Chitosan Gel on Mucosal Wound Healing Following Endoscopic Sinus Surgery in a Sheep Model of Chronic Rhinosinusitis," *The Laryngoscope*, 2008, vol. 118, pp. 1088-1094.
Bartkowiak, et al., "Alginate-Oligochitosan Microcapsules: A Mechanistic Study Relating Membrane and Capsule Properties to Reaction Conditions," Chemistry of Materials, 1999, vol. 11, No. 9, pp. 2486-2492.
Borzacchiello, A., et al., "Chitosan-Based Hydrogels: Synthesis and Characterization," Journal of Materials Science, 2001, vol. 12, pp. 861-864.
Cabral, et al., "Synthesis, physiochemical characterization, and biocompatibility of a chitosan/dextran-based hydrogel for postsurgical adhesion prevention," Journal of Materials Science Materials in Medicine, (Aug. 2014), vol. 25, pp. 2743-2756.
Campbell, Patrick K., et al., "Evaluation of Absorable Surgical Sealants: In vitro Testing," www.duralsealant.com/duralsealant/literature.htm, 2005, 4 pgs.
Cargioli, Theresa G., et al., http://www.sinc.sunysb.edu/Stu/tcargiol/Research.htm, 2006, 3 pgs.
Chenite, A., et al., "Novel Injectable Neutral Solutions of Chitosan form Biodegradable Gels in Situ," Biomaterials, 2000, 21, pp. 2155-2161.
Cordes, et al., "On the Mechanism of Schiff Base Fromation and Hydrolysis," Journal of the American Chemical Society, (1962), vol. 84, No. 5, pp. 832-837.
Crescenzi, V., et al., "New Hydrogels Based on Carbohydrate and on Carbohydrate-Synthetic Polymer Networks," *Polymer Gels and Networks*, 1997, vol. 5, pp. 225-239.
Di Martino, A. et al., "Chitosan: A Versatile Biopolymer for Orthopaedic Tissue-Engineering," *Biomaterials*, 2005, vol. 26, No. 30, pp. 5983-5990.
DuraSseal Sealant Systems, http://www.confluentsurgical.com/prodds ous.html, (2006), 2 pgs.
Ellis-Behnke, et al., "Nano hemostat solution: immediate hemostasis at the nanoscale," Nanomedicine Nanotechnology, Bio, and medicine 2, (2006), pp. 207-215.
Freier, T. et al., "Controlling Cell Adhesion and Degradation of Chitosan Films by N-Acetylation," *Biomaterials*, 2005, vol. 26, pp. 5872-5878.
Gray, "The World of Skin Care," http://www.pg.com/science/skincare/Skin_tws_102.htm, (1997), 2 pgs.
Grotenhuis, J. A., et al., "A Novel Absorbable Hydrogel for Dural Repair: Results of a Pilot Clinical Study," Confluent Surgical, http://confluentsurgical.com/pdf/ds/DuraSeal_Pilot-Study-WP4-7-05.pdf, 2005, 4 pgs.
Hennink, W. E., et al., "Novel Crosslinking Methods to Design Hydrogels," Adv. Drug Deliv. Rev., 2002, vol. 54(1), pp. 13-36.
Heras et al. "N-Methylene Phosphonic Chitosan: a Novel Soluble Derivative," Carbohydrate Polymers, 2001, vol. 44, pp. 1-8.
Hirano, et al., "Chitin biodegradation in sand dunes," Biochemical Systematics and Ecology, 1991, vol. 19, No. 5, pp. 379-384.
Hollander, Anthony P., et al., "Chapters 3 & 4," *Biopolymer Methods in Tissue Engineering*/edited by Anthony P. Hollander and Paul V. Hatton, Totowa, N. J.: Humana Press, 2004, pp. 24-48.
Holme, et al. "Chitosan N-Sulfate. A Water-Soluble Polyelectrolyte," Carbohydrate Research, 1997, vol. 302, pp. 7-12.
Holme, et al., "Thermal depolymerization of chitosan chloride," Carbohydrate Polymers, (2001), vol. 46, pp. 287-294.

International Application No. PCT/US2007/001606, Demand and Article 34 Amendment filed Apr. 10, 2008, 24 pgs.
International Application No. PCT/US2007/001606, International Search Report dated Oct. 23, 2007, 4 pgs.
International Application No. PCT/US2007/001606, Written Opinion dated Oct. 23, 2007, 7 pgs.
International Application No. PCT/US2007/062393, Preliminary Report on Patentability dated Oct. 30, 2008, 8 pgs.
International Application No. PCT/US2007/062393, Search Report dated Aug. 19, 2008, 4 pgs.
International Application No. PCT/US2007/062393, Written Opinion dated Aug. 19, 2008, 5 pgs.
International Application No. PCT/US2008/007234, International Search Report dated Apr. 2, 2009.
International Application No. PCT/US2008/007234, Written Opinion dated Apr. 2, 2009.
International Application No. PCT/US2008/009198, International Search Report dated Apr. 9, 2009.
International Application No. PCT/US2008/009198, Written Opinion dated Apr. 9, 2009.
International Application No. PCT/US2019/062192, International Search Report dated Feb. 20, 2020, 7 pgs.
International Application No. PCT/US2019/062192, Written Opinion dated Feb. 20, 2020, 6 pgs.
Ishak, et al., "Kinetic Evidence for Hemiacetal formation during the oxidation of Dextran in Aqueous Periodated," Carbohydrate Research, (1978), vol. 64, pp. 189-197.
Jayakumar et al. "Sulfated Chitin and Chitosan as Novel Niomaterials," *International Journal of Biological Macromolecules*, 2007, vol. 40, pp. 175-181.
Jia et al. "Synthesis and Antibacterial Activities of Quaternary Ammonium Salt of Chitosan," *Carbohydrate Research*, 2001, vol. 333, pp. 1-6.
Jiang, et al., "Biodegrabable Hyaluronic Acid/N-Carboxyethyl Chitosan/Protean Ternary Complexes as Implantable Carriers for Controlled Protein Release," Macromolecular Bioscience, (2005), vol. 5, No. 12, pp. 1226-1233.
Jiang, H. et al. "Chitosan-Based Hydrogels: A New Polymer-Based System with Excellent Laser-Damage Threshold Properties" *Journal of Polymer Science: Part B: Polymer Physics*, 1999, vol. 37, pp. 769-778.
Kang, Q. K., et al., "Arterial Embolization Using Poly-N-Acetyl Glucosamine Gel in a Rat Kidney Model," *The Anatomical Record Part A, 2005, 284A*, pp. 454-459.
Kato et al. "N-Succinyl-Chitosan as a Drug Carrier: Water-Insoluble and Water-Soluble Conjugates," Biomaterials, 2004, vol. 25, pp. 907-915.
Kean, et al., "Biodegratation, distribution and toxicity of chitosan," Advanced Drug Delivery Reviews, (2010), vol. 62, pp. 3-11.
Kohn, "Biomaterials science: an introduction ro materials in medicine," San Diego: Academic Press, (1996), pp. 64-73.
Kohn, et al., "Metabolism of D-Glucoseamine and N-Acetyl-D-glucosamine in the Intact Rat," Journal of Biological Chemistry, (1962), vol. 237, No. 2, pp. 304-308.
Kramer, B. S., et al., "Grappling with Cancer Defeatisim Versus the Reality of Progress," N Eng J Med, 1997, 337, pp. 931-935.
Leach, Jennie B., et al., "Photocrosslinked Hyaluronic Acid Hydrogels: Natural, Biodegradable Tissue Engineering Scaffolds," *Biotechnology and Bioengineering*, 2003, vol. 82, No. 5, pp. 578-589.
Lim, et al., "In vitro and in vivo degradation behavior of acetylated chitosan porous beads," Journal of Biomaterial Science Polymer Edition, (2008), vol. 19, No. 4, pp. 453-466.
Ma, et al., "Preparation and Characterization of N-alkylated Chitosan Derivatives," J. Appli. Polym. Sci. 2008, vol. 109, pp. 1093-1098.
Maia, et al. "Insight on the periodate oxidation of dextran and its structural vicissitudes," Polymer, (2011), vol. 52, pp. 258-265.
Maia, et al., "Synthesis and characterization of a new injectable and degradable dextran-based hydrogels," Polymer, (2005), vol. 46, pp. 9604-9614.
Material Safety Data Sheet: Acetic Acid 10% v/v Aqueous Solution. 2006.
Material Safety Data Sheet: Acetic Anhydride.2006.

(56) References Cited

OTHER PUBLICATIONS

Material Safety Data Sheet: Methyl Alcohol, Reagent ACS, 99.8% (GC). 2001.
Material Safety Data Sheet: N, N'-Methylenebisacrylamide. 2008.
Moisturizer, http://en.wikipedia.orq/wiki/Moisturizer, (2006), 2 pgs.
Mwale, F., et al., "Biological Evaluation of Chitosan Salts Cross-Linked to Genpin as a Cell Scaffold for Disk Tissue Engineering," *Tissue Engineering*, 2005, vol. 11, No. 1-2, pp. 130-140.
Onishi, et al., "Biodegradation and distribution of water-soluble chitosan in mice," Biomaterials, (1999), vol. 20, pp. 175-182.
Park, et al., "Biomaterials an Introduction," 3rd ed., New York: Springer, (2007), pp. 485-515.
Polyethylene Glycol and Derivatives for Advanced PEGylation, 2005, Catalog 2005-2006 Nektar Advanced PEGylation, www.nektar.com/pdf/nektar_catalog.pdt, 34 pgs.
Profeta, et al., "Endoscope-Assisted Microneurosurgery for Anterior Circulation Aneurysms Using the Angle-Type Rigid Endoscope Over a 3-Year Period," *Child Nerv. Syst.*, 2004, vol. 20 (No. 11-12), pp. 811-815.
Ratner, et al., "An Introduction to Materials in Medicine," Biomaterials Science, (1996), pp. 64- 73.
Ren, et al., "The enzymatic degradation and swelling properties of chitosan matrices with different degrees of N-acetylation," Carbohydrate Research, (2005), vol. 340, pp. 2403-2410.
Ribourtout, E., et al., "Gene Therapy and Endovascular Treatment of Intracranial Aneurysms," *Stroke*, 2004, vol. 35, pp. 786-793.
Riha, G. M., et al., "Application of Stem Cells for Vascular Tissue Engineering," *Tissue Engineering*, 2005, vol. 11 (No. 9-10), pp. 1535-1552.
Sanzgiri, et al., "Synthesis, characterization, and in vitro stability of chitosan-methotrexate conjugates," Pharm. Res., 1990, vol. 7, No. 4, pp. 418-421.
Sashiwa, et al., "Chemical Modification of Chitosan, 17a Michael Reaction of Chitosan with Acrylic Acid in Water," Macromolecular Bioscience, (2003), vol. 3, No. 5, pp. 231-233.
Sashiwa, H., et al., "Chemical Modification of Chitosan, 17," Macromol Biosci., 2003, vol. 3, pp. 231-233.
Sashiwa, H., et al., "Michael Reaction of Chitosan with Various Acryl Reagents in Water," *Biomacromolecules*, 2003, vol. 4(5), pp. 1250-1254.
Schiele, U., et al., "Haemostyptic Preparations on the Basis of Collagen Alone and as Fixed Cominbation with Fibrin Glue," *Clinical Materials, Elsevier*, 1992, vol. 9, No. 3-4, pp. 169-177.
Setnikar, et al., Absorption, distribution, metabolism and excretion of glucosamine sulfate, A Review, (abstract only), Arzneimittelforschung, (2001), vol. 51, No. 9, pp. 699-725.
Sezer, A. D., et al., "Release Characteristics of Chitosan Treated Alginate Beads: II. Sustained Release of a Low Molecular Drug from Chitosan Treated Alginate Beads," *J Microencapsul.*, 1999, vol. 16(6), pp. 687-696.
Shu, X. Z., et al., "Disulfide-Crosslinked Hyaluronan-Gelatin Hydrogel Films: a Covalent Mimic of the Extracellular Matrix for in Vitro Cell Growth", *Biomaterials*, 2003, vol. 24, pp. 3825-3834.
Spotnitz, W. D., et al., "Fibrin Glue from Stored Human Plasma: An Inexpensive and Efficient Method for Local Blood Bank Preparation," *The American Surgeon*, 1987, vol. 53, pp. 460-462.
Sugimoto et al. "Preparation and Characterization of Water-Soluble Chitin and Chitosan Derivatives," *Carhydrate Polymers*, 1998, vol. 36, pp. 49-59.
Suh, et al., "Application of chitosan-based polysaccharide biomaterials in cartilage tissue engineering: A review," Biomaterials, (2000), vol. 21, No. 24, pp. 2589-2598.
Tan, et al., "Gelatin/chitosan/hyaluronan ternary complex scaffold containing basic fibroblast growth factor for cartilage tissue engineering," Journal of Material Science: Materials in Medicine, (2007), vol. 18, No. 10, pp. 1961-1968.
Tan, et al., "Injectable in situ forming biodegradable chitosan-hyaluronic acid based hydrogels for cartilage tissue engineering," Biomaterials, (2009), vol. 30, pp. 2499-2506.
Tomihata, et al., In vitro and in tivo degradation of films of chitin and its deacetylated derivatives, Biomaterials, (1997), vol. 18, No. 7, pp. 567-575.
Varum, et al., "Acid hydrolysis of chitosans," Carbohydrate Polymers, (2001), vol. 46, pp. 89-98.
Varum, et al., "Determination of the degree of N-acetylation and the distribution of N-acetyl groups in partially N-deacetylated chitins (chitosans) by high-field n.m.r. spectroscopy," Carbohydrate Research, (1991), vol. 211, No. 1, pp. 17-23.
Varum, et al., "In vitro degradation rates of partially N-acetylated chitosan in human serum," Carbohydrate Research, (1997), vol. 299, pp. 99-101.
Verheul, et al., "Influence of the degree of acetylation on the enzyme degradation and in vitro biological properties of trimethylated chitosans," Biomaterials, (2009), vol. 30, No. 18, pp. 3129-3135.
Wu, et al., "Enzymatically degradable oxidized dextran-chitosan hydrogels with an anisotropic aligned porous structure," Soft Mater, (2013); vol. 9, No. 46, pp. 11136-11142.
Xie et al. "Preparation and Antibacterial Activity of a Water-Soluble Chitosan Derivative," *Carbohydrate Polymers*, 2002, vol. 50, pp. 35-40.
Xu et al. "Preparation and Modification of N-(2-hydroxyl) Propyl-3-Trimethyl Ammonium Chitosan Chloride Nanoparticle as a Protein Carrier," *Biomaterials*, 2003, vol. 24, pp. 5015-5022.
Yang et al. "Adsorption of Metal Cations by Water-Soluble N-Alkylated Disaccharide Chitosan Derivatives," *Journal of Applied Polymer Science*, 2005, vol. 98, pp. 564-570.
Yang, et al. "The controlling biodegradation of chitosan fibers by N-acetylation in vitro and in vivo," Journal of Material Science: Materials in Medicine, (2007), vol. 18, pp. 2117-2121.
Yu, et al., "Novel oxidation of methyl glycopyranosides by periodic acid in dimethyl sulfoxide," Canadian Journal of Chemistry, (1967), vol. 45, pp. 2195-2203.
Yuan et al. "Self Healing in Polymers and Polymer Composites. Concepts, Realization and Outlook: A Review," *xPRESS Polymer Letters*, 2008, vol. 2(4), pp. 238-250.

\* cited by examiner

METHODS AND COMPOSITIONS FOR ACHIEVING HEMOSTASIS AND STABLE BLOOD CLOT FORMATION

RELATED APPLICATIONS

This application is a continuation of U.S. patent application Ser. No. 16/194,917, filed Nov. 19, 2018, the entire disclosure of which is incorporated herein by reference for all purposes.

FIELD

The invention relates generally to methods and compositions for achieving hemostasis and blood coagulation, and more specifically relates to methods and compositions for achieving hemostasis and blood coagulation during surgical procedures.

BACKGROUND

Bleeding and blood loss are problems that must be addressed during and at the conclusion of surgery and other medical procedures. Significant blood loss can be fatal or cause significant morbidity, and surgeons and medical staff routinely compensate for blood loss with transfusions and the use of recirculating devices. A number of different techniques and products are currently used by surgeons to stop bleeding and effect hemostasis in surgery and medical procedures. However no single approach is effective or suitable under all circumstances, and the currently available approaches have limitations in effectiveness, safety, applicability and ease of use.

The most commonly used approaches involve closing a tissue or blood vessel mechanically with a suture or staple. This ligature technique is often effective, though it may allow for minor bleeding to occur around suture or staple holes. Sometimes biological or synthetic adhesives are applied to either complement or replace sutures or staples to stop this blood flow. However, tissue sealants are not hemostats per se and allow the pooling of blood underneath the seal in cases of moderate bleeding that may result in the formation of a hematoma. Hemostatic products which require time-consuming application or which produce slow effective action can be costly both in terms of financial costs due to greater operating room time and in terms of post procedure patient morbidity. Some techniques and products have limited effectiveness in certain applications, which may require a surgeon to reapply the product or switch to another product, which can be both time consuming and costly.

Under certain circumstances standard ligature techniques are inappropriate or not feasible. In such cases, an absorbable hemostatic product can be applied to the bleeding surface with a goal of achieving hemostasis that will later lead to a durable clot formation. Passive hemostats can control bleeding through absorption and may be powders, gauze, sponges or cross-linked gelatin. Sometimes these are augmented with an active hemostatic agent such as thrombin to try to achieve a successful hemostasis. However, the efficacy of these products is often variable and their use has been associated with adverse effects which can provide significant challenges during a surgical procedure. Such challenges become especially pronounced in certain surgical procedures such as brain and spinal surgeries. For example, certain sponges derived from porcine material can absorb up to 45-times their weight in blood and fluids resulting in significant swelling of the product that can lead to a patient experiencing adverse reactions such as pain, paresis or paralysis that can require revision surgery to address. Certain particulate hemostats have been reported to have caused cerebral edema. Gelatin-based devices typically swell during use and have been reported to cause mass effects leading to the development and progression of hemiparesis that required revision surgery to address the situation. Other adverse events and complications have been reported for all these types of hemostats. Most of these devices rely on absorption of blood and body fluids to produce hemostasis, which results in swelling and can lead to the reported mass effects.

The slow action of available absorbable hemostats, which are often used multiple times per case, can add to the length of surgical procedures, adding to expense and post-operative morbidity. Certain commercially available hemostats require as much as 10 minutes to produce hemostasis for each incidence of bleeding during a surgical procedure.

Accordingly, there remains a need for a fast acting, ready to use, biocompatible, biodegradable hemostat that minimizes or prevents bleeding and blood loss, does not swell during use and promotes stable clot formation during a wide variety of surgical procedures including cranial and spinal surgeries and in minimally invasive surgical procedures, and significantly reduces the incidence of postoperative adverse events.

SUMMARY OF THE INVENTION

The invention is based upon the discovery that it is possible to create a fast acting biocompatible hemostat that, promotes coagulation, produces hemostasis, does not swell during use, is adherent and does not migrate away from a site of application, is transparent, and is biodegradable.

The invention provides a "tunable" biopolymer system that addresses heretofore unmet needs in the field of hemostasis. In this system, two processed natural polysaccharides in the form of separate solutions are simultaneously mixed and applied onto a bleeding site, where they form a hydrogel device in situ. The hydrogel can form and produces hemostasis within seconds after application. The system may also be designed or "tuned" to produce hydrogels and facilitate hemostasis more slowly depending on the specific method of use. Rapid hemostasis can also contribute to the reduction of major complications in some surgical procedures by facilitating a shorter procedure time. It is believed that the rapid hemostasis acts to quickly stop bleeding and the hydrogel comprises specific intrinsic properties resulting in the simultaneous capture, aggregation and concentration of platelets and red blood cells to initiate the cascade of coagulation, which is accomplished without the use of exogenously added clotting agents, drugs or other chemicals. The resulting hemostatic action assures that the device does not act simply as a tamponade or sealant that might allow the pooling of blood and formation of a hematoma under a sealant.

The hydrogel itself forms without the use of a third chemical or synthetic cross-linking agent and thus avoids the potential for irritation and cytotoxicity or the interference with predictable rapid biodegradation associated with cross-linking agents. Furthermore, due to the internal chemistry, the hydrogel itself gently and predictably contracts over time and does not swell, even when immersed in blood or body fluids. This feature permits the hemostats described herein to be used in brain, spinal or other surgical procedures in which swelling of a hemostatic agent can lead to mass effects and subsequent complications, which themselves require medical or surgical intervention.

Furthermore, the hydrogel provided herein is essentially transparent, so that a surgeon can visually verify its action and effect in real time. This feature allows surgeons to proceed with the surgical procedure and close the site while verifying hemostasis, in contrast to hemostats which are opaque.

Furthermore, the hydrogel provided herein is cohesively strong and thus can quickly establish its initial tamponade effect. Furthermore, the hemostat is also adherent and does not migrate away from the application site. The hydrogel forms in intimate continuous contact with the bleeding site so that all sources of bleeding are exposed and treated to the hemostatic action of the device.

The hemostatic hydrogel is produced by combining a defined acrylated chitosan composition as described herein to a defined oxidized dextran composition also described herein to produce a hemostatic hydrogel having the structural and/or functional properties discussed herein. The characteristics of the acrylated chitosan and oxidized dextran together with their respective syntheses required to produce a hemostatic hydrogel having the desired properties are discussed below.

In one aspect, the invention provides an acrylated chitosan composition for use in creating the hemostat described herein, wherein the acrylated chitosan composition comprises acrylated chitosan comprising:

(i) from about 0.01 to about 0.3 mole fraction of a first monomer of formula (I)

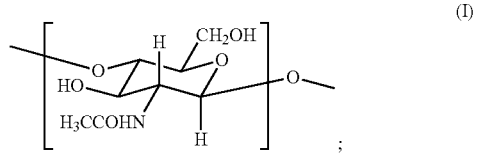

(ii) from about 0.3 to about 0.75 mole fraction of a second monomer of formula (II)

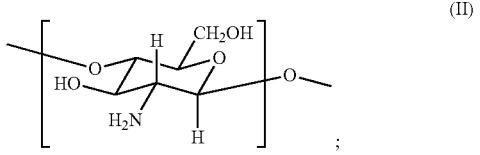

and (iii) from about 0.2 to about 0.7 mole fraction of a third monomer of formula (III)

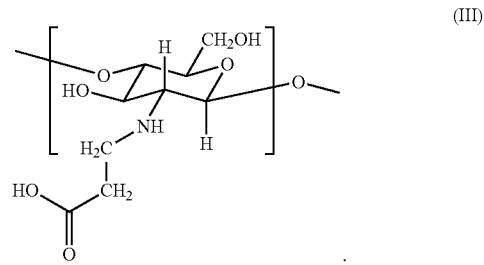

In certain embodiments, the acrylated chitosan composition comprises (i) from about 0.01 to about 0.26 mole fraction of the first monomer of formula (I), (ii) from about 0.35 to about 0.65 mole fraction of the second monomer of formula (II), (iii) from about 0.3 to about 0.6 mole fraction of the third monomer of formula (III), or a combination of (i) and (ii), (i) and (iii), (ii) and (iii), and (i), (ii) and (iii). In certain embodiments, the acrylated chitosan comprises less than about 0.1 mole fraction of a fourth monomer of formula (IV)

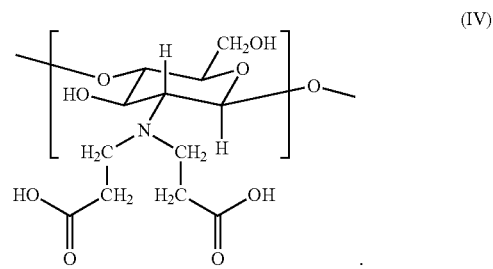

In each of the foregoing, the acrylated chitosan can have (i) a weight-average molecular weight (Mw) of from about 25 kDa to about 400 kDa or from about 115 kDa to about 200 kDa, (ii) a number-average molecular weight (Mn) of from about 14 kDa to about 200 kDa or from about 55 kDa to about 140 kDa, (iii) a polydispersity index (PDI) of from about 1.5 (Mw/Mn) to about 3.5 (Mw/Mn), (iv) a PDI of from about 1.5 (Mz/Mw) to about 7.0 (Mz/Mw), or from about 1.6 (Mz/Mw) to about 3.0 (Mz/Mw) or a combination of two, three or four of each of the foregoing features.

In certain embodiments, the acrylated chitosan composition comprises from about 1% (w/w) to about 25% (w/w), or from about 1% (w/w) to about 10% (w/w). In other embodiments, the acrylated chitosan composition has a viscosity of from about 10 cP to about 50,000 cP, or from about 100 cP to about 25,000 cP.

In another aspect, the invention provides a method of preparing an acrylated chitosan composition (for example, the acrylated chitosan compositions described above) comprising the steps of (a) contacting a raw chitosan material with an acetic acid solution (e.g., a 1% (v/v) acetic acid solution) to form a chitosan intermediate; (b) contacting the intermediate chitosan material with acrylic acid to form an acrylated chitosan intermediate; and (c) purifying the acrylated chitosan intermediate to produce an acrylated chitosan composition of the present invention.

In certain embodiments, during step (a), the step of contacting the raw chitosan material with the acetic acid solution is conducted at (i) a pressure of about 2 atmospheres, (ii) a temperature from about 80° C. to about 120° C., or a combination thereof. In certain embodiments, during step (a), (i) the PDI (Mw/Mn) of the chitosan intermediate is from about 15% to about 40% less than the PDI (Mw/Mn) of the raw chitosan material, (ii) the raw chitosan material has a PDI of from about 1.5 (Mw/Mn) to about 5.0 (Mw/Mn), (iii) the raw chitosan material has a degree of deacetylation of from about 65% to about 99% or from about 70% to about 98%, or a combination of (i) and (ii), (i) and (iii), (ii) and (iii), and (i), (ii) and (iii).

In certain embodiments, the during step (b), (i) the first chitosan intermediate is contacted with the acrylic acid at a temperature from about 50° C. to about 120° C., (ii) the acrylated chitosan intermediate has a degree of substitution (DS) value of from about 25% to about 65%, or a combination of (i) and (ii). In certain embodiments, the method further comprises the step of precipitating the acrylated chitosan composition to provide a solid and then optionally or in addition dissolving the solid into an aqueous medium to form a solution comprising an amount of the acrylated chitosan composition. In certain embodiments, the acrylated chitosan composition comprises from about 1% to about 25%, or from about 1% to about 10% by weight of the total weight of the solution.

In another embodiment, the invention provides a method of preparing an acrylated chitosan composition comprising the steps of: (a) contacting a raw chitosan material with an acetic acid solution to form a chitosan intermediate, wherein the raw chitosan material has a PDI of from about 1.5 (Mw/Mn) to about 5.0 (Mw/Mn); (b) contacting the intermediate chitosan with acrylic acid to form an acrylated chitosan intermediate having a degree of substitution (DS) value of from about 25% to about 65%; and (c) purifying the acrylated chitosan intermediate to produce an acrylated chitosan composition of the present invention. The method may further comprise the step of precipitating the acrylated chitosan composition produced in step (c) to provide a solid and then optionally or in addition dissolving the solid into an aqueous medium to form a solution comprising from about 1% to about 10% acrylated chitosan composition (w/w) of the total weight of the solution.

In another aspect, the invention provides an oxidized dextran composition for use in creating the hemostat described herein, wherein the oxidized dextran composition comprises oxidized dextran comprising:
(a) less than about 0.8 mole fraction of a first monomer of formula (V)

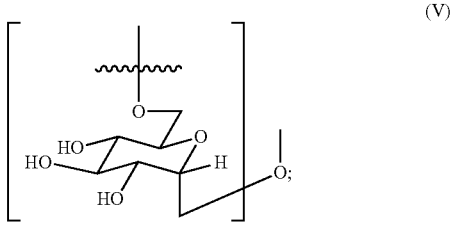

and
(b) from about 0.1 to about 1.0 mole fraction of a second monomer, wherein the second monomer is selected from a monomer of formula (VI), a monomer of formula (VII) and a combination of formula (VI) and formula (VII)

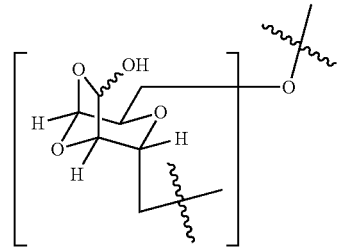

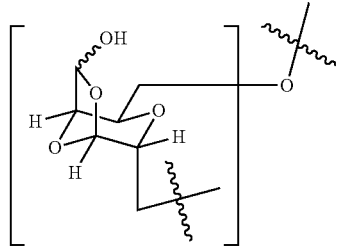

In certain embodiments, the oxidized dextran composition comprises (i) from about 0.4 to about 0.7 mole fraction of the first monomer of formula (V), (ii) from about 0.15 to about 0.35 mole fraction of the second monomer, (iii) comprises less than about 0.65 mole fraction of a third monomer of formula (VIII)

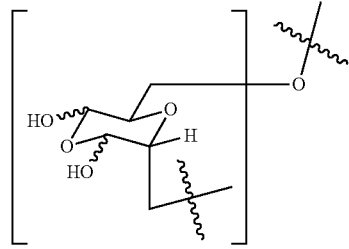

or a combination of (i) and (ii), (i) and (iii), (ii) and (ii), or (i), (ii) and (iii).

In certain embodiments, the oxidized dextran has (i) a Mw of from about 10 kDa to about 300 kDa or from about 15 kDa to about 90 kDa, (ii) a Mn of from about 4 kDa to about 166 kDa or from about 4 kDa to about 45 kDa, (iii) a PDI of from about 1.8 (Mw/Mn) to about 6.0 (Mw/Mn) or from about 2.0 (Mw/Mn) to about 4.0 (Mw/Mn), (iv) a PDI of from about 1.5 (Mz/Mw) to about 6.0 (Mz/Mw) or from about 1.5 (Mz/Mw) to about 5.0 (Mz/Mw), or a combination of any of the foregoing features.

In certain embodiments, the oxidized dextran comprises a total amount of aldehyde groups of from about 0.5 to about 2.0 or from about 0.6 to about 0.9 mol aldehydes/mol oxidized dextran. In other embodiments, the oxidized dextran contains a ratio of primary aldehyde groups to secondary aldehyde groups from about 1.8 to about 6.0 or from about 1.8 to about 3.5. In certain other embodiments, the oxidized dextran composition has a degree of oxidation from about 25% to about 100% or from about 30% to about 50%. In certain other embodiments, the oxidized dextran composition comprises from about 1% (w/w) to about 25% (w/w), or from about 1% (w/w) to about 10% (w/w) of the oxidized dextran. In certain other embodiments, the oxidized dextran composition has a viscosity of from about 1 cP to about 2,000 cP, or from about 1 cP to about 100 cP, from about 1 cP to about 10 cP.

In another aspect, the invention provides a method of preparing an oxidized dextran composition (for example, any of the oxidized dextran compositions described herein), the method comprising the steps of: (a) contacting a raw dextran material with an oxidizing agent to form an oxidized dextran intermediate; and (b) purifying the oxidized dextran intermediate to produce an oxidized dextran composition of the present invention.

In certain embodiments, the raw dextran material has (i) a Mw of from about 50 kDa to about 2,000 kDa, (ii) a PDI of from about 1.4 (Mw/Mn) to about 5.0 (Mw/Mn), or a combination of (i) and (ii). In certain embodiments, the oxidizing agent is a periodate salt. In certain embodiments, the method comprises the additional step of precipitating the oxidized dextran composition to provide a solid and then optionally or in addition comprises the step of dissolving the solid into an aqueous medium to form a solution comprising an amount of the oxidized dextran composition. In certain embodiments, the amount of the oxidized dextran composition is from about 1% (w/w) to about 25% (w/w), or from about 1% (w/w) to about 10% (w/w) by weight of the total weight of the solution.

In another aspect, the invention provides a hemostatic hydrogel composition containing oxidized dextran and acrylated chitosan, wherein the hydrogel composition has two or more of the following features:

(i) the hydrogel composition comprises a total amount of free aldehyde groups of from about 0.1 to about 0.7 moles aldehyde/mole oxidized dextran, (ii) the hydrogel composition is formed from oxidized dextran and acrylated chitosan, wherein the ratio of primary aldehydes in the oxidized dextran to the amines in the acrylated chitosan is in the range from about 1.0 to about 2.0, and/or the ratio of total aldehydes in in the oxidized dextran to amines in the acrylated chitosan is from about 1.5 to about 3.0, (iii) the ratio of Mw of the acrylated chitosan to the oxidized dextran is from about 2 to about 10 the ratio of Mn of the acrylated chitosan to the oxidized dextran is from about 4 to about 15, the ratio of Mz of the acrylated chitosan to the oxidized dextran is from about 2 to about 10, the ratio of PDI (Mw/Mn) of acrylated chitosan to oxidized dextran is from about 0.5 to about 0.8, and/or the ratio of PDI (Mz/Mw) of acrylated chitosan to oxidized dextran is from about 0.5 to about 1.0, (iv) upon formation of the hydrogel composition, the hydrogel composition comprises a bound water content of from about 65% w/w to about 95% w/w, (v) the hydrogel composition comprises a three-dimensional porous structure comprising layers of substantially non-interconnected pores having (a) a pore size distribution from about 10 μm to about 850 μm in diameter, (b) a platelet adhesive surface, or a combination of (a) and (b), (vi) the hydrogel composition comprises walls disposed between the substantially non-interconnected pores, the walls having a wall thickness of from 0.046 μm to 50 μm, (vii) the hydrogel composition comprises pores certain of which define a platelet adhesive surface so that, when in contact with blood, the hydrogel composition permits platelets and/or red blood cells within the blood to adhere to the platelet adhesive surface and promote blood clot formation at or within the hydrogel composition, (viii) the hydrogel composition comprises pores certain of which define a platelet adhesive surface so that, when in contact with blood, the hydrogel composition permits platelets and/or red blood cells within the blood to adhere to the platelet adhesive surface and not permit platelets and/or red blood cells from the blood to enter pores present in a first surface of the hydrogel composition, pass through the hydrogel composition, and then exit the hydrogel composition via pores present in a second surface of the hydrogel composition that opposes the first surface, (ix) at about 10 seconds after the formation of the hydrogel composition, the hydrogel composition has a burst strength of greater than 20 mmHg as determined using an ASTM F 2392-04 protocol, (x) at about 2 minutes after the formation of the hydrogel composition, the hydrogel composition has a burst strength of greater than about 35 mmHg as determined using an ASTM F 2392-04 protocol, (xi) at about 5 minutes after the formation of the hydrogel composition, the hydrogel composition has a burst strength of greater than about 70 mmHg as determined using an ASTM F 2392-04 protocol, (xii) the hydrogel composition has an elastic modulus of from about 500 Pa to about 5000 Pa at from about 10 seconds to about 80 seconds after the formation of the hydrogel composition, (xiii) the hydrogel composition has a compression modulus of from about 3 kPa to about 250 kPa, (xiv) the hydrogel composition has an average adhesion strength of from about 1.0 N to about 50 N, as determined using an ASTM F 2258-05 protocol, (xv) the volume of the hydrogel composition, when formed, does not increase upon exposure to a physiological fluid or body fluid, (xvi) the volume of the hydrogel composition shrinks by less than about 5% about 10 minutes after formation when exposed to a physiological fluid or body fluid, (xvii) the hydrogel composition is substantially transparent when the hydrogel composition has a thickness of 2 mm to 10 mm, and (xviii) the hydrogel composition optionally further comprises a therapeutic agent.

In certain embodiments, the hemostatic hydrogel composition comprises:

(a) from about 0.0 to about 0.3 mole fraction of a first monomer of formula (I)

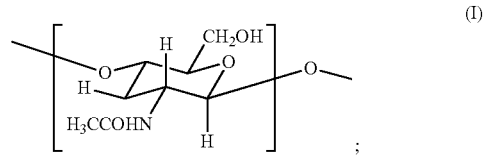

(b) from about 0.02 to about 0.7 mole fraction of a second monomer of formula (III),

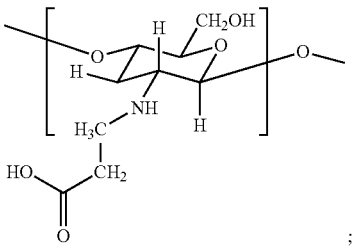

and (c) from about 0.0 to about 0.8 mole fraction of a second monomer of formula (V),

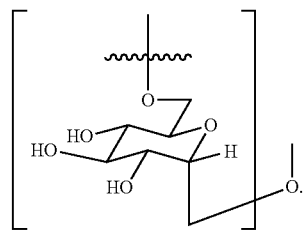

In certain embodiments, the hemostatic hydrogel composition of comprises (i) from about 0.0 to about 0.26 mole fraction of the first monomer of formula (I), (ii) from about 0.03 to about 0.6 mole fraction of the third monomer of formula (III), (iii) from about 0.04 to about 0.7 mole fraction of the first monomer of formula (V), or a combination or (i) and (ii), (i) and (iii), (ii) and (iii) and (i), (ii) and (iii).

In certain embodiments, the hemostatic hydrogel composition comprises (i) no greater than about 0.2 mole fraction of a fourth monomer of formula (IV)

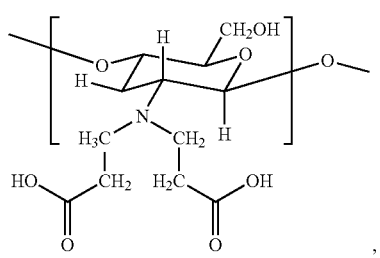

(ii) no greater than about 0.65 mole fraction of a fifth monomer of formula (VIII)

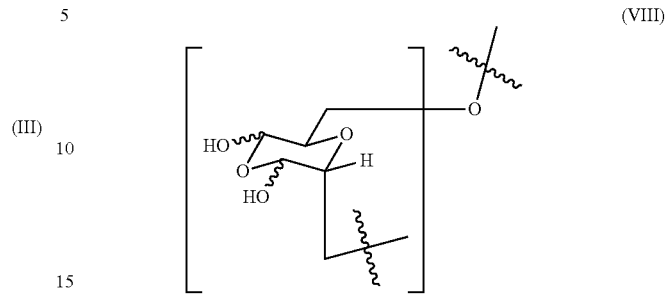

or a combination or (i) and (ii).

In certain embodiments, the hemostatic hydrogel comprises a plurality of crosslinked moieties of formula (IX)

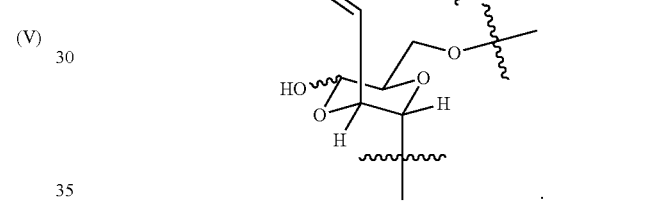

In another aspect, the invention provides a method of preparing a hemostatic hydrogel composition (such as the hemostatic hydrogel compositions described herein), the method comprising contacting an acrylated chitosan composition as described herein with an oxidized dextran composition as described herein so as to form the hemostatic hydrogel composition.

In certain embodiments, the ratio of the viscosity of the acrylated chitosan composition to the oxidized dextran composition ranges from about 100:1 to about 10,000:1. In certain embodiments, the hemostatic agent further comprises a therapeutic agent or a cell, for example, a stem cell.

In certain embodiments, the hemostatic hydrogel is produced by contacting the acrylated chitosan composition described herein with the oxidized dextran composition described herein in a static mixer and optionally or in addition then aerosolizing the mixture prior to application to tissue. In certain embodiments, the gelation time of the hemostatic hydrogel composition ranges within from about 10 seconds to about 240 seconds after contacting the acrylated chitosan composition with the oxidized dextran composition.

In another aspect, the invention provides a method of promoting hemostasis (e.g., reducing or stopping blood loss) at a location in a subject in need thereof. The method comprises forming at the location in the subject the hemostatic hydrogel composition described herein thereby to promote hemostasis (e.g., reduce or stop blood loss) at the location. It is understood that the hemostatic hydrogel composition adheres to a tissue surface at the location. Furthermore, it is understood that the hydrogel permits the platelets and/or red blood cells to adhere to or otherwise become disposed on the surfaces of pores in the hemostatic hydrogel and promote a blood coagulation cascade at the location thereby to produce a blood clot. It understood that blood loss at the location can be caused by, for example, trauma, abrasion, or surgical intervention at the location.

The hemostatic composition, when applied to the location, can fill a cavity at the location without inducing compression of tissue surrounding the cavity when the hemostatic composition is exposed to physiological fluid or a body fluid. It is understood that hemostasis can be achieved from about 5 seconds to about 120 seconds, from about 10 seconds to about 120 seconds, from about 15 seconds to about 120 seconds, from about 5 seconds to about 60 seconds, from about 10 seconds to about 60 seconds, from about 15 seconds to about 60 seconds, from about 5 seconds to about 30 seconds, from about 10 seconds to about 30 seconds, from about 15 seconds to about 30 seconds, from about 5 seconds to about 15 seconds, or from about 10 seconds to about 15 seconds, after the hemostatic hydrogel composition is applied to the location.

DETAILED DESCRIPTION OF THE INVENTION

I Definitions

Figure 1:
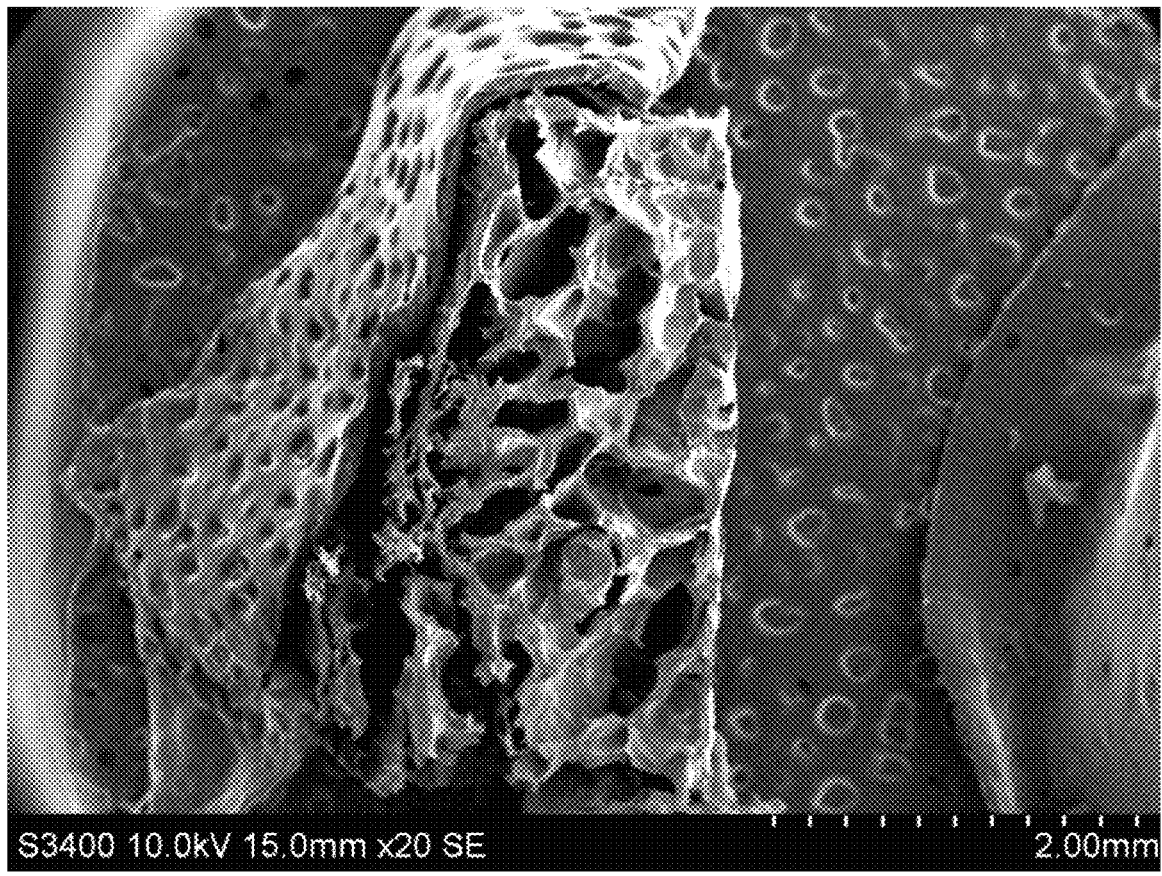
FIG. 1 is a scanning election microscope (SEM) image of the internal three-dimensional structure of an exemplary acrylated chitosan/oxidized dextran hydrogel.

To facilitate an understanding of the present invention, a number of terms and phrases are defined below.

The terms "a" and "an" as used herein mean "one or more" and include the plural unless the context is inappropriate.

As used herein, the term "tissue" refers to material that forms the solid or semi-solid structures that make up any of the organs or components of a living organism and includes, for example, membrane, skin, muscle, bone, cartilage, nerve and nerve sheathe, meninge, connective tissue, blood vessel, the sclera or iris of the eye, the solid materials constituting internal organs such as liver, stomach, pancreas, intestine, kidney, thymus, uterus, testes, bladder, lung, heart and any other internal structures that are solid or semi-solid in texture. Thus, liquids such as blood are not considered to be a tissue.

"Adhere" or "adherence" refers to the creation of a physical bond between material and tissue such that a moderate motion or force does not cause separation of the material from the tissue on which it is disposed. The physical bond that is created between the material and the tissue that requires hemostasis may have one or several bases including electrostatic bonding and covalent bonding, but any mechanism by which the adherence occurs in contemplated herein.

The terms "adhesive" and "adhesivity" similarly refer to the existence of a physical bond between two materials such as a hemostat of the present invention and the tissue to which the hemostat is applied. An adhesive is a material which adheres to tissue or other material and which may be used to constrain the separation of two tissue masses. Adhesivity is the property or degree to which a material adheres to a tissue or other material.

As used herein, the term "hydrogel" refers to a material of solid or semi-solid texture that comprises water. Hydrogels are formed by a three-dimensional network of molecular structures within which water, among other substances, may be retained. The three-dimensional molecular network may be held together by covalent chemical bonds, or by ionic bonds, or by any combination thereof.

The act of "gelation" refers to the formation of a gel, for example, a hydrogel.

A "saccharide" as used herein refers to a carbohydrate. The term "carbohydrate" includes the class of compounds commonly known as sugars, in addition to compounds that are chemically related to sugars. The term thus includes simple "monosaccharide" sugars, "disaccharide" sugars as well as polymeric "polysaccharides." The term encompasses a group of compounds including sugars, starches, gums, cellulose and hemicelluloses. The term further encompasses sugar derivatives such as amino-sugars, for example, 2-amino-2-deoxyglucose, as well as their oligomers and polymers; sulfated sugars; and sugars with hydroxyl, amino, carboxyl and other groups.

As used herein, the term "chitosan" refers to a polysaccharide polymer, either obtained from a natural source such as chitin, or synthetically prepared. Chemically, chitosan is predominantly a polymer of β-1,4-linked 2-amino-2-deoxyglucose monomers. When prepared from a natural source, the usual natural source is chitin, a major constituent of the shells of arthropods (e.g., crabs, lobsters, and shrimp), mollusks, annelids, and cephalopods (e.g., squid). Other natural sources of chitin include plants (e.g., fungi and algae). Chitin is chemically a polymer comprising β-1,4-linked 2-acetamino-2-deoxyglucose monomers. After isolation of chitin from its natural source, it is treated to cause hydrolysis of the acetamido group without cleavage of the sugar-sugar bonds, typically through alkaline hydrolysis. Chitosan is not a single molecular entity, but rather comprises polymeric chains of various lengths.

As used herein, the term "raw chitosan material" refers to chitosan preparation derived from chitin derived from arthropods (e.g., crabs, lobsters, and shrimp), mollusks, annelids, cephalopods (e.g., squid), or plants (e.g., fungi) that has been treated to cause hydrolysis of the acetamido groups without substantial cleavage of sugar-sugar bonds, for example, by alkaline hydrolysis.

As used herein, the term "alkylated chitosan" refers to a chitosan molecule in which a carbon containing moiety has been covalently bonded. The term "alkylated chitosan" comprises a large number of possible chemical structures that share a common feature that chemical bonds have been formed between the components of the chitosan molecules and at least one carbon atom in each of the molecules that are bonded to the chitosan. For example, alkylated chitosan includes the methylation of chitosan, in which bonds are formed between methyl radicals or groups and atoms within the chitosan molecule, such as nitrogen, oxygen or carbon atoms. Other carbon-containing groups may likewise be chemically bonded to chitosan molecules to produce an alkylated chitosan. Examples include poly(oxyalkylene)chitosan, wherein poly(oxyethylene), or polyethyleneglycol, chains are covalently bonded to the chitosan backbone, as well as acrylated chitosans, formed by alkylation of chitosan with acrylates.

As used herein, the term "acrylated chitosan" refers to an alkylated chitosan wherein one or more acrylate groups have been allowed to react with, and form chemical bonds to, the chitosan molecule. An acrylate is a molecule containing an 4-unsaturated carbonyl group; thus, acrylic acid is prop-2-enoic acid. The acrylate may bond to the chitosan through a Michael addition of the chitosan nitrogen atoms with the acrylate.

As used herein, the term "degree of substitution" of a polymeric species refers to the ratio of the average number of substituent groups, for example an alkyl substituent, per monomeric unit of the polymer.

As used herein, the terms "swell", "swells" or "swelling" refers to the increase in mass and/or volume of a material (e.g., a hemostatic hydrogel composition of the present invention), by greater than about 3% of the material's original mass and/or volume following exposure to a physiological fluid, body fluid, or aqueous medium.

As used herein, the term "aqueous medium" refers to a liquid medium composed largely, but not necessarily exclusively, of water. Other components may also be present, such as salts, co-solvents, buffers, stabilizers, dispersants, colorants and the like.

As used herein, the terms "subject" and "patient" refer to organisms to be treated by the methods and/or compositions described herein. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the terms "treat," "treating," and "treatment" include any effect, e.g., lessening, reducing, modulating, ameliorating or eliminating, that results in the improvement of the condition, disease, disorder, and the like, or ameliorating a symptom thereof.

The phrase "therapeutically-effective amount" as used herein means that amount of a compound, material, or composition comprising a compound of the present invention which is effective for producing some desired therapeutic effect in a subject.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

The following sections describe the synthesis of acrylated chitosan and oxidized dextran which are used to form the hemostatic compositions described herein.

II Acrylated Chitosan

In one aspect, the invention provides acrylated chitosan useful in producing the hemostatic compositions described herein. In certain embodiments, the acrylated chitosan compositions comprise acrylated chitosan comprising:

(i) from about 0.01 to about 0.3 mole fraction of a first monomer of formula (I)

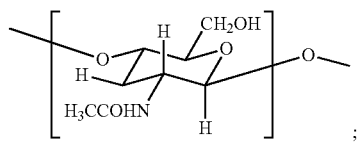

(ii) from about 0.3 to about 0.75 mole fraction of a second monomer of formula (II)

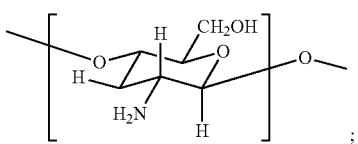

and (iii) from about 0.2 to about 0.7 mole fraction of a third monomer of formula (III)

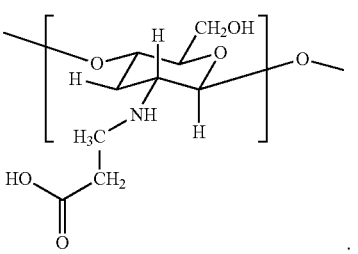

The term mole fraction, as used herein, refers to the mole fraction of a monomer present in a polymer and/or hydrogel composition disclosed herein, as determined without including the contribution of solvent (e.g., water) in the polymer and/or hydrogel composition.

In certain embodiments, the acrylated chitosan comprises from about 0.01 to about 0.26, from about 0.02 to about 0.26, from about 0.03 to about 0.26, from about 0.04 to about 0.26, from about 0.05 to about 0.26, from about 0.06 to about 0.26, from about 0.02 to about 0.23, from about 0.02 to about 0.19, from about 0.02 to about 0.16, from about 0.02 to about 0.13, from about 0.02 to about 0.1, from about 0.02 to about 0.07, from about 0.02 to about 0.04, from about 0.03 to about 0.23, from about 0.03 to about 0.19, from about 0.03 to about 0.16, from about 0.03 to about 0.13, from about 0.03 to about 0.1, from about 0.03 to about 0.07, from about 0.03 to about 0.04, from about 0.04 to about 0.23, from about 0.04 to about 0.19, from about 0.04 to about 0.16, from about 0.04 to about 0.13, from about 0.04 to about 0.1, from about 0.04 to about 0.07, from about 0.05 to about 0.23, from about 0.05 to about 0.19, from about 0.05 to about 0.16, from about 0.05 to about 0.13, from about 0.05 to about 0.1, from about 0.05 to about 0.07, from about 0.06 to about 0.23, from about 0.06 to about 0.19, from about 0.06 to about 0.16, from about 0.06 to about 0.13, from about 0.06 to about 0.1, or from about 0.06 to about 0.07 mole fraction of the first monomer of formula (I). In certain embodiments, the acrylated chitosan comprises from about 0.01 to about 0.26 mole fraction of the first monomer of formula (I). In certain embodiments, the acrylated chitosan comprises from about 0.02 to about 0.04, about 0.04 to about 0.07, or about 0.06 to about 0.16 mole fraction of the first monomer of formula (I).

In certain embodiments, the acrylated chitosan comprises from about 0.35 to about 0.65, from about 0.4 to about 0.65, from about 0.45 to about 0.65, from about 0.5 to about 0.65, from about 0.55 to about 0.65, from about 0.6 to about 0.65, from about 0.35 to about 0.6, from about 0.35 to about 0.6, from about 0.35 to about 0.55, from about 0.35 to about 0.5, from about 0.35 to about 0.45, from about 0.35 to about 0.4, from about 0.4 to about 0.6, from about 0.4 to about 0.55, from about 0.4 to about 0.5, from about 0.4 to about 0.45, from about 0.45 to about 0.6, from about 0.45 to about 0.55, from about 0.45 to about 0.5, from about 0.5 to about 0.6, from about 0.5 to about 0.55, or from about 0.55 to about 0.6 mole fraction of the second monomer of formula (II). In certain embodiments, wherein the acrylated chitosan comprises from about 0.35 to about 0.65 mole fraction of the second monomer of formula (II). In certain embodiments, wherein the acrylated chitosan comprises from about 0.35 to about 0.5, from about 0.45 to about 0.55, from about 0.5 to about 0.6 mole fraction of the second monomer of formula (II).

In certain embodiments, the acrylated chitosan comprises from about 0.3 to about 0.6, from about 0.35 to about 0.6, from about 0.4 to about 0.6, from about 0.45 to about 0.6, from about 0.5 to about 0.6, from about 0.55 to about 0.6, from about 0.3 to about 0.55, from about 0.3 to about 0.5, from about 0.3 to about 0.45, from about 0.3 to about 0.4, from about 0.3 to about 0.35, from about 0.35 to about 0.55, from about 0.35 to about 0.5, from about 0.35 to about 0.45, from about 0.35 to about 0.4, from about 0.4 to about 0.55, from about 0.4 to about 0.5, from about 0.4 to about 0.45, from about 0.45 to about 0.55, from about 0.45 to about 0.5, or from about 0.5 to about 0.55 mole fraction of the third monomer of formula (III). In certain embodiments, wherein the acrylated chitosan comprises from about 0.3 to about 0.6 mole fraction of the third monomer of formula (III). In certain embodiments, wherein the acrylated chitosan comprises from about 0.3 to about 0.45, about 0.4 to about 0.45 mole fraction, or about 0.4 to about 0.55 of the third monomer of formula (III).

In certain embodiments, the acrylated chitosan further comprises less than about 0.1 mole fraction of a fourth monomer of formula (IV)

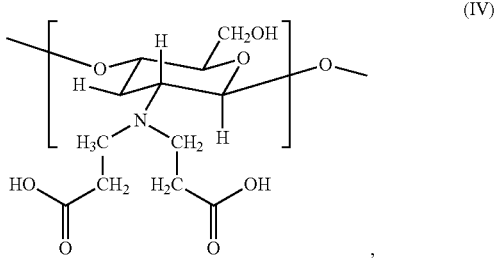
(IV)

In certain embodiments, the acrylated chitosan further comprises less than about 0.03 mole fraction of the fourth monomer of formula (IV). In certain embodiments, the acrylated chitosan further comprises from about 0.01 to about 0.03, from about 0.015 to about 0.03, from about 0.02 to about 0.03, from about 0.025 to about 0.03, from about 0.01 to about 0.025, from about 0.01 to about 0.02, from about 0.01 to about 0.015, from about 0.015 to about 0.025, from about 0.015 to about 0.02, or from about 0.02 to about 0.025 mole fraction of the fourth monomer of formula (IV). In certain embodiments, the acrylated chitosan further comprises from about 0.01 to about 0.03 mole fraction of the fourth monomer of formula (IV).

In certain embodiments, the acrylated chitosan has a Mw of from about 25 kDa to about 400 kDa, from about 25 kDa to about 300 kDa, from about 25 kDa to about 200 kDa, from about 50 kDa to about 400 kDa, from about 50 kDa to about 300 kDa, from about 50 kDa to about 200 kDa, from about 115 kDa to about 200 kDa, from about 115 kDa to about 175 kDa, from about 115 kDa to about 165 kDa, from about 115 kDa to about 155 kDa, from about 115 kDa to about 145 kDa, from about 115 kDa to about 135 kDa, from about 115 kDa to about 125 kDa, from about 125 kDa to about 200 kDa, from about 125 kDa to about 175 kDa, from about 125 kDa to about 165 kDa, from about 125 kDa to about 155 kDa, from about 125 kDa to about 145 kDa, from about 125 kDa to about 135 kDa, from about 135 kDa to about 200 kDa, from about 135 kDa to about 175 kDa, from about 135 kDa to about 165 kDa, from about 135 kDa to about 155 kDa, from about 135 kDa to about 145 kDa, from about 145 kDa to about 200 kDa, from about 145 kDa to about 175 kDa, from about 145 kDa to about 165 kDa, from about 145 kDa to about 155 kDa, from about 155 kDa to about 200 kDa, from about 155 kDa to about 175 kDa, from about 155 kDa to about 165 kDa, from about 165 kDa to about 200 kDa, from about 165 kDa to about 175 kDa, or from about 175 kDa to about 200 kDa.

In certain embodiments, the acrylated chitosan has a Mw of from about 25 kDa to about 400 kDa. In certain embodiments, the acrylated chitosan has a Mw of from about 115 kDa to about 200 kDa. In certain embodiments, the acrylated chitosan has a Mw of from about 115 kDa to about 165 kDa, from about 125 kDa to about 155 kDa, or from about 135 kDa to about 175 kDa.

In certain embodiments, the acrylated chitosan has a Mn of from about 14 kDa to about 200 kDa, from about 14 kDa to about 150 kDa, from about 25 kDa to about 200 kDa, from about 14 kDa to about 150 kDa, from about 55 kDa to about 140 kDa, from about 55 kDa to about 120 kDa, from about 55 kDa to about 100 kDa, from about 55 kDa to about 90 kDa, from about 55 kDa to about 80 kDa, from about 55 kDa to about 75 kDa, from about 55 kDa to about 70 kDa, from about 55 kDa to about 65 kDa, from about 55 kDa to about 60 kDa, from about 60 kDa to about 140 kDa, from about 60 kDa to about 120 kDa, from about 60 kDa to about 100 kDa, from about 60 kDa to about 90 kDa, from about 60 kDa to about 80 kDa, from about 60 kDa to about 75 kDa, from about 60 kDa to about 70 kDa, from about 60 kDa to about 65 kDa, from about 65 kDa to about 140 kDa, from about 65 kDa to about 120 kDa, from about 65 kDa to about 100 kDa, from about 65 kDa to about 90 kDa, from about 65 kDa to about 80 kDa, from about 65 kDa to about 75 kDa, from about 65 kDa to about 70 kDa, from about 70 kDa to about 140 kDa, from about 70 kDa to about 120 kDa, from about 70 kDa to about 100 kDa, from about 70 kDa to about 90 kDa, from about 70 kDa to about 80 kDa, from about 70 kDa to about 75 kDa, from about 75 kDa to about 140 kDa, from about 75 kDa to about 120 kDa, from about 75 kDa to about 100 kDa, from about 75 kDa to about 90 kDa, from about 75 kDa to about 80 kDa, from about 80 kDa to about 140 kDa, from about 80 kDa to about 120 kDa, from about 80 kDa to about 100 kDa, from about 80 kDa to about 90 kDa, from about 90 kDa to about 140 kDa, from about 90 kDa to about 120 kDa, from about 90 kDa to about 100 kDa, from about 100 kDa to about 140 kDa, from about 100 kDa to about 120 kDa, or from about 120 kDa to about 140 kDa.

In certain embodiments, wherein the acrylated chitosan has a Mn of from about 14 kDa to about 200 kDa. In certain embodiments, wherein the acrylated chitosan has a Mn of from about 55 kDa to about 140 kDa. In certain embodiments, wherein the acrylated chitosan has a Mn of from about 55 kDa to about 75 kDa, from about 65 kDa to about 75 kDa, or from about 65 kDa to about 100 kDa.

In certain embodiments, the acrylated chitosan has a PDI of from about 1.5 (Mw/Mn) to about 3.5 (Mw/Mn), from about 1.7 (Mw/Mn) to about 3.5 (Mw/Mn), from about 2.1 (Mw/Mn) to about 3.5 (Mw/Mn), from about 2.4 (Mw/Mn) to about 3.5 (Mw/Mn), from about 2.7 (Mw/Mn) to about 3.5 (Mw/Mn), from about 3.0 (Mw/Mn) to about 3.5 (Mw/Mn), from about 3.3 (Mw/Mn) to about 3.5 (Mw/Mn), from about 1.5 (Mw/Mn) to about 3.3 (Mw/Mn), from about 1.5 (Mw/Mn) to about 3.0 (Mw/Mn), from about 1.5 (Mw/Mn) to about 2.7 (Mw/Mn), from about 1.5 (Mw/Mn) to about 2.4 (Mw/Mn), from about 1.5 (Mw/Mn) to about 2.1 (Mw/Mn), from about 1.5 (Mw/Mn) to about 1.8 (Mw/Mn), from about 1.7 (Mw/Mn) to about 3.3 (Mw/Mn), from about 1.7 (Mw/Mn) to about 3.0 (Mw/Mn), from about 1.7 (Mw/Mn) to about 2.7 (Mw/Mn), from about 1.7 (Mw/Mn) to about 2.4 (Mw/Mn), from about 1.7 (Mw/Mn) to about 2.1 (Mw/Mn), from about 1.9 (Mw/Mn) to about 3.3 (Mw/Mn), from about 1.9 (Mw/Mn) to about 3.0 (Mw/Mn), from about 1.9 (Mw/Mn) to about 2.7 (Mw/Mn), from about 1.9 (Mw/Mn) to about 2.4 (Mw/Mn), from about 1.9 (Mw/Mn) to about 2.1 (Mw/Mn), from about 2.1 (Mw/Mn) to about 3.3 (Mw/Mn), from about 2.1 (Mw/Mn) to about 3.0 (Mw/Mn), from about 2.1 (Mw/Mn) to about 2.7 (Mw/Mn), from about 2.1 (Mw/Mn) to about 2.4 (Mw/Mn), from about 2.3 (Mw/Mn) to about 3.3 (Mw/Mn), from about 2.3 (Mw/Mn) to about 3.0 (Mw/Mn), from about 2.3 (Mw/Mn) to about 2.7 (Mw/Mn), from about 2.3 (Mw/Mn) to about 2.4 (Mw/Mn), from about 2.5 (Mw/Mn) to about 3.3 (Mw/Mn), from about 2.5 (Mw/Mn) to about 3.0 (Mw/Mn), from about 2.5 (Mw/Mn) to about 2.7 (Mw/Mn), from about 2.7 (Mw/Mn) to about 3.3 (Mw/Mn), from about 2.7 (Mw/Mn) to about 3.0 (Mw/Mn), from about 2.9 (Mw/Mn) to about 3.3 (Mw/Mn), from about 2.9 (Mw/Mn) to about 3.0 (Mw/Mn), or from about 3.1 (Mw/Mn) to about 3.3 (Mw/Mn).

In certain embodiments, the acrylated chitosan has a PDI of from about 1.5 (Mw/Mn) to about 3.5 (Mw/Mn). In certain embodiments, the acrylated chitosan has a PDI of from about 1.5 (Mw/Mn) to about 2.4 (Mw/Mn), from about 1.7 (Mw/Mn) to about 2.1 (Mw/Mn), or from about 2.1 (Mw/Mn) to about 3.0 (Mw/Mn).

In certain embodiments, the acrylated chitosan has a Mz of from about 80 kDa to about 1,200 kDa, from about 80 kDa to about 600 kDa, from about 80 kDa to about 370 kDa, from about 150 kDa to about 1,200 kDa, from about 150 kDa to about 600 kDa, from about 150 kDa to about 370 kDa, from about 200 kDa to about 370 kDa, from about 200 kDa to about 350 kDa, from about 200 kDa to about 320 kDa, from about 200 kDa to about 300 kDa, from about 200 kDa to about 270 kDa, from about 200 kDa to about 260 kDa, from about 200 kDa to about 250 kDa, from about 200 kDa to about 240 kDa, from about 200 kDa to about 230 kDa, from about 200 kDa to about 220 kDa, from about 200 kDa to about 210 kDa, from about 210 kDa to about 370 kDa, from about 210 kDa to about 350 kDa, from about 210 kDa to about 320 kDa, from about 210 kDa to about 300 kDa, from about 210 kDa to about 270 kDa, from about 210 kDa to about 260 kDa, from about 210 kDa to about 250 kDa, from about 210 kDa to about 240 kDa, from about 210 kDa to about 230 kDa, from about 210 kDa to about 220 kDa, from about 220 kDa to about 370 kDa, from about 220 kDa to about 350 kDa, from about 220 kDa to about 320 kDa, from about 220 kDa to about 300 kDa, from about 220 kDa to about 270 kDa, from about 220 kDa to about 260 kDa, from about 220 kDa to about 250 kDa, from about 220 kDa to about 240 kDa, from about 220 kDa to about 230 kDa, from about 230 kDa to about 370 kDa, from about 230 kDa to about 350 kDa, from about 230 kDa to about 320 kDa, from about 230 kDa to about 300 kDa, from about 230 kDa to about 270 kDa, from about 230 kDa to about 260 kDa, from about 230 kDa to about 250 kDa, from about 240 kDa to about 370 kDa, from about 240 kDa to about 350 kDa, from about 240 kDa to about 320 kDa, from about 240 kDa to about 300 kDa, from about 240 kDa to about 270 kDa, from about 240 kDa to about 260 kDa, from about 240 kDa to about 250 kDa, from about 250 kDa to about 370 kDa, from about 250 kDa to about 350 kDa, from about 250 kDa to about 320 kDa, from about 250 kDa to about 300 kDa, from about 250 kDa to about 270 kDa, from about 250 kDa to about 260 kDa, from about 260 kDa to about 370 kDa, from about 260 kDa to about 350 kDa, from about 260 kDa to about 320 kDa, from about 260 kDa to about 300 kDa, from about 270 kDa to about 370 kDa, from about 270 kDa to about 350 kDa, from about 270 kDa to about 320 kDa, from about 270 kDa to about 300 kDa, from about 300 kDa to about 370 kDa, from about 300 kDa to about 350 kDa, from about 300 kDa to about 320 kDa, from about 320 kDa to about 370 kDa, from about 320 kDa to about 350 kDa, or from about 350 kDa to about 370 kDa.

In certain embodiments, the acrylated chitosan has a Mz of from about 80 kDa to about 1,200 kDa. In certain embodiments, the acrylated chitosan has a Mz of from about 200 kDa to about 350 kDa. In certain embodiments, the acrylated chitosan has a Mz of from about 200 kDa to about 300 kDa, from about 210 kDa to about 370 kDa, or from about 250 kDa to about 370 kDa.

In certain embodiments, the acrylated chitosan has a PDI of from about 1.5 (Mz/Mw) to about 7.0 (Mz/Mw), from about 1.5 (Mz/Mw) to about 5.0 (Mz/Mw), from about 1.5 (Mz/Mw) to about 3.0 (Mz/Mw), from about 1.6 (Mz/Mw) to about 3.0 (Mz/Mw), from about 1.6 (Mz/Mw) to about 2.5 (Mz/Mw), from about 1.6 (Mz/Mw) to about 2.0 (Mz/Mw), from about 1.6 (Mz/Mw) to about 1.9 (Mz/Mw), from about 1.6 (Mz/Mw) to about 1.8 (Mz/Mw), from about 1.6 (Mz/Mw) to about 1.7 (Mz/Mw), from about 1.7 (Mz/Mw) to about 3.0 (Mz/Mw), from about 1.7 (Mz/Mw) to about 2.5 (Mz/Mw), from about 1.7 (Mz/Mw) to about 2.0 (Mz/Mw), from about 1.7 (Mz/Mw) to about 1.9 (Mz/Mw), from about 1.7 (Mz/Mw) to about 1.8 (Mz/Mw), from about 1.8 (Mz/Mw) to about 3.0 (Mz/Mw), from about 1.8 (Mz/Mw) to about 2.5 (Mz/Mw), from about 1.8 (Mz/Mw) to about 2.0 (Mz/Mw), from about 1.8 (Mz/Mw) to about 1.9 (Mz/Mw), from about 1.9 (Mz/Mw) to about 3.0 (Mz/Mw), from about 1.9 (Mz/Mw) to about 2.5 (Mz/Mw), from about 1.9 (Mz/Mw) to about 2.0 (Mz/Mw), from about 2.0 (Mz/Mw) to about 3.0 (Mz/Mw), from about 2.0 (Mz/Mw) to about 2.5 (Mz/Mw), or from about 2.5 (Mz/Mw) to about 3.0 (Mz/Mw).

In certain embodiments, the acrylated chitosan has a PDI of from about 1.5 (Mz/Mw) to about 7.0 (Mz/Mw). In certain embodiments, the acrylated chitosan has a PDI of from about 1.6 (Mz/Mw) to about 3.0 (Mz/Mw). In certain embodiments, the acrylated chitosan has a PDI of from about 1.5 (Mz/Mw) to about 2.0 (Mz/Mw), from about 1.6 (Mz/Mw) to about 2.5 (Mz/Mw), from about 1.9 (Mz/Mw) to about 3.0 (Mz/Mw).

In certain embodiments, the acrylated chitosan composition comprises about 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), about 20% (w/w), about 21% (w/w), about 22% (w/w), about 23% (w/w), about 24% (w/w), or about 25% (w/w) of the acrylated chitosan.

In certain embodiments, the acrylated chitosan composition comprises from about 1% (w/w) to about 25% (w/w), from about 1% (w/w) to about 20% (w/w), from about 1% (w/w) to about 15% (w/w), from about 1% (w/w) to about 10% (w/w), from about 1% (w/w) to about 9% (w/w), from about 1% (w/w) to about 8% (w/w), from about 1% (w/w) to about 7% (w/w), from about 1% (w/w) to about 6% (w/w), from about 1% (w/w) to about 5% (w/w), from about 1% (w/w) to about 4% (w/w), from about 1% (w/w) to about 3% (w/w), from about 1% (w/w) to about 2% (w/w), from about 2% (w/w) to about 10% (w/w), from about 2% (w/w) to about 9% (w/w), from about 2% (w/w) to about 8% (w/w), from about 2% (w/w) to about 7% (w/w), from about 2% (w/w) to about 6% (w/w), from about 2% (w/w) to about 5% (w/w), from about 2% (w/w) to about 4% (w/w), from about 2% (w/w) to about 3% (w/w), from about 3% (w/w) to about 10% (w/w), from about 3% (w/w) to about 9% (w/w), from about 3% (w/w) to about 8% (w/w), from about 3% (w/w) to about 7% (w/w), from about 3% (w/w) to about 6% (w/w), from about 3% (w/w) to about 5% (w/w), from about 3% (w/w) to about 4% (w/w), from about 4% (w/w) to about 10% (w/w), from about 4% (w/w) to about 9% (w/w), from about 4% (w/w) to about 8% (w/w), from about 4% (w/w) to about 7% (w/w), from about 4% (w/w) to about 6% (w/w), from about 4% (w/w) to about 5% (w/w), from about 5% (w/w) to about 10% (w/w), from about 5% (w/w) to about 9% (w/w), from about 5% (w/w) to about 8% (w/w), from about 5% (w/w) to about 7% (w/w), from about 5% (w/w) to about 6% (w/w), from about 6% (w/w) to about 10% (w/w), from about 6% (w/w) to about 9% (w/w), from about 6% (w/w) to about 8% (w/w), from about 6% (w/w) to about 7% (w/w), from about 7% (w/w) to about 10% (w/w), from about 7% (w/w) to about 9% (w/w), from about 7% (w/w) to about 8% (w/w), from about 8% (w/w) to about 10% (w/w), from about 8% (w/w) to about 9% (w/w), or from about 9% (w/w) to about 10% (w/w) of the acrylated chitosan. In certain embodiments, the acrylated chitosan composition comprises from about 1% (w/w) to about 25% (w/w). In certain embodiments, the acrylated chitosan composition comprises from about 1% (w/w) to about 10% (w/w) of the acrylated chitosan. In certain embodiments, the acrylated chitosan composition comprises from about 2% (w/w) to about 5% (w/w), from about 4% (w/w) to about 7% (w/w), or from about 6% (w/w) to about 9% (w/w).

In certain embodiments, the acrylated chitosan composition has a viscosity of from about 10 cP to about 50,000 cP, from about 10 cP to about 35,000 cP, from about 10 cP to about 25,000 cP, from about 10 cP to about 20,000 cP, from about 10 cP to about 10,000 cP, from about 10 cP to about 8,000 cP, from about 10 cP to about 4,000 cP, from about 10 cP to about 1,000 cP, from about 10 cP to about 100 cP, from about 100 cP to about 25,000 cP, from about 100 cP to about 20,000 cP, from about 100 cP to about 10,000 cP, from about 100 cP to about 8,000 cP, from about 100 cP to about 4,000 cP, from about 100 cP to about 1,000 cP, from about 1,000 cP to about 25,000 cP, from about 1,000 cP to about 20,000 cP, from about 1,000 cP to about 10,000 cP, from about 1,000 cP to about 8,000 cP, from about 1,000 cP to about 4,000 cP, from about 4,000 cP to about 25,000 cP, from about 4,000 cP to about 20,000 cP, from about 4,000 cP to about 10,000 cP, from about 4,000 cP to about 8,000 cP, from about 8,000 cP to about 25,000 cP, from about 8,000 cP to about 20,000 cP, from about 8,000 cP to about 10,000 cP, or from about 10,000 cP to about 20,000 cP.

In certain embodiments, the acrylated chitosan composition has a viscosity of from about 10 cP to about 50,000 cP. In certain embodiments, the acrylated chitosan composition has a viscosity of from about 100 cP to about 25,000 cP. In certain embodiments, the acrylated chitosan composition has a viscosity of from about 1,000 cP to about 10,000 cP, about 8,000 cP to about 20,000 cP, or from about 10,000 cP to about 25,000 cP.

In certain embodiments, the acrylated chitosan composition has a pH of from about 5.5 to about 9.0, from about 6.0 to about 9.0, from about 6.5 to about 9.0, from about 7.0 to about 9.0, from about 7.5 to about 9.0, from about 8.0 to about 9.0, from about 8.5 to about 9.0, from about 8.0 to about 8.8, from about 8.0 to about 8.6, from about 8.0 to about 8.4, from about 8.0 to about 8.2, from about 8.2 to about 8.8, from about 8.2 to about 8.6, from about 8.2 to about 8.4, from about 8.4 to about 8.8, from about 8.4 to about 8.6, or from about 8.6 to about 8.8. In certain embodiments, the acrylated chitosan composition has a pH of from about 5.5 to about 9.0. In certain embodiments, the acrylated chitosan composition has a pH of from about 8.0 to about 8.4, from about 8.2 to about 8.8, or from about 8.2 to about 8.8.

In certain embodiments, the acrylated chitosan composition has a conductivity of from about 0.75 (mS/cm) to about 25.0 (mS/cm), from about 0.75 (mS/cm) to about 20.0 (mS/cm), from about 0.75 (mS/cm) to about 15.0 (mS/cm), from about 0.75 (mS/cm) to about 10.0 (mS/cm), from about 0.75 (mS/cm) to about 5.0 (mS/cm), from about 0.75 (mS/cm) to about 4.0 (mS/cm), from about 0.75 (mS/cm) to about 3.0 (mS/cm), from about 0.75 (mS/cm) to about 2.0 (mS/cm), from about 0.75 (mS/cm) to about 1.0 (mS/cm), from about 1.0 (mS/cm) to about 10.0 (mS/cm), from about 1.0 (mS/cm) to about 5.0 (mS/cm), from about 1.0 (mS/cm) to about 4.0 (mS/cm), from about 1.0 (mS/cm) to about 3.0 (mS/cm), from about 1.0 (mS/cm) to about 2.0 (mS/cm), from about 2.0 (mS/cm) to about 10.0 (mS/cm), from about 2.0 (mS/cm) to about 5.0 (mS/cm), from about 2.0 (mS/cm) to about 4.0 (mS/cm), from about 2.0 (mS/cm) to about 3.0 (mS/cm), from about 3.0 (mS/cm) to about 10.0 (mS/cm), from about 3.0 (mS/cm) to about 5.0 (mS/cm), from about 3.0 (mS/cm) to about 4.0 (mS/cm), from about 4.0 (mS/cm) to about 10.0 (mS/cm), from about 4.0 (mS/cm) to about 5.0 (mS/cm), or from about 5.0 (mS/cm) to about 10.0 (mS/cm).

In certain embodiments, the acrylated chitosan composition has a conductivity of from about 0.75 (mS/cm) to about 25.0 (mS/cm). In certain embodiments, the acrylated chitosan composition has a conductivity of from about 0.75 (mS/cm) to about 10 (mS/cm). In certain embodiments, the acrylated chitosan composition has a conductivity of from about 1.0 (mS/cm) to about 5.0 (mS/cm), from about 3.0 (mS/cm) to about 10.0 (mS/cm), or from about 5.0 (mS/cm) to about 10.0 (mS/cm).

In certain embodiments, the acrylated chitosan has two or more properties selected from a Mw of from about 25 kDa to about 400 kDa, a Mn of from about 14 kDa to about 200 kDa, a PDI of from about 1.5 to about 3.5 (Mw/Mn), an Mz of from about 80 kDa to about 1,200 kDa, and a PDI of from about 1.5 to about 7.0 (Mz/Mw).

In certain embodiments, the acrylated chitosan composition comprises a plurality (e.g., 2, 3, 4, 5, 6, 7, or 8) or all of the following features: (i) a Mw of from about 115 kDa to about 200 kDa, (ii) a Mn of from about 55 kDa to about 140 kDa, (iii) a Mz of from about 200 kDa to about 350 kDa, (iv) a PDI (Mw/Mn) of from about 1.5 to about 3.5, (v) a PDI (Mz/Mw) of from about 1.6 to about 3.0, (vi) a mole fraction of the monomer of formula (I) of from about 0.011 to about 0.26, (vii) a mole fraction of the monomer of formula (II) of from about 0.35 to about 0.65, (viii) a mole fraction of the monomer of formula (III) of from about 0.32 to about 0.6, and (ix) a mole fraction of the monomer of formula (IV) of from about 0.09 to about 0.028.

In certain embodiments, the acrylated chitosan composition comprises a plurality (e.g., 2, 3, 4, 5, 6, 7, 8, 9, 10, 11, or 12) or all of the following features: (i) a Mw of from about 115 kDa to about 200 kDa, (ii) a Mn of from about 55 kDa to about 140 kDa, (iii) a Mz of from about 200 kDa to about 350 kDa, (iv) a PDI (Mw/Mn) of from about 1.5 to about 3.5, (v) a PDI (Mz/Mw) of from about 1.6 to about 3.0, (vi) a mole fraction of the monomer of formula (I) of from about 0.011 to about 0.26, (vii) a mole fraction of the monomer of formula (II) of from about 0.35 to about 0.65, (viii) a mole fraction of the monomer of formula (III) of from about 0.32 to about 0.6, (ix) a mole fraction of the monomer of formula (IV) of from about 0.09 to about 0.028, (x) a concentration of the acrylated chitosan in an aqueous medium or from about 1% (w/w) to about 10% (w/w), (xi) a viscosity of from about 10 cP to about 20,300 cP, (xii) a pH of from about 5.5 to about 9.0, and (xiii) a conductivity of from about 0.75 mS/cm to about 10.0 mS/cm.

III Methods of Making Acrylated Chitosan

In one aspect, the invention provides a method of preparing an acrylated chitosan composition useful in making a hemostatic composition described herein. The method comprises the steps of:
  (a) contacting a raw chitosan material with an acetic acid solution to form a chitosan intermediate;
  (b) contacting the intermediate chitosan material with acrylic acid to form an acrylated chitosan intermediate; and
  (c) purifying the acrylated chitosan intermediate to produce an acrylated chitosan composition of the present invention.

In certain embodiments, during step (a), the raw chitosan material is contacted with the acetic acid solution at a pressure of about 0.5 atmospheres, about 1.0 atmosphere, about 1.5 atmospheres, about 2 atmospheres, about 2.5 atmospheres, about 3.0 atmospheres, about 3.5 atmospheres, about 4.0 atmospheres, about 4.5 atmospheres, or about 5.0 atmospheres. In certain embodiments, during step (a), the raw chitosan material is contacted with the acetic acid solution at a pressure of about 2 atmospheres.

In certain embodiments, during step (a), the raw chitosan material is contacted with the acetic acid solution at a temperature of about 80° C., about 85° C., about 90° C., about 95° C., about 100° C., about 115° C., or about 120° C. In certain embodiments, during step (a), the raw chitosan material is contacted with the acetic acid solution at a temperature from about 80° C. to about 120° C., from about 90° C. to about 120° C., from about 100° C. to about 120° C., from about 110° C. to about 120° C., from about 80° C. to about 110° C., from about 80° C. to about 100° C., from about 80° C. to about 90° C., from about 90° C. to about 110° C., from about 90° C. to about 100° C., or from about 100° C. to about 110° C. In certain embodiments, during step (a), the raw chitosan material is contacted with the acetic acid solution at a temperature from about 80° C. to about 120° C.

In certain embodiments, during step (a), the acetic acid solution is a 1% (v/v) acetic acid solution, a 2% (v/v) acetic acid solution, a 3% (v/v) acetic acid solution, a 4% (v/v) acetic acid solution, a 5% (v/v) acetic acid solution, a 6% (v/v) acetic acid solution, a 7% (v/v) acetic acid solution, a 8% (v/v) acetic acid solution, a 9% (v/v) acetic acid solution, or a 10% (v/v) acetic acid solution. In certain embodiments, during step (a), the acetic acid solution is a 1% (v/v) acetic acid solution.

In certain embodiments, during step (a), the acetic acid solution is a 1% (w/v) acetic acid solution, a 2% (w/v) acetic acid solution, a 3% (w/v) acetic acid solution, a 4% (w/v) acetic acid solution, a 5% (w/v) acetic acid solution, a 6% (w/v) acetic acid solution, a 7% (w/v) acetic acid solution, a 8% (w/v) acetic acid solution, a 9% (w/v) acetic acid solution, or a 10% (w/v) acetic acid solution. In certain embodiments, during step (a), the acetic acid solution is a 1% (w/v) acetic acid solution.

In certain embodiments, during step (a), the raw chitosan material has a weight-average molecular weight (Mw) of from about 40 kDa to about 1,000 kDa, about 50 kDa to about 750 kDa, about 50 kDa to about 500 kDa, about 100 kDa to about 750 kDa, from about 100 kDa to about 500 kDa, from about 100 kDa to about 450 kDa, from about 100 kDa to about 400 kDa, from about 100 kDa to about 350 kDa, from about 100 kDa to about 300 kDa, from about 100 kDa to about 250 kDa, from about 100 kDa to about 200 kDa, from about 100 kDa to about 150 kDa, from about 150 kDa to about 500 kDa, from about 150 kDa to about 450 kDa, from about 150 kDa to about 400 kDa, from about 150 kDa to about 350 kDa, from about 150 kDa to about 300 kDa, from about 150 kDa to about 250 kDa, from about 150 kDa to about 200 kDa, from about 200 kDa to about 500 kDa, from about 200 kDa to about 450 kDa, from about 200 kDa to about 400 kDa, from about 200 kDa to about 350 kDa, from about 200 kDa to about 300 kDa, from about 200 kDa to about 250 kDa, from about 250 kDa to about 500 kDa, from about 250 kDa to about 450 kDa, from about 250 kDa to about 400 kDa, from about 250 kDa to about 350 kDa, from about 250 kDa to about 300 kDa, from about 300 kDa to about 500 kDa, from about 300 kDa to about 450 kDa, from about 300 kDa to about 400 kDa, from about 300 kDa to about 350 kDa, from about 350 kDa to about 500 kDa, from about 350 kDa to about 450 kDa, from about 350 kDa to about 400 kDa, from about 400 kDa to about 500 kDa, from about 400 kDa to about 450 kDa, or from about 450 kDa to about 500 kDa. In certain embodiments, during step (a), the raw chitosan material has a Mw of from about 40 kDa to about 1,000 kDa. In certain embodiments, during step (a), the raw chitosan material has a Mw of from about 100 kDa to about 500 kDa. In certain embodiments, during step (a), the raw chitosan material has a Mw of from about 100 kDa to about 250 kDa, from about 200 kDa to about 350 kDa, or from about 300 kDa to about 450 kDa.

In certain embodiments, during step (a), the raw chitosan material has a number-average molecular weight (Mn) of greater than 10 kDa, greater than 15 kDa, greater than 20 kDa, greater than 25 kDa, greater than 30 kDa, greater than 35 kDa, greater than 40 kDa, greater than 45 kDa, greater than 50 kDa, greater than 55 kDa, greater than 60 kDa, greater than 65 kDa, greater than 70 kDa, greater than 75 kDa, greater than 80 kDa, greater than 85 kDa, greater than 90 kDa, greater than 95 kDa, greater than 100 kDa, greater than 105 kDa, greater than 110 kDa, greater than 115 kDa, greater than 120 kDa. In certain embodiments, during step (a), the raw chitosan material has a number-average molecular weight (Mn) of greater than 20 kDa. In certain embodiments, during step (a), the raw chitosan material has a number-average molecular weight (Mn) of greater than 60 kDa. In certain embodiments, during step (a), the raw chitosan material has a number-average molecular weight (Mn) in the range of from about 20 kDa to about 650 kDa, from about 20 kDa to about 400 kDa, from about 20 kDa to about 300 kDa, from about 20 kDa to about 200 kDa, from about 40 kDa to about 400 kDa, from about 40 kDa to about 300 kDa, from about 40 kDa to about 200 kDa, from about 40 kDa to about 100 kDa, from about 100 kDa to about 300 kDa, from about 100 kDa to about 200 kDa, or from about 200 kDa to about 300 kDa. In certain embodiments, during step (a), the raw chitosan material has a number-average molecular weight (Mn) in the range of from about 20 kDa to about 650 kDa. In certain embodiments, during step (a), the raw chitosan material has a number-average molecular weight (Mn) in the range of from about 40 kDa to about 300 kDa.

In certain embodiments, during step (a), the raw chitosan material has a polydispersity index (PDI) of from about 1.5 (Mw/Mn) to about 5.0 (Mw/Mn), from about 1.6 (Mw/Mn) to about 4.5 (Mw/Mn), from about 1.6 (Mw/Mn) to about 4.0 (Mw/Mn), from about 1.7 (Mw/Mn) to about 4.0 (Mw/Mn), from about 1.7 (Mw/Mn) to about 3.5 (Mw/Mn), from about 1.7 (Mw/Mn) to about 3.0 (Mw/Mn), from about 1.7 (Mw/Mn) to about 2.5 (Mw/Mn), from about 1.7 (Mw/Mn) to about 2.0 (Mw/Mn), from about 1.8 (Mw/Mn) to about 4.0 (Mw/Mn), from about 1.8 (Mw/Mn) to about 3.5 (Mw/Mn), from about 1.8 (Mw/Mn) to about 3.0 (Mw/Mn), from about 1.8 (Mw/Mn) to about 2.5 (Mw/Mn), from about 1.8 (Mw/Mn) to about 2.0 (Mw/Mn), from about 1.9 (Mw/Mn) to about 4.0 (Mw/Mn), from about 1.9 (Mw/Mn) to about 3.5 (Mw/Mn), from about 1.9 (Mw/Mn) to about 3.0 (Mw/Mn), from about 1.9 (Mw/Mn) to about 2.5 (Mw/Mn), from about 1.9 (Mw/Mn) to about 2.0 (Mw/Mn), from about 2.0 (Mw/Mn) to about 4.0 (Mw/Mn), from about 2.0 (Mw/Mn) to about 3.5 (Mw/Mn), from about 2.0 (Mw/Mn) to about 3.0 (Mw/Mn), or from about 2.0 (Mw/Mn) to about 2.5 (Mw/Mn). In certain embodiments, during step (a), the raw chitosan material has a polydispersity index of from about 1.5 (Mw/Mn) to about 5.0 (Mw/Mn). In certain embodiments, during step (a), the raw chitosan material has a polydispersity index of from about 1.7 (Mw/Mn) to about 4.0 (Mw/Mn). In certain embodiments, during step (a), the raw chitosan material has a polydispersity index of from about 1.6 (Mw/Mn) to about 3.0 (Mw/Mn), about 1.8 (Mw/Mn) to about 3.5 (Mw/Mn) or from about 2.0 (Mw/Mn) to about 4.0 (Mw/Mn).

In certain embodiments, during step (a), the raw chitosan material has a z-average molecular weight (Mz) of from about 100 kDa to about 2000 kDa, about 100 kDa to about 1500 kDa, about 100 kDa to about 1000 kDa, about 200 kDa to about 2000 kDa, about 100 kDa to about 15000 kDa, about 100 kDa to about 1000 kDa, from about 250 kDa to about 750 kDa, from about 250 kDa to about 600 kDa, from about 250 kDa to about 500 kDa, from about 250 kDa to about 400 kDa, from about 250 kDa to about 300 kDa, from about 300 kDa to about 750 kDa, from about 300 kDa to about 600 kDa, from about 300 kDa to about 500 kDa, from about 300 kDa to about 400 kDa, from about 300 kDa to about 350 kDa, from about 350 kDa to about 750 kDa, from about 350 kDa to about 600 kDa, from about 350 kDa to about 500 kDa, from about 350 kDa to about 400 kDa, from about 400 kDa to about 750 kDa, from about 400 kDa to about 600 kDa, from about 400 kDa to about 500 kDa, from about 500 kDa to about 750 kDa, from about 500 kDa to about 600 kDa, or from about 600 kDa to about 750 kDa. In certain embodiments, during step (a), the raw chitosan material has a Mz of from about 100 kDa to about 2000 kDa. In certain embodiments, during step (a), the raw chitosan material has a Mz of from about 250 kDa to about 750 kDa. In certain embodiments, during step (a), the raw chitosan material has a Mz of from about 250 kDa to about 500 kDa, from about 350 kDa to about 600 kDa or from about 400 kDa to about 750 kDa.

In certain embodiments, during step (a), the raw chitosan material has a polydispersity index (PDI) of from about 1.5 (Mz/Mw) to about 4.0 (Mz/Mw), from about 1.5 (Mz/Mw) to about 3.75 (Mz/Mw), from about 1.5 (Mz/Mw) to about 3.5 (Mz/Mw), from about 1.5 (Mz/Mw) to about 3.0 (Mz/Mw), from about 1.5 (Mz/Mw) to about 2.5 (Mz/Mw), from about 1.5 (Mz/Mw) to about 2.0 (Mz/Mw), from about 2.0 (Mz/Mw) to about 3.75 (Mz/Mw), from about 2.0 (Mz/Mw) to about 3.5 (Mz/Mw), from about 2.0 (Mz/Mw) to about 3.0 (Mz/Mw), from about 2.0 (Mz/Mw) to about 2.5 (Mz/Mw), from about 2.5 (Mz/Mw) to about 3.75 (Mz/Mw), from about 2.5 (Mz/Mw) to about 3.5 (Mz/Mw), from about 2.5 (Mz/Mw) to about 3.0 (Mz/Mw), from about 3.0 (Mz/Mw) to about 3.75 (Mz/Mw) or from about 3.0 (Mz/Mw) to about 3.5 (Mz/Mw). In certain embodiments, during step (a), the raw chitosan material has a polydispersity index (PDI) of from about 1.5 (Mz/Mw) to about 4.0 (Mz/Mw). In certain embodiments, during step (a), the raw chitosan material has a polydispersity index (PDI) of from about 1.5 (Mz/Mw) to about 3.5 (Mz/Mw). In certain embodiments, during step (a), the raw chitosan material has a polydispersity index (PDI) of from about 1.5 (Mz/Mw) to about 2.0 (Mz/Mw), from about 1.5 (Mz/Mw) to about 3.0 (Mz/Mw), or from about 2.5 (Mz/Mw) to about 3.75 (Mz/Mw).

In certain embodiments, during step (a), the PDI (Mw/Mn) of the chitosan intermediate is from about 10% to about 60%, from about 10% to about 50%, from about 10% to about 40%, from about 15% to about 40%, from about 20% to about 40%, from about 30% to about 40%, from about 15% to about 30%, from about 15% to about 20%, or from about 20% to about 30% less than the PDI (Mw/Mn) of the raw chitosan material. In certain embodiments, during step (a), the PDI (Mw/Mn) of the chitosan intermediate is from about 10% to about 60% less than the PDI (Mw/Mn) of the raw chitosan material. In certain embodiments, during step (a), the PDI (Mw/Mn) of the chitosan intermediate is from about 15% to about 40% less than the PDI (Mw/Mn) of the raw chitosan material.

In certain embodiments, during step (a), the raw chitosan material has a degree of deacetylation of from about 65% to about 100%, from about 70% to about 100%, from about 75% to about 100%, from about 80% to about 100%, from about 85% to about 100%, from about 90% to about 100%, from about 95% to about 100%, about 65% to about 99%, from about 70% to about 99%, from about 72.5% to about 99%, from about 75% to about 99%, from about 77.5% to about 99%, from about 80.0% to about 99%, about 65% to about 98%, from about 70% to about 98%, from about 72.5% to about 98%, from about 75% to about 98%, from about 77.5% to about 98%, from about 80.0% to about 98%, about 65% to about 97%, from about 70% to about 97%, from about 72.5% to about 97%, from about 75% to about 97%, from about 77.5% to about 97%, or from about 80.0% to about 97%. In certain embodiments, during step (a), the raw chitosan material has a degree of deacetylation of from about 65% to about 100%. In certain embodiments, during step (a), the raw chitosan material has a degree of deacetylation of from about 70% to about 98%. In certain embodiments, during step (a), the raw chitosan material has a degree of deacetylation of from about 65% to about 97%, from about 70% to about 98%, or from about 80% to about 99%.

In certain embodiments, the raw chitosan has two or more of the following features, a Mw of from about 100 kDa to about 500 kDa, a number-average molecular weight (Mn) in the range of from about 40 kDa to about 300 kDa, a PDI of from about 1.7 to about 4.0 (Mw/Mn), a z average molecular weight (Mz) of from about 250 kDa to about 750 kDa, a PDI from about 1.5 to about 4.0 (Mz/Mw), and a degree of deacetylation of from about 65% to about 100%.

In certain embodiments, during step (b), the first chitosan intermediate is contacted with the acrylic acid at a temperature of about 50° C., about 60° C., about 70° C., about 80° C., about 90° C., about 100° C., about 110° C., or about 120° C. In certain embodiments, during step (b), the first chitosan intermediate is contacted with the acrylic acid at a temperature from about 50° C. to about 120° C., from about 60° C. to about 120° C., from about 70° C. to about 120° C., from about 80° C. to about 120° C., from about 90° C. to about 120° C., from about 100° C. to about 120° C., from about 110° C. to about 120° C., from about 50° C. to about 110° C., from about 50° C. to about 100° C., from about 50° C. to about 90° C., from about 50° C. to about 80° C., from about 50° C. to about 70° C., from about 50° C. to about 60° C., from about 60° C. to about 110° C., from about 60° C. to about 100° C., from about 60° C. to about 90° C., from about 60° C. to about 80° C., from about 60° C. to about 70° C., from about 70° C. to about 110° C., from about 70° C. to about 100° C., from about 70° C. to about 90° C., from about 70° C. to about 80° C., from about 80° C. to about 110° C., from about 80° C. to about 100° C., from about 80° C. to about 90° C., from about 90° C. to about 110° C., from about 90° C. to about 100° C., or from about 100° C. to about 110° C. In certain embodiments, during step (b), the first chitosan intermediate is contacted with the acrylic acid at a temperature from about 50° C. to about 100° C.

In certain embodiments, the acrylated chitosan intermediate formed in step (b) has a degree of substitution (DS) value of from about 25% to about 65%.

In certain embodiments, during step (c), the acrylated chitosan intermediate is purified using a method selected from the group consisting of dialysis, gel filtration chromatography, stirred cell filtration, tangential flow filtration, and any combination thereof.

In certain embodiments, the yield of acrylated chitosan obtained following step (c) is from about 80% to about 100%, from about 85% to about 100%, from about 90% to about 100%, from about 95% to about 100%, from about 80% to about 95%, from about 80% to about 90%, from about 80% to about 85%, from about 85% to about 95%, from about 85% to about 90%, or from about 90% to about 95%. In certain embodiments, the yield of acrylated chitosan obtained following step (c) is from about 80% to about 97%.

In certain embodiments, the method further comprises the step of precipitating and/or lyophilizing the acrylated chitosan composition to provide a solid.

In certain embodiments, the method further comprises the step of dissolving the solid into an aqueous medium to form a solution comprising an amount of the acrylated chitosan composition of, for example, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight of the total weight of the solution.

In certain embodiments, the amount of the acrylated chitosan composition comprises from about 1% to about 25%, from about 1% to about 20%, from about 1% to about 15%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10%, by weight of the total weight of the solution.

In certain embodiments, the amount of the acrylated chitosan composition comprises from about 1% to about 25% by weight of the total weight of the solution. In certain embodiments, the amount of the acrylated chitosan composition comprises from about 1% to about 10% by weight of the total weight of the solution. In certain embodiments, the amount of the acrylated chitosan composition comprises from about 2% to about 5%, from about 4% to about 7%, or from about 5% to about 9%, by weight of the total weight of the solution.

In another aspect, provided herein is a method of preparing an acrylated chitosan composition comprising:
(a) contacting a raw chitosan material with an acetic acid solution to form a chitosan intermediate, wherein the raw chitosan material has a PDI of from about 1.5 (Mw/Mn) to about 5.0 (Mw/Mn);
(b) contacting the intermediate chitosan with acrylic acid to form an acrylated chitosan intermediate having a degree of substitution (DS) value of from about 25% to about 65%; and
(c) purifying the acrylated chitosan intermediate to produce an acrylated chitosan composition of the present invention.

In certain embodiments, the yield of acrylated chitosan obtained following step (c) is from about 80% to about 97%.

In certain embodiments, the method further comprising the step of precipitating the acrylated chitosan composition produced in step (c) to provide a solid. In certain embodiments, the method further comprising the step of lyophilizing the acrylated chitosan composition to provide a solid.

In certain embodiments, the method further comprising the step of dissolving the solid into an aqueous medium to form a solution comprising from about 1% to about 10% acrylated chitosan composition (w/w) of the total weight of the solution.

IV Oxidized Dextran Compositions

One aspect of the invention provides oxidized dextran compositions. In certain embodiments, the oxidized dextran compositions comprise an oxidized dextran comprising:

(i) less than about 0.8 mole fraction of a first monomer of formula (V)

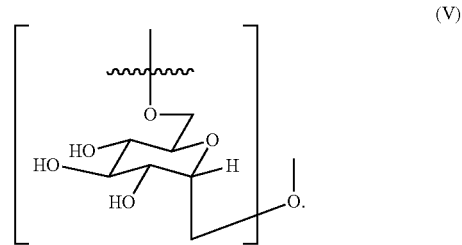

and (ii) about 0.1 to about 1.0 mole fraction of a second monomer, wherein the second monomer is selected from a monomer of formula (VI), a monomer of formula (VII) and a combination of formula (VI) and formula (VII)

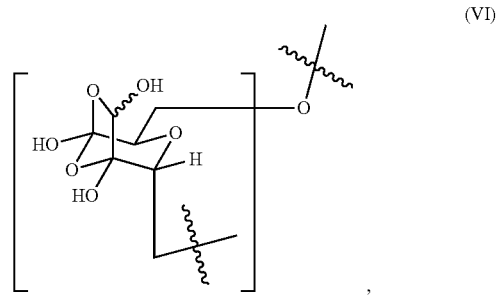

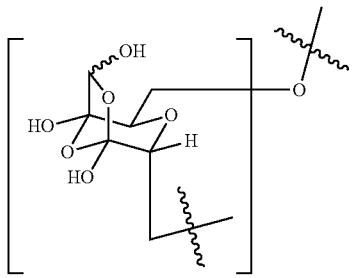 (VII)

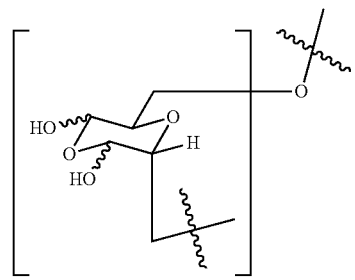 (VIII)

In certain embodiments, the oxidized dextran comprises from about 0.5 to about 0.7, from about 0.52 to about 0.7, from about 0.54 to about 0.7, from about 0.56 to about 0.7, from about 0.58 to about 0.7, from about 0.6 to about 0.7, from about 0.62 to about 0.7, from about 0.64 to about 0.7, from about 0.66 to about 0.7, from about 0.68 to about 0.7, from about 0.5 to about 0.68, from about 0.5 to about 0.66, from about 0.5 to about 0.64, from about 0.5 to about 0.62, from about 0.5 to about 0.6, from about 0.5 to about 0.58, from about 0.5 to about 0.56, from about 0.5 to about 0.54, from about 0.5 to about 0.52, from about 0.52 to about 0.68, from about 0.52 to about 0.66, from about 0.52 to about 0.64, from about 0.52 to about 0.62, from about 0.52 to about 0.6, from about 0.52 to about 0.58, from about 0.52 to about 0.56, from about 0.52 to about 0.54, from about 0.54 to about 0.68, from about 0.54 to about 0.66, from about 0.54 to about 0.64, from about 0.54 to about 0.62, from about 0.54 to about 0.6, from about 0.54 to about 0.58, from about 0.54 to about 0.56, from about 0.56 to about 0.68, from about 0.56 to about 0.66, from about 0.56 to about 0.64, from about 0.56 to about 0.62, from about 0.56 to about 0.6, from about 0.56 to about 0.58, from about 0.58 to about 0.68, from about 0.58 to about 0.66, from about 0.58 to about 0.64, from about 0.58 to about 0.62, from about 0.58 to about 0.6, from about 0.6 to about 0.68, from about 0.6 to about 0.66, from about 0.6 to about 0.64, from about 0.6 to about 0.62, from about 0.62 to about 0.68, from about 0.62 to about 0.66, from about 0.62 to about 0.64, from about 0.64 to about 0.68, from about 0.64 to about 0.66, or from about 0.66 to about 0.68 mole fraction of the first monomer of formula (V). In certain embodiments, the oxidized dextran comprises from about 0.4 to about 0.7 mole fraction of the first monomer of formula (V). In certain embodiments, the oxidized dextran comprises from about 0.52 to about 0.6, about 0.56 to about 0.62, or about 0.6 to about 0.66 mole fraction of the first monomer of formula (V).

In certain embodiments, the oxidized dextran comprises from about 0.15 to about 0.35, from about 0.2 to about 0.35, from about 0.25 to about 0.35, from about 0.3 to about 0.35, from about 0.15 to about 0.3, from about 0.15 to about 0.25, from about 0.15 to about 0.2, from about 0.2 to about 0.3, from about 0.2 to about 0.25, or from about 0.25 to about 0.3 mole fraction of the second monomer. In certain embodiments, the oxidized dextran comprises from about 0.15 to about 0.35 mole fraction of the second monomer. In certain embodiments, the oxidized dextran comprises from about 0.15 to about 0.25, about 0.2 to about 0.3, or about 0.25 to about 0.35 mole fraction of the second monomer.

In certain embodiments, wherein the oxidized dextran further comprises less than about 0.65 mole fraction of a third monomer of formula (VIII)

In certain embodiments, the oxidized dextran comprises from about 0.1 to about 0.16, from about 0.11 to about 0.16, from about 0.12 to about 0.16, from about 0.13 to about 0.16, from about 0.14 to about 0.16, from about 0.15 to about 0.16, from about 0.1 to about 0.15, from about 0.1 to about 0.14, from about 0.1 to about 0.13, from about 0.1 to about 0.12, from about 0.1 to about 0.11, from about 0.11 to about 0.15, from about 0.11 to about 0.14, from about 0.11 to about 0.13, from about 0.11 to about 0.12, from about 0.12 to about 0.15, from about 0.12 to about 0.14, from about 0.12 to about 0.13, from about 0.13 to about 0.15, from about 0.13 to about 0.14, or from about 0.14 to about 0.15 mole fraction of a third monomer of formula (VIII). In certain embodiments, the oxidized dextran comprises from about 0.1 to about 0.16 mole fraction of a third monomer of formula (VIII). In certain embodiments, the oxidized dextran comprises from about 0.11 to about 0.14, about 0.12 to about 0.15, or about 0.13 to about 0.15 mole fraction of a third monomer of formula (VIII).

In certain embodiments, wherein the oxidized dextran has a Mw of from about 10 kDa to about 300 kDa, about 10 kDa to about 200 kDa, about 15 kDa to about 300 kDa, about 15 kDa to about 200 kDa, from about 15 kDa to about 90 kDa, from about 15 kDa to about 80 kDa, from about 15 kDa to about 70 kDa, from about 15 kDa to about 80 kDa, from about 15 kDa to about 70 kDa, from about 15 kDa to about 60 kDa, from about 15 kDa to about 50 kDa, from about 15 kDa to about 40 kDa, from about 15 kDa to about 30 kDa, from about 15 kDa to about 25 kDa, from about 15 kDa to about 20 kDa, from about 20 kDa to about 90 kDa, from about 20 kDa to about 80 kDa, from about 20 kDa to about 70 kDa, from about 20 kDa to about 60 kDa, from about 20 kDa to about 70 kDa, from about 20 kDa to about 60 kDa, from about 20 kDa to about 50 kDa, from about 20 kDa to about 40 kDa, from about 20 kDa to about 30 kDa, from about 20 kDa to about 25 kDa, from about 25 kDa to about 90 kDa, from about 25 kDa to about 80 kDa, from about 25 kDa to about 70 kDa, from about 25 kDa to about 60 kDa, from about 25 kDa to about 70 kDa, from about 25 kDa to about 60 kDa, from about 25 kDa to about 50 kDa, from about 25 kDa to about 40 kDa, from about 25 kDa to about 30 kDa, from about 30 kDa to about 90 kDa, from about 30 kDa to about 80 kDa, from about 30 kDa to about 70 kDa, from about 30 kDa to about 60 kDa, from about 30 kDa to about 50 kDa, from about 30 kDa to about 40 kDa, from about 40 kDa to about 90 kDa, from about 40 kDa to about 80 kDa, from about 40 kDa to about 70 kDa, from about 40 kDa to about 60 kDa, from about 40 kDa to about 50 kDa, from about 50 kDa to about 90 kDa, from about 50 kDa to about 80 kDa, from about 50 kDa to about 70 kDa, from about 50 kDa to about 60 kDa, from about 60 kDa to about 90 kDa, from about 60 kDa to about 80 kDa, from about 60 kDa to about 70 kDa, from about 70 kDa to about 90 kDa, from about 70 kDa to about 80 kDa, or from about 80 kDa to about 90 kDa.

In certain embodiments, wherein the oxidized dextran has a Mw of from about 10 kDa to about 300 kDa. In certain embodiments, wherein the oxidized dextran has a Mw of from about 15 kDa to about 90 kDa. In certain embodiments, wherein the oxidized dextran has a Mw of from about 15 kDa to about 20 kDa, from about 15 kDa to about 25 kDa or from about 20 kDa to about 50 kDa.

In certain embodiments, the oxidized dextran has a Mn of from about 4 kDa to about 166 kDa, about 4 kDa to about 100 kDa, from about 4 kDa to about 50 kDa, from about 4 kDa to about 40 kDa, from about 4 kDa to about 30 kDa, from about 4 kDa to about 20 kDa, from about 4 kDa to about 10 kDa, from about 4 kDa to about 9 kDa, from about 4 kDa to about 8 kDa, from about 4 kDa to about 7 kDa, from about 4 kDa to about 6 kDa, from about 4 kDa to about 5 kDa, from about 5 kDa to about 50 kDa, from about 5 kDa to about 40 kDa, from about 5 kDa to about 30 kDa, from about 5 kDa to about 20 kDa, from about 5 kDa to about 10 kDa, from about 5 kDa to about 9 kDa, from about 5 kDa to about 8 kDa, from about 5 kDa to about 7 kDa, from about 5 kDa to about 6 kDa, from about 6 kDa to about 50 kDa, from about 6 kDa to about 40 kDa, from about 6 kDa to about 30 kDa, from about 6 kDa to about 20 kDa, from about 6 kDa to about 10 kDa, from about 6 kDa to about 9 kDa, from about 6 kDa to about 8 kDa, from about 6 kDa to about 7 kDa, from about 7 kDa to about 50 kDa, from about 7 kDa to about 40 kDa, from about 7 kDa to about 30 kDa, from about 7 kDa to about 20 kDa, from about 7 kDa to about 10 kDa, from about 7 kDa to about 9 kDa, from about 7 kDa to about 8 kDa, from about 8 kDa to about 50 kDa, from about 8 kDa to about 40 kDa, from about 8 kDa to about 30 kDa, from about 8 kDa to about 20 kDa, from about 8 kDa to about 10 kDa, from about 8 kDa to about 9 kDa, from about 9 kDa to about 50 kDa, from about 9 kDa to about 40 kDa, from about 9 kDa to about 30 kDa, from about 9 kDa to about 20 kDa, from about 9 kDa to about 10 kDa, from about 10 kDa to about 50 kDa, from about 10 kDa to about 40 kDa, from about 10 kDa to about 30 kDa, from about 10 kDa to about 20 kDa, from about 20 kDa to about 50 kDa, from about 20 kDa to about 40 kDa, from about 20 kDa to about 30 kDa, from about 30 kDa to about 50 kDa, from about 30 kDa to about 40 kDa, or from about 40 kDa to about 50 kDa.

In certain embodiments, the oxidized dextran has a Mn of from about 4 kDa to about 166 kDa. In certain embodiments, the oxidized dextran has a Mn of from about 4 kDa to about 45 kDa. In certain embodiments, the oxidized dextran has a Mn of from about 4 kDa to about 6 kDa, from about 4 kDa to about 7 kDa, or from about 5 kDa to about 10 kDa.

In certain embodiments, the oxidized dextran has a polydispersity index (PDI) of from about 1.8 (Mw/Mn) to about 5.0 (Mw/Mn), from about 1.8 (Mw/Mn) to about 6.0 (Mw/Mn), from about 2.0 (Mw/Mn) to about 6.0 (Mw/Mn), from about 2.0 (Mw/Mn) to about 4.0 (Mw/Mn), from about 2.0 (Mw/Mn) to about 3.8 (Mw/Mn), from about 2.0 (Mw/Mn) to about 3.6 (Mw/Mn), from about 2.0 (Mw/Mn) to about 3.4 (Mw/Mn), from about 2.0 (Mw/Mn) to about 3.2 (Mw/Mn), from about 2.0 (Mw/Mn) to about 3.0 (Mw/Mn), from about 2.0 (Mw/Mn) to about 2.8 (Mw/Mn), from about 2.0 (Mw/Mn) to about 2.6 (Mw/Mn), from about 2.0 (Mw/Mn) to about 2.4 (Mw/Mn), from about 2.0 (Mw/Mn) to about 2.2 (Mw/Mn), from about 2.2 (Mw/Mn) to about 4.0 (Mw/Mn), from about 2.2 (Mw/Mn) to about 3.8 (Mw/Mn), from about 2.2 (Mw/Mn) to about 3.6 (Mw/Mn), from about 2.2 (Mw/Mn) to about 3.4 (Mw/Mn), from about 2.2 (Mw/Mn) to about 3.2 (Mw/Mn), from about 2.2 (Mw/Mn) to about 3.0 (Mw/Mn), from about 2.2 (Mw/Mn) to about 2.8 (Mw/Mn), from about 2.2 (Mw/Mn) to about 2.6 (Mw/Mn), from about 2.2 (Mw/Mn) to about 2.4 (Mw/Mn), from about 2.6 (Mw/Mn) to about 4.0 (Mw/Mn), from about 2.6 (Mw/Mn) to about 3.8 (Mw/Mn), from about 2.6 (Mw/Mn) to about 3.6 (Mw/Mn), from about 2.6 (Mw/Mn) to about 3.4 (Mw/Mn), from about 2.6 (Mw/Mn) to about 3.2 (Mw/Mn), from about 2.6 (Mw/Mn) to about 3.0 (Mw/Mn), from about 2.6 (Mw/Mn) to about 2.8 (Mw/Mn), from about 2.8 (Mw/Mn) to about 4.0 (Mw/Mn), from about 2.8 (Mw/Mn) to about 3.8 (Mw/Mn), from about 2.8 (Mw/Mn) to about 3.6 (Mw/Mn), from about 2.8 (Mw/Mn) to about 3.4 (Mw/Mn), from about 2.8 (Mw/Mn) to about 3.2 (Mw/Mn), from about 2.8 (Mw/Mn) to about 3.0 (Mw/Mn), from about 3.0 (Mw/Mn) to about 4.0 (Mw/Mn), from about 3.0 (Mw/Mn) to about 3.8 (Mw/Mn), from about 3.0 (Mw/Mn) to about 3.6 (Mw/Mn), from about 3.0 (Mw/Mn) to about 3.4 (Mw/Mn), from about 3.0 (Mw/Mn) to about 3.2 (Mw/Mn), from about 3.2 (Mw/Mn) to about 4.0 (Mw/Mn), from about 3.2 (Mw/Mn) to about 3.8 (Mw/Mn), from about 3.2 (Mw/Mn) to about 3.6 (Mw/Mn), from about 3.2 (Mw/Mn) to about 3.4 (Mw/Mn), from about 3.4 (Mw/Mn) to about 4.0 (Mw/Mn), from about 3.4 (Mw/Mn) to about 3.8 (Mw/Mn), from about 3.4 (Mw/Mn) to about 3.6 (Mw/Mn), from about 3.6 (Mw/Mn) to about 4.0 (Mw/Mn), from about 3.6 (Mw/Mn) to about 3.8 (Mw/Mn), or from about 3.8 (Mw/Mn) to about 4.0 (Mw/Mn).

In certain embodiments, the oxidized dextran has a polydispersity index (PDI) of from about 1.8 (Mw/Mn) to about 6.0 (Mw/Mn). In certain embodiments, the oxidized dextran has a polydispersity index (PDI) of from about 2.0 (Mw/Mn) to about 4.0 (Mw/Mn). In certain embodiments, the oxidized dextran has a polydispersity index (PDI) of from about 2.8 (Mw/Mn) to about 3.4 (Mw/Mn), from about 3.2 (Mw/Mn) to about 3.6 (Mw/Mn), or from about 3.4 (Mw/Mn) to about 4.0 (Mw/Mn).

In certain embodiments, the oxidized dextran has a Mz of from about 15 kDa to about 500 kDa, from about 20 kDa to about 450 kDa, from about 20 kDa to about 400 kDa, from about 20 kDa to about 300 kDa, from about 20 kDa to about 200 kDa, from about 20 kDa to about 100 kDa, from about 20 kDa to about 50 kDa, from about 20 kDa to about 45 kDa, from about 20 kDa to about 40 kDa, from about 20 kDa to about 35 kDa, from about 20 kDa to about 30 kDa, from about 20 kDa to about 25 kDa, from about 25 kDa to about 450 kDa, from about 25 kDa to about 400 kDa, from about 25 kDa to about 300 kDa, from about 25 kDa to about 200 kDa, from about 25 kDa to about 100 kDa, from about 25 kDa to about 50 kDa, from about 25 kDa to about 45 kDa, from about 25 kDa to about 40 kDa, from about 25 kDa to about 35 kDa, from about 25 kDa to about 30 kDa, from about 30 kDa to about 450 kDa, from about 30 kDa to about 400 kDa, from about 30 kDa to about 300 kDa, from about 30 kDa to about 200 kDa, from about 30 kDa to about 100 kDa, from about 30 kDa to about 50 kDa, from about 30 kDa to about 45 kDa, from about 30 kDa to about 40 kDa, from about 30 kDa to about 35 kDa, from about 35 kDa to about 450 kDa, from about 35 kDa to about 400 kDa, from about 35 kDa to about 300 kDa, from about 35 kDa to about 200 kDa, from about 35 kDa to about 100 kDa, from about 35 kDa to about 50 kDa, from about 35 kDa to about 45 kDa, from about 35 kDa to about 40 kDa, from about 40 kDa to about 450 kDa, from about 40 kDa to about 400 kDa, from about 40 kDa to about 300 kDa, from about 40 kDa to about 200 kDa, from about 40 kDa to about 100 kDa, from about 40 kDa to about 50 kDa, from about 40 kDa to about 45 kDa, from about 45 kDa to about 450 kDa, from about 45 kDa to about 400 kDa, from about 45 kDa to about 300 kDa, from about 45 kDa to about 200 kDa, from about 45 kDa to about 100 kDa, from about 45 kDa to about 50 kDa, from about 50 kDa to about 450 kDa, from about 50 kDa to about 400 kDa, from about 50 kDa to about 300 kDa, from about 50 kDa to about 200 kDa, from about 50 kDa to about 100 kDa, from about 100 kDa to about 450 kDa, from about 100 kDa to about 400 kDa, from about 100 kDa to about 300 kDa, from about 100 kDa to about 200 kDa, from about 200 kDa to about 450 kDa, 200 kDa to about 400 kDa, from about 200 kDa to about 300 kDa, from about 300 kDa to about 450 kDa, from about 300 kDa to about 400 kDa, or from about 400 kDa to about 450 kDa.

In certain embodiments, the oxidized dextran has a Mz of from about 15 kDa to about 500 kDa. In certain embodiments, the oxidized dextran has a Mz of from about 20 kDa to about 450 kDa. In certain embodiments, the oxidized dextran has a Mz of from about 20 kDa to about 35 kDa, about 30 kDa to about 45 kDa or about 40 kDa to about 100 kDa.

In certain embodiments, the oxidized dextran has a polydispersity index (PDI) of from about 1.5 (Mz/Mw) to about 6.0 (Mz/Mw), from about 1.5 (Mz/Mw) to about 5.0 (Mz/Mw), from about 1.5 (Mz/Mw) to about 4.0 (Mz/Mw), from about 1.5 (Mz/Mw) to about 3.5 (Mz/Mw), from about 1.5 (Mz/Mw) to about 3.0 (Mz/Mw), from about 1.5 (Mz/Mw) to about 2.5 (Mz/Mw), from about 1.5 (Mz/Mw) to about 2.0 (Mz/Mw), from about 2.0 (Mz/Mw) to about 5.0 (Mz/Mw), from about 2.0 (Mz/Mw) to about 4.0 (Mz/Mw), from about 2.0 (Mz/Mw) to about 3.5 (Mz/Mw), from about 2.0 (Mz/Mw) to about 3.0 (Mz/Mw), from about 2.0 (Mz/Mw) to about 2.5 (Mz/Mw), from about 2.5 (Mz/Mw) to about 5.0 (Mz/Mw), from about 2.5 (Mz/Mw) to about 4.0 (Mz/Mw), from about 2.5 (Mz/Mw) to about 3.5 (Mz/Mw), from about 2.5 (Mz/Mw) to about 3.0 (Mz/Mw), from about 3.0 (Mz/Mw) to about 5.0 (Mz/Mw), from about 3.0 (Mz/Mw) to about 4.0 (Mz/Mw), from about 3.0 (Mz/Mw) to about 3.5 (Mz/Mw), from about 3.5 (Mz/Mw) to about 5.0 (Mz/Mw), from about 3.5 (Mz/Mw) to about 4.0 (Mz/Mw), or from about 4.0 (Mz/Mw) to about 5.0 (Mz/Mw).

In certain embodiments, the oxidized dextran has a polydispersity index (PDI) of from about 1.5 (Mz/Mw) to about 6.0 (Mz/Mw). In certain embodiments, the oxidized dextran has a polydispersity index (PDI) of from about 1.5 (Mz/Mw) to about 5.0 (Mz/Mw). In certain embodiments, the oxidized dextran has a polydispersity index (PDI) of from about 1.5 (Mz/Mw) to about 2.0 (Mz/Mw), about 1.5 (Mz/Mw) to about 2.5 (Mz/Mw) or about 2.0 (Mz/Mw) to about 4.0 (Mz/Mw).

In certain embodiments, the oxidized dextran comprises a total amount of aldehyde groups of from about 0.5 to about 2.0, from about 0.5 to about 1.0, from about 0.6 to about 0.9, from about 0.6 to about 0.8, from about 0.6 to about 0.7, from about 0.7 to about 1.8, from about 0.7 to about 1.6, from about 0.7 to about 1.4, from about 0.7 to about 1.2, from about 0.7 to about 1.0, from about 0.7 to about 0.9, from about 0.7 to about 0.8, from about 0.8 to about 1.8, from about 0.8 to about 1.6, from about 0.8 to about 1.4, from about 0.8 to about 1.2, from about 0.8 to about 1.0, from about 0.8 to about 0.9, from about 0.9 to about 1.8, from about 0.9 to about 1.6, from about 0.9 to about 1.4, from about 0.9 to about 1.2, from about 0.9 to about 1.0, from about 1.0 to about 1.8, from about 1.0 to about 1.6, from about 1.0 to about 1.4, from about 1.0 to about 1.2, from about 1.2 to about 1.8, from about 1.2 to about 1.6, from about 1.2 to about 1.4, from about 1.4 to about 1.8, from about 1.4 to about 1.6, or from about 1.4 to about 1.8 mol/mol oxidized dextran. In certain embodiments, the oxidized dextran comprises a total amount of aldehyde groups of from about 0.5 to about 2.0 mol/mol oxidized dextran. In certain embodiments, the oxidized dextran comprises a total amount of aldehyde groups of from about 0.6 to about 0.9 mol/mol oxidized dextran. In certain embodiments, the oxidized dextran comprises a total amount of aldehyde groups of from about 0.6 to about 0.8, from about 0.7 to about 0.9, or from about 0.8 to about 1.4 mol/mol oxidized dextran.

In certain embodiments, the oxidized dextran comprises a total amount of primary aldehyde groups of from about 0.35 to about 2.0, about 0.35 to about 1.0, about 0.35 to about 0.7, about 0.35 to about 0.6, about 0.35 to about 0.55, about 0.35 to about 0.5, about 0.35 to about 0.45, about 0.35 to about 0.4, about 0.4 to about 1.5, about 0.4 to about 1.0, about 0.4 to about 0.6, about 0.4 to about 0.55, about 0.4 to about 0.5, about 0.4 to about 0.45, about 0.45 to about 1.5, about 0.45 to about 1.0, about 0.45 to about 0.7, about 0.45 to about 0.6, about 0.45 to about 0.55, about 0.45 to about 0.5, about 0.5 to about 1.5, about 0.5 to about 1.0, about 0.5 to about 0.7, about 0.5 to about 0.6, about 0.5 to about 0.55, about 0.55 to about 1.5, about 0.55 to about 1.0, about 0.55 to about 0.7, about 0.55 to about 0.6, about 0.6 to about 1.5, about 0.6 to about 1.0, about 0.6 to about 0.7, about 0.7 to about 1.5, about 0.7 to about 1.0, or about 1.0 to about 1.5 mol/mol oxidized dextran. In certain embodiments, the oxidized dextran comprises a total amount of primary aldehyde groups of from about 0.35 to about 2.0 mol/mol oxidized dextran. In certain embodiments, the oxidized dextran comprises a total amount of primary aldehyde groups of from about 0.35 to about 0.7 mol/mol oxidized dextran. In certain embodiments, the oxidized dextran comprises a total amount of primary aldehyde groups of from about 0.4 to about 0.55, from about 0.45 to about 0.6, or from about 0.55 to about 0.65 mol/mol oxidized dextran.

In certain embodiments, the oxidized dextran comprises a total amount of secondary aldehyde groups of from about 0.0 to about 1.3, from about 0.1 to about 1.0, from about 0.1 to about 0.7, from about 0.1 to about 0.5, from about 0.1 to about 0.4, from about 0.1 to about 0.3, from about 0.1 to about 0.2, from about 0.2 to about 1.0, from about 0.2 to about 0.7, from about 0.2 to about 0.5, from about 0.2 to about 0.4, from about 0.2 to about 0.3, from about 0.3 to about 1.0, from about 0.3 to about 0.7, from about 0.3 to about 0.5, from about 0.3 to about 0.4, from about 0.4 to about 1.0, from about 0.4 to about 0.7, from about 0.4 to about 0.5, from about 0.5 to about 1.0, from about 0.5 to about 0.7, or from about 0.7 to about 1.0 mol/mol oxidized dextran. In certain embodiments, the oxidized dextran comprises a total amount of secondary aldehyde groups of from about 0.0 to about 1.3 mol/mol oxidized dextran. In certain embodiments, the oxidized dextran comprises a total amount of secondary aldehyde groups of from about 0.1 to about 0.3 mol/mol oxidized dextran. In certain embodiments, the oxidized dextran comprises a total amount of secondary aldehyde groups of from about 0.1 to about 0.3, about 0.2 to about 0.3 or about 0.2 to about 0.5 mol/mol oxidized dextran.

In certain embodiments, the ratio of primary aldehyde groups to secondary aldehyde groups is from about 1.8 to about 6.0, from about 1.8 to about 4.0, from about 1.8 to about 3.5, from about 1.8 to about 3.25, from about 1.8 to about 3.0, from about 1.8 to about 2.75, from about 1.8 to about 2.5, from about 1.8 to about 2.25, from about 1.8 to about 2.0, from about 2.0 to about 3.5, from about 2.0 to about 3.25, from about 2.0 to about 3.0, from about 2.0 to about 2.75, from about 2.0 to about 2.5, from about 2.0 to about 2.25, from about 2.25 to about 3.5, from about 2.25 to about 3.25, from about 2.25 to about 3.0, from about 2.25 to about 2.75, from about 2.25 to about 2.5, from about 2.5 to about 3.5, from about 2.5 to about 3.25, from about 2.5 to about 3.0, from about 2.5 to about 2.75, from about 2.75 to about 3.5, from about 2.75 to about 3.25, from about 2.75 to about 3.0, from about 3.0 to about 3.5, from about 3.0 to about 3.25, or from about 3.25 to about 3.5. In certain embodiments, the ratio of primary aldehyde groups to secondary aldehyde groups is from about 1.8 to about 6.0 or from about 1.8 to about 3.5. In certain embodiments, the ratio of primary aldehyde groups to secondary aldehyde groups is from about 1.8 to about 2.0, about 1.8 to about 2.25, or about 2.0 to about 3.25.

In certain embodiments, the degree of oxidation is from about 25% to about 100%, from about 25% to about 90%, from about 25% to about 80%, from about 25% to about 70%, from about 25% to about 60%, from about 30% to about 45%, from about 30% to about 40%, from about 30% to about 35%, from about 35% to about 45%, from about 35% to about 40%. In certain embodiments, the degree of oxidation is from about 25% to about 100% or from about 30% to about 50%. In certain embodiments, the degree of oxidation is from about 30% to about 45%, or about 35% to about 45%.

In certain embodiments, the oxidized dextran composition comprises about 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), about 20% (w/w), about 21% (w/w), about 22% (w/w), about 23% (w/w), about 24% (w/w), or about 25% (w/w) by weight of the total weight of the solution.

In certain embodiments, the oxidized dextran composition comprises from about 1% (w/w) to about 25% (w/w), from about 1% (w/w) to about 20% (w/w), from about 1% (w/w) to about 15% (w/w), from about 1% (w/w) to about 10% (w/w), from about 1% (w/w) to about 9% (w/w), from about 1% (w/w) to about 8% (w/w), from about 1% (w/w) to about 7% (w/w), from about 1% (w/w) to about 6% (w/w), from about 1% (w/w) to about 5% (w/w), from about 1% (w/w) to about 4% (w/w), from about 1% (w/w) to about 3% (w/w), from about 1% (w/w) to about 2% (w/w), from about 2% (w/w) to about 10% (w/w), from about 2% (w/w) to about 9% (w/w), from about 2% (w/w) to about 8% (w/w), from about 2% (w/w) to about 7% (w/w), from about 2% (w/w) to about 6% (w/w), from about 2% (w/w) to about 5% (w/w), from about 2% (w/w) to about 4% (w/w), from about 2% (w/w) to about 3% (w/w), from about 3% (w/w) to about 10% (w/w), from about 3% (w/w) to about 9% (w/w), from about 3% (w/w) to about 8% (w/w), from about 3% (w/w) to about 7% (w/w), from about 3% (w/w) to about 6% (w/w), from about 3% (w/w) to about 5% (w/w), from about 3% (w/w) to about 4% (w/w), from about 4% (w/w) to about 10% (w/w), from about 4% (w/w) to about 9% (w/w), from about 4% (w/w) to about 8% (w/w), from about 4% (w/w) to about 7% (w/w), from about 4% (w/w) to about 6% (w/w), from about 4% (w/w) to about 5% (w/w), from about 5% (w/w) to about 10% (w/w), from about 5% (w/w) to about 9% (w/w), from about 5% (w/w) to about 8% (w/w), from about 5% (w/w) to about 7% (w/w), from about 5% (w/w) to about 6% (w/w), from about 6% (w/w) to about 10% (w/w), from about 6% (w/w) to about 9% (w/w), from about 6% (w/w) to about 8% (w/w), from about 6% (w/w) to about 7% (w/w), from about 7% (w/w) to about 10% (w/w), from about 7% (w/w) to about 9% (w/w), from about 7% (w/w) to about 8% (w/w), from about 8% (w/w) to about 10% (w/w), from about 8% (w/w) to about 9% (w/w), or from about 9% (w/w) to about 10% (w/w) of the oxidized dextran. In certain embodiments, the oxidized dextran composition comprises from about 1% (w/w) to about 25% (w/w) or from about 1% (w/w) to about 10% (w/w) of the oxidized dextran. In certain embodiments, the oxidized dextran composition comprises about 2% (w/w) to about 5% (w/w), about 4% (w/w) to about 7% (w/w), or about 6% (w/w) to about 10% (w/w) of the oxidized dextran.

In certain embodiments, the oxidized dextran composition has a viscosity of from about 1.0 cP to about 2,000 cP, from about 1.0 cP to about 1,000 cP, from about 1.0 cP to about 100 cP, from about 1.0 cP to about 10 cP, from about 1.0 cP to about 9 cP, from about 1.0 cP to about 8 cP, from about 1.0 cP to about 7 cP, from about 1.0 cP to about 6 cP, from about 1.0 cP to about 5 cP, from about 1.0 cP to about 4 cP, from about 1.0 cP to about 3 cP, from about 1.0 cP to about 2 cP, from about 2.0 cP to about 10.0 cP, from about 2.0 cP to about 9.0 cP, from about 2.0 cP to about 8.0 cP, from about 2.0 cP to about 7.0 cP, from about 2.0 cP to about 6.0 cP, from about 2.0 cP to about 5.0 cP, from about 2.0 cP to about 4.0 cP, from about 2.0 cP to about 3.0 cP, from about 3.0 cP to about 10.0 cP, from about 3.0 cP to about 9.0 cP, from about 3.0 cP to about 8.0 cP, from about 3.0 cP to about 7.0 cP, from about 3.0 cP to about 6.0 cP, from about 3.0 cP to about 5.0 cP, from about 3.0 cP to about 4.0 cP, from about 4.0 cP to about 10.0 cP, from about 4.0 cP to about 9.0 cP, from about 4.0 cP to about 8.0 cP, from about 4.0 cP to about 7.0 cP, from about 4.0 cP to about 6.0 cP, from about 4.0 cP to about 5.0 cP, from about 5.0 cP to about 10.0 cP, from about 5.0 cP to about 9.0 cP, from about 5.0 cP to about 8.0 cP, from about 5.0 cP to about 7.0 cP, from about 5.0 cP to about 6.0 cP, from about 6.0 cP to about 10.0 cP, from about 6.0 cP to about 9.0 cP, from about 6.0 cP to about 8.0 cP, from about 6.0 cP to about 7.0 cP, from about 7.0 cP to about 10.0 cP, from about 7.0 cP to about 9.0 cP, from about 7.0 cP to about 8.0 cP, from about 8.0 cP to about 10.0 cP, from about 8.0 cP to about 9.0 cP, or from about 9.0 cP to about 10.0 cP.

In certain embodiments, the oxidized dextran composition has a viscosity of from about 1 cP to about 2,000 cP, or from about 1 cP to about 10 cP. In certain embodiments, the oxidized dextran composition has a viscosity of from about 1.0 cP to about 3.0 cP, about 1.0 cP to about 5.0 cP, or about 3.0 cP to about 9.0 cP.

In certain embodiments, the oxidized dextran composition has a pH of from about 5.0 to about 7.5, from about 5.2 to about 7.5, from about 5.4 to about 7.5, from about 5.6 to about 7.5, from about 5.8 to about 7.5, from about 6.0 to about 7.5, from about 6.2 to about 7.5, from about 6.4 to about 7.5, from about 6.6 to about 7.5, from about 6.8 to about 7.5, from about 7.0 to about 7.5, from about 5.0 to about 7.0, from about 5.0 to about 6.8, from about 5.0 to about 6.6, from about 5.0 to about 6.4, from about 5.0 to about 6.2, from about 5.0 to about 6.0, from about 5.0 to about 5.8, from about 5.0 to about 5.6, from about 5.0 to about 5.4, from about 5.0 to about 5.2, from about 5.2 to about 7.0, from about 5.2 to about 6.8, from about 5.2 to about 6.6, from about 5.2 to about 6.4, from about 5.2 to about 6.2, from about 5.2 to about 6.0, from about 5.2 to about 5.8, from about 5.2 to about 5.6, from about 5.2 to about 5.4, from about 5.4 to about 7.0, from about 5.4 to about 6.8, from about 5.4 to about 6.6, from about 5.4 to about 6.4, from about 5.4 to about 6.2, from about 5.4 to about 6.0, from about 5.4 to about 5.8, from about 5.4 to about 5.6, from about 5.6 to about 7.0, from about 5.6 to about 6.8, from about 5.6 to about 6.6, from about 5.6 to about 6.4, from about 5.6 to about 6.2, from about 5.6 to about 6.0, from about 5.6 to about 5.8, from about 5.8 to about 7.0, from about 5.8 to about 6.8, from about 5.8 to about 6.6, from about 5.8 to about 6.4, from about 5.8 to about 6.2, from about 5.8 to about 6.0, from about 6.0 to about 7.0, from about 6.0 to about 6.8, from about 6.0 to about 6.6, from about 6.0 to about 6.4, from about 6.0 to about 6.2, from about 6.2 to about 7.0, from about 6.2 to about 6.8, from about 6.2 to about 6.6, from about 6.2 to about 6.4, from about 6.4 to about 7.0, from about 6.4 to about 6.8, from about 6.4 to about 6.6, from about 6.6 to about 7.0, from about 6.6 to about 6.8, or from about 6.8 to about 7.0. In certain embodiments, the oxidized dextran composition has a pH of from about 5.0 to about 7.5. In certain embodiments, the oxidized dextran composition has a pH of from about 5.0 to about 6.0, from about 5.0 to about 6.8, or from about 5.6 to about 7.0.

In certain embodiments, the oxidized dextran composition has a conductivity of from about 0.05 (mS/cm) to about 1.7 (mS/cm), from about 0.05 (mS/cm) to about 1.2 (mS/cm), from about 0.05 (mS/cm) to about 0.7 (mS/cm), from about 0.05 (mS/cm) to about 0.5 (mS/cm), from about 0.05 (mS/cm) to about 0.3 (mS/cm), from about 0.05 (mS/cm) to about 0.25 (mS/cm), from about 0.05 (mS/cm) to about 0.2 (mS/cm), from about 0.05 (mS/cm) to about 0.15 (mS/cm), from about 0.05 (mS/cm) to about 0.1 (mS/cm), from about 0.1 (mS/cm) to about 0.7 (mS/cm), from about 0.1 (mS/cm) to about 0.5 (mS/cm), from about 0.1 (mS/cm) to about 0.3 (mS/cm), from about 0.1 (mS/cm) to about 0.25 (mS/cm), from about 0.1 (mS/cm) to about 0.2 (mS/cm), from about 0.1 (mS/cm) to about 0.15 (mS/cm), from about 0.15 (mS/cm) to about 0.7 (mS/cm), from about 0.15 (mS/cm) to about 0.5 (mS/cm), from about 0.15 (mS/cm) to about 0.3 (mS/cm), from about 0.15 (mS/cm) to about 0.25 (mS/cm), from about 0.15 (mS/cm) to about 0.2 (mS/cm), from about 0.2 (mS/cm) to about 0.7 (mS/cm), from about 0.2 (mS/cm) to about 0.5 (mS/cm), from about 0.2 (mS/cm) to about 0.3 (mS/cm), from about 0.2 (mS/cm) to about 0.25 (mS/cm), from about 0.25 (mS/cm) to about 0.7 (mS/cm), from about 0.25 (mS/cm) to about 0.5 (mS/cm), from about 0.25 (mS/cm) to about 0.3 (mS/cm), from about 0.3 (mS/cm) to about 0.7 (mS/cm), from about 0.3 (mS/cm) to about 0.5 (mS/cm), or from about 0.5 (mS/cm) to about 0.7 (mS/cm). In certain embodiments, the oxidized dextran composition has a conductivity of from about 0.05 (mS/cm) to about 1.7 (mS/cm). In certain embodiments, the oxidized dextran composition has a conductivity of from about 0.05 (mS/cm) to about 0.7 (mS/cm). In certain embodiments, the oxidized dextran composition has a conductivity of from about from about 0.1 (mS/cm) to about 0.3 (mS/cm), from about 0.2 (mS/cm) to about 0.5 (mS/cm) or from about 0.3 (mS/cm) to about 0.7 (mS/cm).

In certain embodiments, the oxidized dextran has two or more properties selected from a Mw of from about 10 kDa to about 300 kDa, a Mn of from about 4 kDa to about 166 kDa, a PDI of from about 1.8 to about 6.0 (Mw/Mn), a total amount of aldehyde groups of from about 0.5 to about 2.0 mol aldehydes/mol oxidized dextran, a total amount of primary aldehydes of from about 0.35 to about 2.0 mol aldehydes/mol oxidized dextran, a total amount of secondary aldehydes of from about 0.0 to about 1.3 mol aldehydes/mol oxidized dextran, a ratio of primary aldehyde groups to secondary aldehyde groups from about 1.6 to about 6.0, a degree of oxidation from about 25% to about 100%.

In certain embodiments, the oxidized dextran composition comprises a plurality (e.g., 2, 3, 4, 5, 6, 7, 8, 9, 10, 11, or 12) or all of the following features: (i) a Mw of from about 15 kDa to about 90 kDa, (ii) a Mn of from about 4 kDa to about 45 kDa, (iii) a Mz of from about 22 kDa to about 450 kDa, (iv) a PDI (Mw/Mn) of from about 2.0 to about 4.0, (v) a PDI (Mz/Mw) of from about 1.5 to about 5.0, (vi) a mole fraction of the monomer of formula (V) of from about 0.5 to about 0.7, (vii) a mole fraction of the monomer of formula (VI) and/or the monomer of formula (VII) of from about 0.15 to about 0.35, (viii) a mole fraction of the monomer of formula (VIII) of from about 0.1 to about 0.16, (ix) a total amount of aldehyde groups of from about 0.65 to about 0.9 mol aldehydes/mol oxidized dextran, (x) a total amount of primary aldehyde groups of from about 0.38 to about 0.7 mol aldehydes/mol oxidized dextran, (xi) a total amount of secondary aldehyde groups of from about 0.1 to about 0.31 mol aldehydes/mol oxidized dextran, (xii) a ratio of primary aldehyde groups to secondary aldehyde groups of from about 1.8 to about 3.5, and (xiii) a degree of oxidation of from about 32% to about 45%.

In certain embodiments, the oxidized dextran composition comprises a plurality (e.g., 2, 3, 4, 5, 6, 7, 8, 9, 10, 11, 12, 13, 14, 15, or 16) or all of the following features: (i) a Mw of from about 15 kDa to about 90 kDa, (ii) a Mn of from about 4 kDa to about 45 kDa, (iii) a Mz of from about 22 kDa to about 450 kDa, (iv) a PDI (Mw/Mn) of from about 2.0 to about 4.0, (v) a PDI (Mz/Mw) of from about 1.5 to about 5.0, (vi) a mole fraction of the monomer of formula (V) of from about 0.5 to about 0.7, (vii) a mole fraction of the monomer of formula (VI) and/or the monomer of formula (VII) of from about 0.15 to about 0.35, (viii) a mole fraction of the monomer of formula (VIII) of from about 0.1 to about 0.16, (ix) a total amount of aldehyde groups of from about 0.65 to about 0.9 mol aldehydes/mol oxidized dextran, (x) a total amount of primary aldehyde groups of from about 0.38 to about 0.7 mol aldehydes/mol oxidized dextran, (xi) a total amount of secondary aldehyde groups of from about 0.1 to about 0.31 mol aldehydes/mol oxidized dextran, (xii) a ratio of primary aldehyde groups to secondary aldehyde groups of from about 1.8 to about 3.5, (xiii) a degree of oxidation of from about 32% to about 45%, (xiv) a concentration of the acrylated chitosan in an aqueous medium or from about 1% (w/w) to about 10% (w/w), (xv) a viscosity of from about 1 cP to about 10 cP, (xvi) a pH of from about 5.0 to about 7.5, and (xvii) a conductivity of from about 0.05 mS/cm to about 0.7 mS/cm.

V Methods of Making Oxidized Dextran Compositions

Dextran is an α-D-1,6-glucose-linked glucan with side chains 1-3 linked to the backbone units of the dextran biopolymer.

One aspect of the invention provides methods of preparing oxidized dextran compositions. In various embodiments, the methods generally include:
 (a) contacting a raw dextran material with an oxidizing agent to form an oxidized dextran intermediate; and
 (b) purifying the oxidized dextran intermediate to produce an oxidized dextran composition of the present invention.

In certain embodiments, during step (a), the raw dextran material has a Mw of from about 50 kDa to about 2,000 kDa, from about 50 kDa to about 1,000 kDa, from about 50 kDa to about 500 kDa, from about 50 kDa to about 400 kDa, from about 60 kDa to about 2,000 kDa, from about 60 kDa to about 1,000 kDa, from about 50 kDa to about 500 kDa, from about 60 kDa to about 400 kDa, from about 60 kDa to about 300 kDa, from about 60 kDa to about 200 kDa, from about 60 kDa to about 100 kDa, from about 60 kDa to about 90 kDa, from about 60 kDa to about 80 kDa, from about 60 kDa to about 70 kDa, from about 70 kDa to about 400 kDa, from about 70 kDa to about 300 kDa, from about 70 kDa to about 200 kDa, from about 70 kDa to about 100 kDa, from about 70 kDa to about 90 kDa, from about 70 kDa to about 80 kDa, from about 80 kDa to about 400 kDa, from about 80 kDa to about 300 kDa, from about 80 kDa to about 200 kDa, from about 80 kDa to about 100 kDa, from about 80 kDa to about 90 kDa, from about 90 kDa to about 400 kDa, from about 90 kDa to about 300 kDa, from about 90 kDa to about 200 kDa, from about 90 kDa to about 100 kDa, from about 100 kDa to about 400 kDa, from about 100 kDa to about 300 kDa, from about 100 kDa to about 200 kDa, from about 200 kDa to about 400 kDa, from about 200 kDa to about 300 kDa, or from about 300 kDa to about 400 kDa. In certain embodiments, during step (a), the raw dextran material has a Mw of from about 50 kDa to about 2,000 kDa. In certain embodiments, during step (a), the raw dextran material has a Mw of from about 60 kDa to about 400 kDa. In certain embodiments, during step (a), the raw dextran material has a Mw of from about 60 kDa to about 100 kDa, about 80 kDa to about 200 kDa, or about 100 kDa to about 400 kDa.

In certain embodiments, during step (a), the raw dextran material has a Mn of from about 15 kDa to about 500 kDa, from about 15 kDa to about 250 kDa, from about 25 kDa to about 500 kDa, from about 25 kDa to about 250 kDa, from about 25 kDa to about 200 kDa, from about 25 kDa to about 160 kDa, from about 25 kDa to about 140 kDa, from about 25 kDa to about 120 kDa, from about 25 kDa to about 100 kDa, from about 25 kDa to about 90 kDa, from about 25 kDa to about 80 kDa, from about 25 kDa to about 70 kDa, from about 25 kDa to about 60 kDa, from about 25 kDa to about 50 kDa, from about 25 kDa to about 40 kDa, from about 25 kDa to about 35 kDa, from about 25 kDa to about 30 kDa, from about 30 kDa to about 250 kDa, from about 30 kDa to about 200 kDa, from about 30 kDa to about 160 kDa, from about 30 kDa to about 140 kDa, from about 30 kDa to about 120 kDa, from about 30 kDa to about 100 kDa, from about 30 kDa to about 90 kDa, from about 30 kDa to about 80 kDa, from about 30 kDa to about 70 kDa, from about 30 kDa to about 60 kDa, from about 30 kDa to about 50 kDa, from about 30 kDa to about 40 kDa, from about 30 kDa to about 35 kDa, from about 35 kDa to about 250 kDa, from about 35 kDa to about 200 kDa, from about 35 kDa to about 160 kDa, from about 35 kDa to about 140 kDa, from about 35 kDa to about 120 kDa, from about 35 kDa to about 100 kDa, from about 35 kDa to about 90 kDa, from about 35 kDa to about 80 kDa, from about 35 kDa to about 70 kDa, from about 35 kDa to about 60 kDa, from about 35 kDa to about 50 kDa, from about 35 kDa to about 40 kDa, from about 40 kDa to about 250 kDa, from about 40 kDa to about 200 kDa, from about 40 kDa to about 160 kDa, from about 40 kDa to about 140 kDa, from about 40 kDa to about 120 kDa, from about 40 kDa to about 100 kDa, from about 40 kDa to about 90 kDa, from about 40 kDa to about 80 kDa, from about 40 kDa to about 70 kDa, from about 40 kDa to about 60 kDa, from about 40 kDa to about 50 kDa, from about 50 kDa to about 250 kDa, from about 50 kDa to about 200 kDa, from about 50 kDa to about 160 kDa, from about 50 kDa to about 150 kDa, from about 50 kDa to about 120 kDa, from about 50 kDa to about 100 kDa, from about 50 kDa to about 90 kDa, from about 50 kDa to about 80 kDa, from about 50 kDa to about 70 kDa, or from about 50 kDa to about 60 kDa.

In certain embodiments, during step (a), the raw dextran material has a Mn of from about 15 kDa to about 500 kDa. In certain embodiments, during step (a), the raw dextran material has a Mn of from about 25 kDa to about 250 kDa. In certain embodiments, during step (a), the raw dextran material has a Mn of from about 25 kDa to about 120 kDa, from about 40 kDa to about 140 kDa, or from about 80 kDa to about 200 kDa.

In certain embodiments, during step (a), the raw dextran material has a PDI of from about 1.3 (Mw/Mn) to about 5.0 (Mw/Mn), from about 1.4 (Mw/Mn) to about 5.0 (Mw/Mn), from about 1.4 (Mw/Mn) to about 4.0 (Mw/Mn), from about 1.4 (Mw/Mn) to about 3.0 (Mw/Mn), from about 1.5 (Mw/Mn) to about 5.0 (Mw/Mn), from about 1.5 (Mw/Mn) to about 4.0 (Mw/Mn), from about 1.5 (Mw/Mn) to about 3.0 (Mw/Mn), from about 1.5 (Mw/Mn) to about 2.5 (Mw/Mn), from about 1.5 (Mw/Mn) to about 2.0 (Mw/Mn), from about 1.5 (Mw/Mn) to about 1.9 (Mw/Mn), from about 1.5 (Mw/Mn) to about 1.7 (Mw/Mn), from about 1.7 (Mw/Mn) to about 3.0 (Mw/Mn), from about 1.7 (Mw/Mn) to about 2.5 (Mw/Mn), from about 1.7 (Mw/Mn) to about 2.0 (Mw/Mn), from about 1.7 (Mw/Mn) to about 1.9 (Mw/Mn), from about 1.9 (Mw/Mn) to about 3.0 (Mw/Mn), from about 1.9 (Mw/Mn) to about 2.5 (Mw/Mn), or from about 1.9 (Mw/Mn) to about 2.0 (Mw/Mn).

In certain embodiments, during step (a), the raw dextran material has a PDI of from about 1.4 (Mw/Mn) to about 5.0 (Mw/Mn). In certain embodiments, during step (a), the raw dextran material has a PDI of from about 1.5 (Mw/Mn) to about 3.0 (Mw/Mn). In certain embodiments, during step (a), the raw dextran material has a PDI of from about 1.5 (Mw/Mn) to about 2.0 (Mw/Mn), about 1.5 (Mw/Mn) to about 2.5 (Mw/Mn), or about 1.9 (Mw/Mn) to about 3.0 (Mw/Mn).

In certain embodiments, during step (a), the raw dextran material has a Mz of from about 250 kDa to about 5,000 kDa, from about 250 kDa to about 4,000 kDa, from about 250 kDa to about 3,000 kDa, from about 250 kDa to about 2,000 kDa, from about 300 kDa to about 5,000 kDa, from about 300 kDa to about 4,000 kDa, from about 300 kDa to about 3,000 kDa, about 300 kDa to about 2,000 kDa, from about 300 kDa to about 1,500 kDa, from about 300 kDa to about 1,000 kDa, from about 300 kDa to about 750 kDa, from about 300 kDa to about 500 kDa, from about 300 kDa to about 450 kDa, from about 300 kDa to about 400 kDa, from about 300 kDa to about 350 kDa, from about 350 kDa to about 2,000 kDa, from about 350 kDa to about 1,500 kDa, from about 350 kDa to about 1,000 kDa, from about 350 kDa to about 750 kDa, from about 350 kDa to about 500 kDa, from about 350 kDa to about 450 kDa, from about 350 kDa to about 400 kDa, from about 400 kDa to about 2,000 kDa, from about 400 kDa to about 1,500 kDa, from about 400 kDa to about 1,000 kDa, from about 400 kDa to about 750 kDa, from about 400 kDa to about 500 kDa, from about 400 kDa to about 450 kDa, from about 450 kDa to about 2,000 kDa, from about 450 kDa to about 1,500 kDa, from about 450 kDa to about 1,000 kDa, from about 450 kDa to about 750 kDa, from about 450 kDa to about 500 kDa, from about 500 kDa to about 2,000 kDa, from about 500 kDa to about 1,500 kDa, from about 500 kDa to about 1,000 kDa, from about 500 kDa to about 750 kDa, from about 750 kDa to about 2,000 kDa, from about 750 kDa to about 1,500 kDa, from about 750 kDa to about 1,000 kDa, from about 1,000 kDa to about 2,000 kDa, from about 1,000 kDa to about 1,500 kDa, or from about 1,500 kDa to about 2,000 kDa.

In certain embodiments, during step (a), the raw dextran material has a Mz of from about 250 kDa to about 5,000 kDa. In certain embodiments, during step (a), the raw dextran material has a Mz of from about 300 kDa to about 2,000 kDa. In certain embodiments, during step (a), the raw dextran material has a Mz of from about 300 kDa to about 1,000 kDa, from about 350 kDa to about 1,500 kDa, or from about 500 kDa to about 2,000 kDa.

In certain embodiments, during step (a), the raw dextran material has a PDI of from about 1.4 (Mz/Mw) to about 15.0 (Mz/Mw), from about 1.5 (Mz/Mw) to about 15.0 (Mz/Mw), from about 1.7 (Mz/Mw) to about 15.0 (Mz/Mw), from about 2.0 (Mz/Mw) to about 15.0 (Mz/Mw), from about 3.0 (Mz/Mw) to about 15.0 (Mz/Mw), from about 6.0 (Mz/Mw) to about 15.0 (Mz/Mw), from about 9.0 (Mz/Mw) to about 15.0 (Mz/Mw), from about 12.0 (Mz/Mw) to about 15.0 (Mz/Mw), from about 1.5 (Mz/Mw) to about 12.0 (Mz/Mw), from about 1.5 (Mz/Mw) to about 9.0 (Mz/Mw), from about 1.5 (Mz/Mw) to about 6.0 (Mz/Mw), from about 1.5 (Mz/Mw) to about 3.0 (Mz/Mw), from about 1.5 (Mz/Mw) to about 2.0 (Mz/Mw), from about 1.5 (Mz/Mw) to about 1.7 (Mz/Mw), from about 1.7 (Mz/Mw) to about 12.0 (Mz/Mw), from about 1.7 (Mz/Mw) to about 9.0 (Mz/Mw), from about 1.7 (Mz/Mw) to about 6.0 (Mz/Mw), from about 1.7 (Mz/Mw) to about 3.0 (Mz/Mw), from about 1.7 (Mz/Mw) to about 2.0 (Mz/Mw), from about 2.0 (Mz/Mw) to about 12.0 (Mz/Mw), from about 2.0 (Mz/Mw) to about 9.0 (Mz/Mw), from about 2.0 (Mz/Mw) to about 6.0 (Mz/Mw), from about 2.0 (Mz/Mw) to about 3.0 (Mz/Mw), from about 3.0 (Mz/Mw) to about 12.0 (Mz/Mw), from about 3.0 (Mz/Mw) to about 9.0 (Mz/Mw), from about 3.0 (Mz/Mw) to about 6.0 (Mz/Mw), from about 6.0 (Mz/Mw) to about 12.0 (Mz/Mw), from about 6.0 (Mz/Mw) to about 9.0 (Mz/Mw), or from about 9.0 (Mz/Mw) to about 12.0 (Mz/Mw).

In certain embodiments, during step (a), the raw dextran material has a PDI of from about 1.4 (Mz/Mw) to about 15.0 (Mz/Mw). In certain embodiments, during step (a), the raw dextran material has a PDI of from about 1.5 (Mz/Mw) to about 15.0 (Mz/Mw). In certain embodiments, during step (a), the raw dextran material has a PDI of from about 1.5 (Mz/Mw) to about 9.0 (Mz/Mw), about 1.5 (Mz/Mw) to about 12.0 (Mz/Mw), or about 6.0 (Mz/Mw) to about 15.0 (Mz/Mw).

In certain embodiments, the raw dextran material comprises two or more of the features selected from an Mw of from about 50 kDa to about 2,000 kDa, an Mn of from about 15 kDa to about 500 kDa, a PDI of from about 1.4 to about 5.0 (Mw/Mn), a Mz of from about 250 kDa to about 5,000 kDa, and a PDI pf from about 1.4 to about 15.0 (Mz/Mw).

In certain embodiments, during step (a), the raw dextran material is contacted with the oxidizing agent at a temperature of about 0° C., about 5° C., about 10° C., about 15° C., about 20° C., about 25° C., about 30° C., about 35° C., about 40° C., about 45° C., or about 50° C. In certain embodiments, in step (a), the raw dextran material is contacted with the oxidizing agent at a temperature from about 0° C. to about 50° C., from about 10° C. to about 50° C., from about 20° C. to about 50° C., from about 30° C. to about 50° C., from about 40° C. to about 50° C., from about 10° C. to about 40° C., from about 10° C. to about 30° C., from about 10° C. to about 20° C., from about 20° C. to about 40° C., from about 20° C. to about 30° C., or from about 30° C. to about 40° C. In certain embodiments, in step (a), the raw dextran material is contacted with the oxidizing agent at a temperature from about 0° C. to about 50° C.

In certain embodiments, during step (a), the oxidizing agent is a periodate salt. In certain embodiments, the periodate salt is selected from the group consisting of sodium periodate or potassium periodate.

In certain embodiments, during step (b), the oxidized dextran is purified using a method selected from the group consisting of dialysis, gel filtration chromatography, stirred cell filtration, tangential flow filtration, and combinations thereof.

In certain embodiments, the yield of oxidized dextran obtained following step (c) is from about 75% to about 100%, from about 80% to about 100%, from about 85% to about 100%, from about 90% to about 100%, from about 95% to about 100%, from about 75% to about 95%, from about 75% to about 90%, from about 75% to about 85%, from about 75% to about 80%, from about 80% to about 95%, from about 80% to about 90%, from about 80% to about 85%, from about 85% to about 95%, from about 85% to about 90%, or from about 90% to about 95%. In certain embodiments, the yield of acrylated chitosan obtained following step (c) is from about 75% to about 95%.

In certain embodiments, the method further comprising the step of precipitating the oxidized dextran composition to provide a solid. In certain embodiments, the method further comprising the step of lyophilizing the oxidized dextran composition to provide a solid.

In certain embodiments, the method further comprising the step of dissolving the solid into an aqueous medium to form a solution comprising an amount of the oxidized dextran composition.

In certain embodiments, the amount of the oxidized dextran composition comprises about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight of the total weight of the solution.

In certain embodiments, the amount of the oxidized dextran composition comprises from about 1% to about 25%, from about 1% to about 20%, from about 1% to about 15%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1% to about 2%, from about 2% to about 10%, from about 2% to about 9%, from about 2% to about 8%, from about 2% to about 7%, from about 2% to about 6%, from about 2% to about 5%, from about 2% to about 4%, from about 2% to about 3%, from about 3% to about 10%, from about 3% to about 9%, from about 3% to about 8%, from about 3% to about 7%, from about 3% to about 6%, from about 3% to about 5%, from about 3% to about 4%, from about 4% to about 10%, from about 4% to about 9%, from about 4% to about 8%, from about 4% to about 7%, from about 4% to about 6%, from about 4% to about 5%, from about 5% to about 10%, from about 5% to about 9%, from about 5% to about 8%, from about 5% to about 7%, from about 5% to about 6%, from about 6% to about 10%, from about 6% to about 9%, from about 6% to about 8%, from about 6% to about 7%, from about 7% to about 10%, from about 7% to about 9%, from about 7% to about 8%, from about 8% to about 10%, from about 8% to about 9%, or from about 9% to about 10% by weight of the total weight of the solution.

In certain embodiments, the amount of the oxidized dextran composition is from about 1% (w/w) to about 25% (w/w). In certain embodiments, the amount of the oxidized dextran composition is from about 1% (w/w) to about 10%

(w/w) by weight of the total weight of the solution. In certain embodiments, the amount of the oxidized dextran composition is from about 2% to about 5%, about 4% to about 7%, or about 6% to about 9%.

In another aspect, provided herein is a method of preparing an oxidized dextran composition comprising:
(a) contacting a raw dextran material with a periodate salt to form an oxidized dextran intermediate, wherein the raw dextran material has a PDI of from about 1.4 to about 5.0; and
(b) purifying the oxidized dextran intermediate to produce an oxidized dextran composition of the present invention.

In certain embodiments, the periodate salt is selected from the group consisting of sodium periodate or potassium periodate.

In certain embodiments, the yield of oxidized dextran obtained following step (c) is from about 75% to about 95%.

In certain embodiments, the method further comprising the step of precipitating the oxidized dextran composition to provide a solid. In certain embodiments, the method further comprising the step of lyophilizing the oxidized dextran composition to provide a solid.

In certain embodiments, the amount of the oxidized dextran composition is from about 1% (w/w) to about 10% (w/w) by weight of the total weight of the solution.

VI Methods of Making Hemostatic Compositions

The hemostatic hydrogels of the present invention represent a three-dimensional dynamic network that forms with reversible covalent bonds. The dynamic network is modulated by a variety of properties including, among other things, the properties of the two precursor compositions of the present invention, namely the acrylated chitosan and oxidized dextran compositions. Without wishing to be bound by theory, it is believed that the formation of the hydrogel composition is a two-step process. In the first step, the acrylated chitosan and oxidized dextran polymer chains intertwine, resulting in the formation of hydrogen bonding between the acrylated chitosan and oxidized dextran chains. In the second step, a Schiff base group forms between the aldehyde groups present in the oxidized dextran and the free amino group of the acrylated chitosan. The localized reaction between one monomer of the oxidized dextran (in its aldehyde form) and one monomer of the acrylated chitosan to link via Schiff base formation is depicted below:

Schiff base formation is a reversible reaction with equilibrium favoring formation of the Schiff base. This reversibility in Schiff base formation may impact the biodegradation of the hydrogel over time. It is contemplated more unreacted aldehydes on the oxidized dextran backbone come in contact with unreacted amines on the acrylated chitosan backbone to form additional Schiff base links, the polymer chains reorient to a more compact hydrogel with a reduced spatial volume that exudes water as it shrinks.

The kinetics of hydrogel formation are important for the function of the hydrogel as a hemostat given, among other things, the desire to rapidly stop blood loss or leakage in tissues of interest. It is believed that the hydrogel compositions of the present invention have three different reaction kinetics occurring concurrently. The initial reaction kinetics of gel formation are considered rapid enough for the hydrogel to adhere to tissue and gain enough cohesive strength and stiffness in a short period of time (e.g., from about 5 to about 30 seconds) to stem the blood flow. During this short period of time, the initial kinetics also forms a trabeculated, non-interconnected pore structure with a large pore size distribution (see, FIGS. 1 and 5). These features contribute to the collection, retention and concentration of platelets and red blood cells (RBCs) within the pore structure of the hydrogel. The surface roughness of this pore structure facilitates platelet adhesion, activation and aggregation (e.g., soft clot or platelet plug) which are the first steps in activating the coagulation cascade (see, FIG. 2). Once the coagulation cascade is triggered, fibrin strands are formed through biochemical pathways. The fibrin strands trap more platelets and red blood cells, thereby forming a stable blood clot. The secondary rate kinetics of additional Schiff base formation appear to be slower and retain the concentrated platelets and RBCs locally to promote coagulation. The lack of swelling in the hydrogel avoids dilution of the platelets and RBCs, as might be observed in other matrices that expand (e.g., gelatin based hemostats, cellulose based hemostats), and results in more effective aggregation and concentration that is required for coagulation. The third rate kinetics relate to the rate of degradation of the hydrogel. This rate is fast enough to allow continuous shrinkage and eventual degradation within a physiologically relevant time frame over days, weeks and months.

The invention provides methods of preparing hemostatic hydrogel compositions. In various embodiments, the meth-

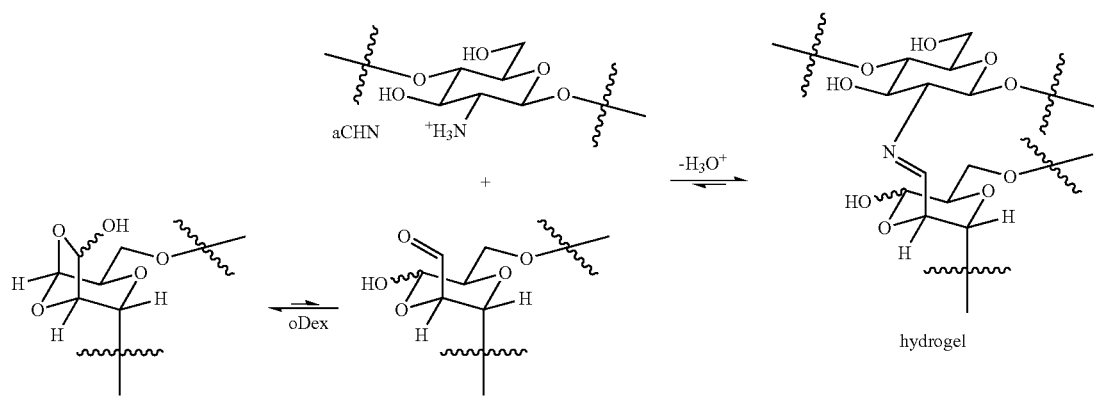 [SMILES: *OCC1OC(*)C2OC1OC2O ; *OC1OC(CO)C(O*)C(O)C1[NH3+] ; *OCC1OC(*)C(C=O)OC1O ; "-H3O+" ; *OCC1OC(*)C(/C=N/C2C(O*)OC(CO)C(O*)C2O)OC1O]

ods generally include contacting an acrylated chitosan composition disclosed herein with an oxidized dextran composition disclosed herein.

In certain embodiments, the ratio of the viscosity of the acrylated chitosan composition to the oxidized chitosan composition ranges from about 50:1 to about 10,000:1, from about 100:1 to about 10,000:1, from about 500:1 to about 10,000:1, from about 1,000:1 to about 10,000:1, from about 5,000:1 to about 10,000:1, from about 50:1 to about 5,000:1, from about 50:1 to about 1,000:1, from about 50:1 to about 500:1, from about 50:1 to about 100:1, from about 100:1 to about 5,000:1, from about 100:1 to about 1,000:1, from about 100:1 to about 500:1, from about 500:1 to about 5,000:1, from about 500:1 to about 1,000:1, or from about 1,000:1 to about 5,000:1. In certain embodiments, the ratio of the viscosity of the acrylated chitosan composition to the oxidized chitosan composition ranges from about 100:1 to about 10,000:1.

In certain embodiments, the ratio of the volume of aCHN solution to the volume of oDEX solution is about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10.

In certain embodiments, the resulting hemostatic hydrogel composition is a hemostatic hydrogel composition disclosed herein. However, it is appreciated that the hydrogel achieves its hemostatic properties and blood coagulation properties in the absence of an additional blood clotting agent that promotes blood clotting or otherwise activates the the blood clotting cascade (e.g., Factor XIII, Factor IX, Factor X, Factor XI, Factor XII, or thrombin). As a result, in certain embodiments, the oxidized dextran, acrylated chitosan, and the hemostatic hydrogel produced by combining the acrylated chitosan and oxidized dextran are substantially free of one or more exogenously added blood clotting agents. In this context, the term "substantially free" of an exogenously added blood clotting agent is understood to mean an amount of the exogenously added agent that is less than is necessary to produce a blood clot in a standard blood clotting assay.

In certain embodiments, the hemostatic composition further comprises a therapeutic agent. In certain embodiments, the therapeutic agent is selected from the group consisting of a small molecule drug, peptide (e.g., hormone), protein, for example, hormone, growth factor, and antibody. In certain embodiments, the small molecule drug compound is selected from the group comprising an antibiotic, a nonsteroidal anti-inflammatory agent, an anti-cancer agent, an antimicrobial.

In certain embodiments, the therapeutic agent can include, without limitation, a polynucleotide (e.g., DNA, RNA), an oligonucleotide, a gene therapy agent, a nucleoside analog (e.g., Cytovene, Epivir, Gemzar, Hivid, Rebetron, Videx, Zerit, Zovirax), a polynucleic acid decoy, a peptide (e.g., peptide hormone), a protein (e.g., a therapeutic antibody, e.g., Ig A, Ig G, Ig M, Ig D, and Ig E antibodies), or a growth factor (e.g., bone morphic growth factor (BMP), angiopoietin, acidic fibroblast growth factor (aFGF), basic fibroblast growth factor (bFGF), vascular endothelial growth factor (vEGF), platelet derived growth factor (PDGF), nerve growth factor (NGF)), an anti-inflammatory drug (e.g., dexamethasone), an immune suppressive agent, an anti-neoplastic agent, an anti-cancer agent, an anti-cell proliferation agent, a nitric oxide releasing agent, an anti-diabetic drug (e.g., rosigliatazone), an antibiotic (e.g., Minocycline, Rifampin, Erythromycin, Novobiocin), an anti-microbial agent (e.g., Triclosan, Fusidic acid, Silver acetate, Polymyxin), an analgesic (e.g., codeine, meperidine, morphine, aspirin, acetaminophen, d-propoxyphene), a burn care agent (e.g., silver sulfadiazine, bacitracin, benzocaine) or any combination thereof. In certain embodiments, the therapeutic agent may be added to the acrylated chitosan composition and/or the oxidized dextran composition prior to contacting the acrylated chitosan composition with the oxidized dextran composition.

In certain embodiments, the hemostatic composition further comprises a plurality of cells, for example, immune cells (for example, genetically modified immune cells such as genetically modified B-cells or T-cells, such as CART cells) and stem cells. In certain embodiments, the stem cells are selected from the group comprising mesenchymal stem cells, pancreatic stem cells, pluripotent stem cells, neural stem cells, hematopoietic stem cells or any combination thereof. The cells may be added to the acrylated chitosan composition and/or the oxidized dextran composition prior to contacting the acrylated chitosan composition with the oxidized dextran composition.

In certain embodiments, the acrylated chitosan composition is contacted with the oxidized dextran composition in a static mixer, and optionally or in addition the mixture is aerosolized prior to application to tissue. In certain embodiments, the mixture is aerosolized using an air-assisted spray tip or an unassisted spray tip.

In certain embodiments, the gelation time of the hemostatic hydrogel composition forms within from about 5 seconds to about 300 seconds, from about 5 seconds to about 240 seconds, from about 5 seconds to about 180 seconds, from about 5 seconds to about 120 seconds, from about 5 seconds to about 60 seconds, from about 7 seconds to about 300 seconds, from about 7 seconds to about 240 seconds, from about 7 seconds to about 180 seconds, from about 7 seconds to about 120 seconds, from about 7 seconds to about 60 seconds, from about 10 seconds to about 300 seconds, from about 10 seconds to about 240 seconds, from about 10 seconds to about 180 seconds, from about 10 seconds to about 120 seconds, or from about 10 seconds to about 60 seconds, after contacting the acrylated chitosan composition with the oxidized dextran composition.

In certain embodiments, the gelation time of the hemostatic hydrogel composition forms within from about 10 seconds to about 240 seconds after contacting the acrylated chitosan composition with the oxidized dextran composition. In certain embodiments, the gelation time of the hemostatic hydrogel composition forms within from about 10 seconds after contacting the acrylated chitosan composition with the oxidized dextran composition. In certain embodiments, the gelation time of the hemostatic hydrogel composition forms within from about 240 seconds after contacting the acrylated chitosan composition with the oxidized dextran composition. In certain embodiments, the hemostatic hydrogel compositions of the present invention with a gelation time of within 240 seconds after contacting the acrylated chitosan composition with the oxidized dextran composition may be useful in the treatment of wounds resulting from minimally invasive surgeries (MIS).

VII Properties of Hemostatic Compositions

The hemostatic hydrogels described herein have a variety of structural and/or structural/functional features.
(i) Structural Features
For example, the hemostatic hydrogel comprise two or more of the following features, which include (i) a total amount of free aldehyde groups of from about 0.1 to about 0.7 moles aldehyde/mole oxidized dextran, (ii) the hydrogel composition is formed from oxidized dextran and acrylated chitosan, wherein the ratio of primary aldehydes in the oxidized dextran to the amines in the acrylated chitosan is in the range from about 1.0 to about 2.0, and/or the ratio of total aldehydes in in the oxidized dextran to amines in the acrylated chitosan is from about 1.5 to about 3.0, (iii) the ratio of Mw of the acrylated chitosan to the oxidized dextran is from about 2 to about 10, the ratio of Mn of the acrylated chitosan to the oxidized dextran is from about 4 to about 15, the ratio of Mz of the acrylated chitosan to the oxidized dextran is from about 2 to about 10, the ratio of PDI (Mw/Mn) of acrylated chitosan to oxidized dextran is from about 0.5 to about 0.8, and/or the ratio of PDI (Mz/Mw) of acrylated chitosan to oxidized dextran is from about 0.5 to about 1.0, (iv) upon formation of the hydrogel composition, the hydrogel composition comprises a bound water content of from about 65% w/w to about 95% w/w, (v) a three-dimensional porous structure comprising layers of substantially non-interconnected pores having (a) a pore size distribution from about 10 μm to about 850 μm in diameter, (b) a platelet adhesive surface, or a combination of (a) and (b), and/or (vi) the hydrogel composition comprises walls disposed between the substantially non-interconnected pores, the walls having a wall thickness of from 0.046 μm to 50 μm.

In certain embodiments, the hydrogel composition increases in burst strength over time. For example, in certain embodiments (i) at about 10 seconds after the formation of the hydrogel composition, the hydrogel composition has a burst strength of greater than 20 mmHg as determined using an ASTM F 2392-04 protocol, (ii) at about 2 minutes after the formation of the hydrogel composition, the hydrogel composition has a burst strength of greater than about 35 mmHg as determined using an ASTM F 2392-04 protocol, and/or (iii) at about 5 minutes after the formation of the hydrogel composition, the hydrogel composition has a burst strength of greater than about 70 mmHg as determined using an ASTM F 2392-04 protocol. In certain embodiments, the hydrogel composition (i) has an elastic modulus of from about 500 Pa to about 5000 Pa at from about 10 seconds to about 80 seconds after the formation of the hydrogel composition, (ii) has a compression modulus of from about 3 kPa to about 250 kPa, and/or (iii) has an average adhesion strength of from about 1.0 N to about 50.0 N, as determined using an ASTM F 2258-05 protocol.

In certain embodiments, the volume of the hydrogel composition (i) when formed, does not swell upon exposure to a physiological fluid or body fluid, and/or (ii) shrinks by less than about 5%, for example, less than about 5%, 3%, 2% about 10 minutes after formation when exposed to a physiological fluid or body fluid.

In certain embodiments, the hydrogel composition is substantially transparent when the hydrogel composition has a thickness of 2 mm to 10 mm. This permits a medical practitioner (e.g., surgeon) to visualize the underlying tissue and/or tissue lesion after application of the hemostat to confirm that bleeding has slowed or stopped.

In certain embodiments, the hydrogel composition comprises a total amount of free aldehyde groups of from about 0.1 to about 0.7, from about 0.1 to about 0.6, from about 0.2 to about 0.6, from about 0.3 to about 0.6, from about 0.4 to about 0.6, from about 0.5 to about 0.6, from about 0.1 to about 0.5, from about 0.1 to about 0.4, from about 0.1 to about 0.3, from about 0.1 to about 0.2, from about 0.2 to about 0.5, from about 0.2 to about 0.4, from about 0.2 to about 0.3, from about 0.3 to about 0.5, from about 0.3 to about 0.4, or from about 0.4 to about 0.5 moles aldehyde/mole oxidized dextran. In certain embodiments, the hydrogel composition comprises a total amount of free aldehyde groups of from about 0.1 to about 0.7 moles aldehyde/mole oxidized dextran. In certain embodiments, the hydrogel composition comprises a total amount of free aldehyde groups of from about 0.2 to about 0.5 moles aldehyde/mole oxidized dextran.

In certain embodiments, the ratio of primary aldehydes in the oxidized dextran to the amines in the acrylated chitosan is in the range from about 1.0 to about 2.0, from about 1.2 to about 2.0, from about 1.4 to about 2.0, from about 1.6 to about 2.0, from about 1.8 to about 2.0, from about 1.0 to about 1.2, from about 1.0 to about 1.4, from about 1.0 to about 1.6, from about 1.0 to about 1.8, from about 1.2 to about 1.4, from about 1.2 to about 1.6, from about 1.2 to about 1.8, from about 1.4 to about 1.6, from about 1.4 to about 1.8, or from about 1.6 to about 1.8. In certain embodiments, the ratio of primary aldehydes in the oxidized dextran to the amines in the acrylated chitosan is in the range from about 1.0 to about 1.8.

In certain embodiments, the ratio of total aldehydes in in the oxidized dextran to amines in the acrylated chitosan is from about 1.5 to about 3.0, from about 2.0 to about 3.0, from about 2.5 to about 3.0, from about 1.5 to about 2.5, from about 1.5 to about 2.0, or from about 2.0 to about 2.5. In certain embodiments, the ratio of total aldehydes in in the oxidized dextran to amines in the acrylated chitosan is from about 1.5 to about 2.8.

In certain embodiments, the ratio of Mw of the acrylated chitosan to the oxidized dextran is from about 2 to about 10, from about 4 to about 10, from about 6 to about 10, from about 8 to about 10, from about 2 to about 8, from about 2 to about 6, from about 2 to about 4, from about 4 to about 8, from about 4 to about 6, or about from about 6 to about 8. In certain embodiments, the ratio of Mw of the acrylated chitosan to the oxidized dextran is from about 4 to about 8.

In certain embodiments, the ratio of Mn of the acrylated chitosan to the oxidized dextran is from about 4 to about 15, from about 8 to about 15, from about 12 to about 15, from about 4 to about 12, from about 4 to about 8, or from about 8 to about 12. In certain embodiments, the ratio of Mn of the acrylated chitosan to the oxidized dextran is from about 8 to about 15.

In certain embodiments, the ratio of Mz of the acrylated chitosan to the oxidized dextran is from about 2 to about 10, from about 4 to about 10, from about 6 to about 10, from about 8 to about 10, from about 2 to about 8, from about 2 to about 6, from about 2 to about 4, from about 4 to about 8, from about 4 to about 6, or from about 6 to about 8. In certain embodiments, the ratio of Mz of the acrylated chitosan to the oxidized dextran is from about 4 to about 8.

In certain embodiments, the ratio of PDI (Mw/Mn) of acrylated chitosan to oxidized dextran is from about 0.5 to about 0.8, from about 0.6 to about 0.8, from about 0.7 to about 0.8, from about 0.5 to about 0.7, from about 0.5 to about 0.6, or from about 0.6 to about 0.7. In certain embodiments, the ratio of PDI (Mw/Mn) of acrylated chitosan to oxidized dextran is from about 0.5 to about 0.7.

In certain embodiments, the ratio of PDI (Mz/Mw) of acrylated chitosan to oxidized dextran is from about 0.5 to about 1.0, from about 0.6 to about 1.0, from about 0.7 to about 1.0, from about 0.8 to about 1.0, from about 0.9 to about 1.0, from about 0.5 to about 0.9, from about 0.5 to about 0.8, from about 0.5 to about 0.7, from about 0.5 to about 0.6, from about 0.6 to about 0.9, from about 0.6 to about 0.8, from about 0.6 to about 0.7, from about 0.7 to about 0.9, from about 0.7 to about 0.8, or from about 0.8 to about 0.9. In certain embodiments, the ratio of PDI (Mz/Mw) of acrylated chitosan to oxidized dextran is from about 0.8 to about 1.0.

In certain embodiments, upon formation of the hydrogel composition, the hydrogel composition comprises a bound water content of from about 60% w/w to about 99% w/w, from about 65% w/w to about 99% w/w, from about 70% w/w to about 99% w/w, from about 75% w/w to about 99% w/w, from about 80% w/w to about 99% w/w, from about 85% w/w to about 99% w/w, from about 90% w/w to about 99% w/w, from about 95% w/w to about 99% w/w, from about 60% w/w to about 95% w/w, from about 60% w/w to about 90% w/w, from about 60% w/w to about 85% w/w, from about 60% w/w to about 80% w/w, from about 60% w/w to about 75% w/w, from about 60% w/w to about 70% w/w, from about 60% w/w to about 65% w/w, from about 65% w/w to about 95% w/w, from about 65% w/w to about 90% w/w, from about 65% w/w to about 85% w/w, from about 65% w/w to about 80% w/w, from about 65% w/w to about 75% w/w, from about 65% w/w to about 70% w/w, from about 70% w/w to about 95% w/w, from about 70% w/w to about 90% w/w, from about 70% w/w to about 85% w/w, from about 70% w/w to about 80% w/w, from about 70% w/w to about 75% w/w, from about 75% w/w to about 95% w/w, from about 75% w/w to about 90% w/w, from about 75% w/w to about 85% w/w, from about 75% w/w to about 80% w/w, from about 80% w/w to about 95% w/w, from about 80% w/w to about 90% w/w, from about 80% w/w to about 85% w/w, from about 85% w/w to about 95% w/w, from about 85% w/w to about 90% w/w, or from about 90% w/w to about 95% w/w. In certain embodiments, upon formation of the hydrogel composition, the hydrogel composition comprises a bound water content of from about 65% w/w to about 95% w/w.

Figure 2:
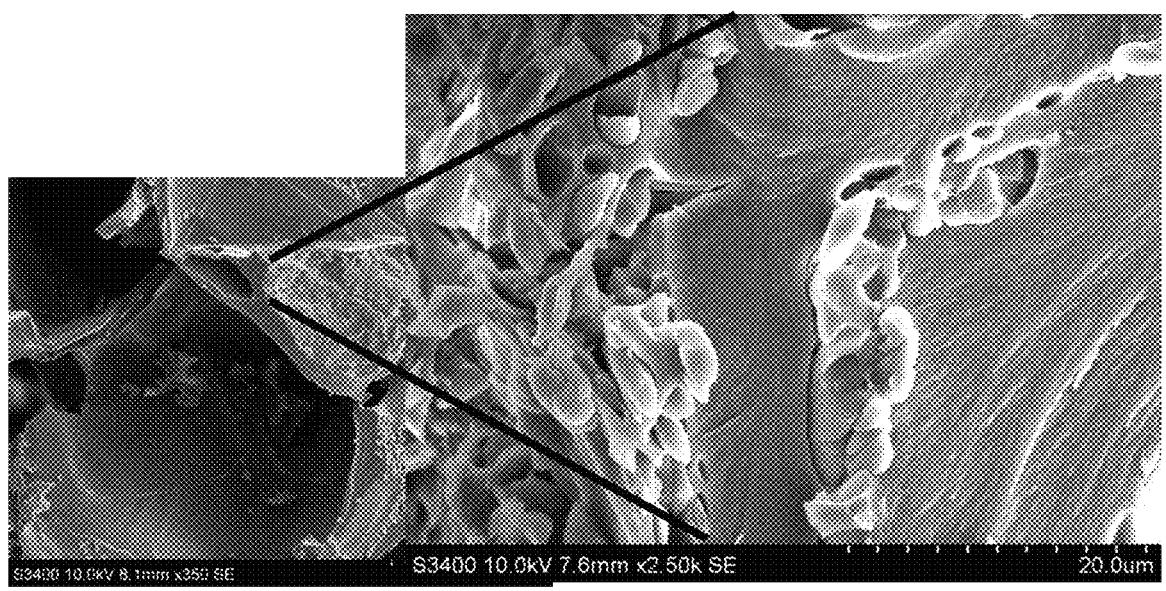
FIG. 2 is a SEM image of the surface of an exemplary acrylated chitosan/oxidized dextran hydrogel.
Figure 3:
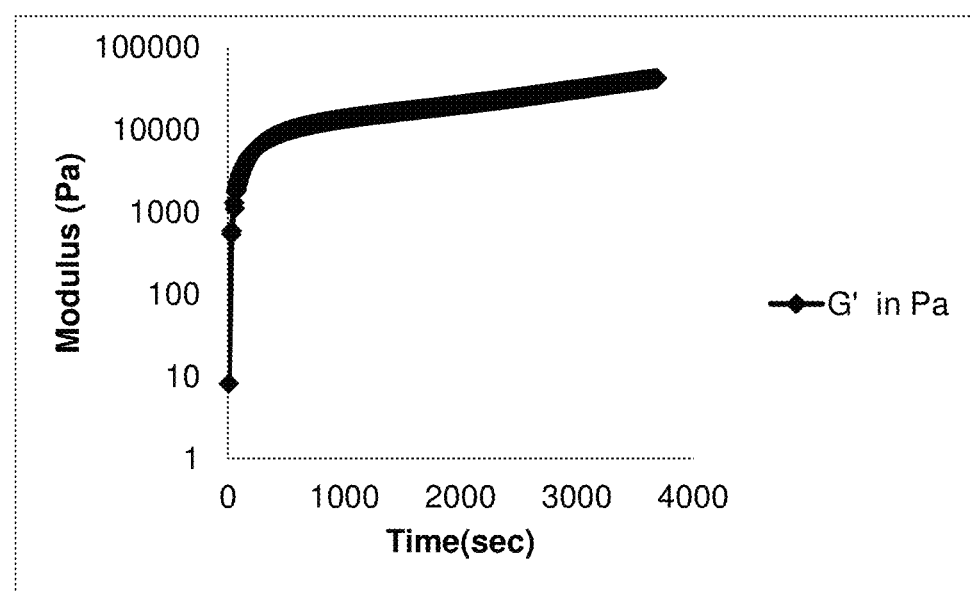
FIG. 3 is a graph showing the elastic modulus of an exemplary acrylated chitosan/oxidized dextran hydrogel as a function of time.
Figure 4:
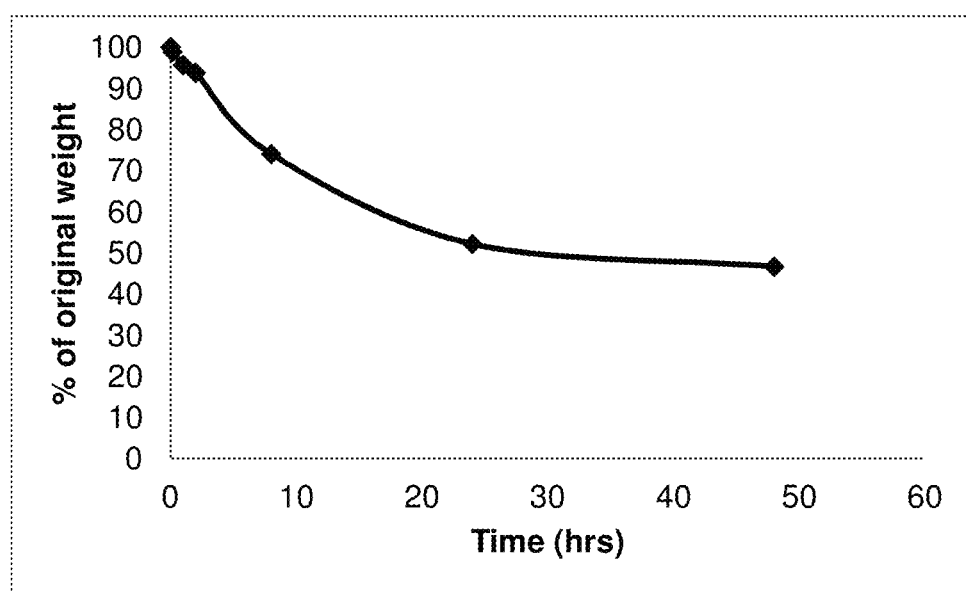
FIG. 4 is a graph showing the weight of an exemplary acrylated chitosan/oxidized dextran hydrogel following formation of a hydrogel as a function of time.

In certain embodiments, the hemostatic hydrogel composition comprises a three-dimensional porous structure, that comprises layers of substantially non-interconnected pores (see, e.g., FIG. 1). In certain embodiments, the layers of substantially non-interconnected pores comprise anisotropic pores and/or isotropic pores. In certain embodiments, the layers of substantially non-interconnected pores comprise both anisotropic pores and isotropic pores. In certain embodiments, the pores have a pore size distribution from about 10 μm to about 850 μm in diameter, where the diameter of a pore is the longest possible straight-line distance between the edges of the pore.

In certain embodiments, the ratio of the pore volume to the hydrogel volume is from about 0.9 to about 0.98. In certain embodiments, the ratio of the volume of the walls disposed between the pores to the hydrogel volume is from about 0.02 to about 0.09. In certain embodiments, the ratio of the pore volume to the volume of the walls disposed between the pores is from about 10 to about 33.

In certain embodiments, at about 2 minutes after the formation of the hydrogel composition, the hydrogel composition has a burst strength of from about 35 mmHg to about 80 mmHg, from about 40 mmHg to about 80 mmHg, from about 45 mmHg to about 80 mmHg, from about 50 mmHg to about 80 mmHg, from about 60 mmHg to about 80 mmHg, from about 70 mmHg to about 80 mmHg, from about 35 mmHg to about 70 mmHg, from about 35 mmHg to about 60 mmHg, from about 35 mmHg to about 50 mmHg, from about 35 mmHg to about 45 mmHg, from about 35 mmHg to about 40 mmHg, from about 40 mmHg to about 80 mmHg, from about 40 mmHg to about 70 mmHg, from about 40 mmHg to about 60 mmHg, from about 40 mmHg to about 50 mmHg, from about 40 mmHg to about 45 mmHg, from about 50 mmHg to about 80 mmHg, from about 50 mmHg to about 70 mmHg, from about 50 mmHg to about 60 mmHg, from about 60 mmHg to about 80 mmHg, from about 60 mmHg to about 70 mmHg, or from about 70 mmHg to about 80 mmHg, as determined using an ASTM F 2392-04 protocol.

In certain embodiments, at about 5 minutes after the formation of the hydrogel composition, the hydrogel composition has a burst strength of from about 70 mmHg to about 125 mmHg, from about 70 mmHg to about 115 mmHg, from about 70 mmHg to about 110 mmHg, from about 75 mmHg to about 110 mmHg, from about 80 mmHg to about 110 mmHg, from about 85 mmHg to about 110 mmHg, from about 90 mmHg to about 110 mmHg, from about 100 mmHg to about 110 mmHg, from about 70 mmHg to about 100 mmHg, from about 70 mmHg to about 90 mmHg, from about 70 mmHg to about 85 mmHg, from about 70 mmHg to about 80 mmHg, from about 70 mmHg to about 75 mmHg, from about 75 mmHg to about 100 mmHg, from about 75 mmHg to about 90 mmHg, from about 75 mmHg to about 85 mmHg, from about 75 mmHg to about 80 mmHg, from about 80 mmHg to about 100 mmHg, from about 80 mmHg to about 90 mmHg, from about 80 mmHg to about 85 mmHg, from about 85 mmHg to about 100 mmHg, from about 85 mmHg to about 90 mmHg, or from about 90 mmHg to about 100 mmHg, as determined using an ASTM F 2392-04 protocol.

In certain embodiments, the hemostatic hydrogel composition, when formed, does not swell upon exposure to a physiological fluid or body fluid.

In certain embodiments, the volume of the hydrogel composition shrinks by less than about 1.0%, about 1.2%, about 1.4%, about 1.6%, about 1.8%, about 2.0%, about 2.2%, about 2.4%, about 2.6%, about 2.8%, about 3.0%, about 3.2%, about 3.4%, about 3.6%, about 3.8%, about 4.0%, about 4.2%, about 4.4%, about 4.6%, about 4.8%, or about 5%, about 10 minutes after formation when exposed to a physiological fluid or body fluid.

In certain embodiments, the hydrogel composition is substantially transparent when the hydrogel composition has a thickness of 2 mm to 10 mm. In certain embodiments, a substantially transparent hydrogel composition maybe defined as any hydrogel composition with a visible light % transmittance of greater than 65%, wherein the % transmittance of the hydrogel composition is measured using a UV-vis spectrometer.

In certain embodiments, the hemostatic hydrogel comprises pores certain of which having platelet adhesive surfaces that are sufficiently rough to permit activated platelets and/or red blood cells to adhere to the platelet adhesive surfaces.

In certain embodiments, the hemostatic hydrogel compositions of the present invention comprise:
(a) from about 0.0 to about 0.3 mole fraction of a first monomer of formula (I)

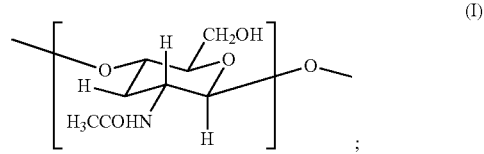

(b) from about 0.02 to about 0.7 mole fraction of a second monomer of formula (III),

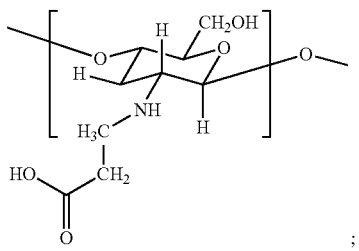

and (c) about 0.0 to about 0.8 mole fraction of a second monomer of formula (V),

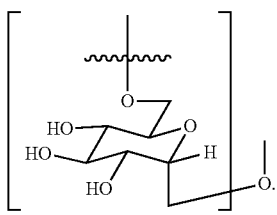

In certain embodiments, the hemostatic hydrogel composition comprises from about 0.0 to about 0.26, from about 0.05 to about 0.26, from about 0.1 to about 0.26, from about 0.15 to about 0.26, from about 0.2 to about 0.26, from about 0.0 to about 0.2, from about 0.0 to about 0.15, from about 0.0 to about 0.1, from about 0.0 to about 0.05, from about 0.05 to about 0.2, from about 0.05 to about 0.15, from about 0.05 to about 0.1, from about 0.1 to about 0.2, from about 0.1 to about 0.15, or from about 0.15 to about 0.2, mole fraction of the first monomer of formula (I). In certain embodiments, the hemostatic hydrogel composition comprises from about 0.0 to about 0.26 mole fraction of the first monomer of formula (I).

In certain embodiments, the hemostatic hydrogel composition comprises from about 0.03 to about 0.7, from about 0.03 to about 0.6, from about 0.05 to about 0.6, from about 0.1 to about 0.6, from about 0.3 to about 0.6, from about 0.5 to about 0.6, from about 0.03 to about 0.5, from about 0.03 to about 0.3, from about 0.03 to about 0.1, from about 0.03 to about 0.05, from about 0.05 to about 0.5, from about 0.05 to about 0.3, from about 0.05 to about 0.1, from about 0.1 to about 0.5, from about 0.1 to about 0.3, or from about 0.3 to about 0.5, mole fraction of the third monomer of formula (III). In certain embodiments, wherein the hemostatic hydrogel composition from about 0.03 to about 0.6 mole fraction of the third monomer of formula (III).

In certain embodiments, the hemostatic hydrogel composition comprises from about 0.02 to about 0.8, from about 0.04 to about 0.8, from about 0.0 to about 0.7, from about 0.02 to about 0.7, from about 0.04 to about 0.7, from about 0.1 to about 0.7, from about 0.3 to about 0.7, from about 0.5 to about 0.7, from about 0.04 to about 0.5, from about 0.04 to about 0.3, from about 0.04 to about 0.1, from about 0.1 to about 0.5, from about 0.1 to about 0.3, or from about 0.3 to about 0.5, mole fraction of the first monomer of formula (V). In certain embodiments, the hemostatic hydrogel composition comprises from about 0.04 to about 0.7 mole fraction of the first monomer of formula (V).

In certain embodiments, wherein the hemostatic hydrogel composition comprises no greater than about 0.2 mole fraction of a fourth monomer of formula (IV)

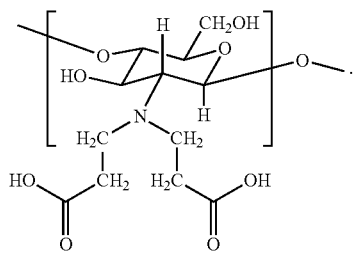

In certain embodiments, the hemostatic hydrogel composition further comprises from about 0.0 to about 0.2, from about 0.05 to about 0.2, from about 0.1 to about 0.2, from about 0.15 to about 0.2, from about 0.0 to about 0.15, from about 0.0 to about 0.1, from about 0.0 to about 0.05, from about 0.05 to about 0.15, from about 0.05 to about 0.1, or from about 0.1 to about 0.15, mole fraction of the fourth monomer of formula (IV).

In certain embodiments, the hemostatic hydrogel composition comprises no greater than about 0.65 mole fraction of a fifth monomer of formula (VIII)

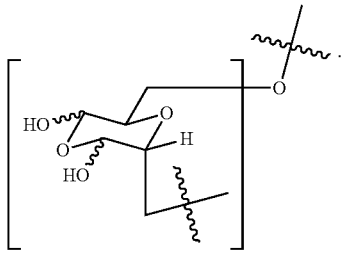

In certain embodiments, the hemostatic hydrogel composition comprises from about 0.0 to about 0.65, from about 0.2 to about 0.65, from about 0.4 to about 0.65, from about 0.0 to about 0.4, from about 0.0 to about 0.2, or from about 0.2 to about 0.4, mole fraction of a third monomer of formula (VIII).

In certain embodiments, the hydrogel comprises a plurality of crosslinked moieties of formula (IX)

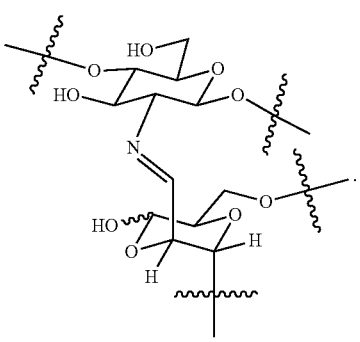

(ii) Structural/Functional Features

In certain embodiments, the hydrogels contain pores certain of which have a platelet adhesive surface so that, when in contact with blood, the hydrogel composition permits (i) platelets and/or red blood cells to bind to the platelet adhesive surface and promote blood clot formation at or within the hydrogel composition, and/or (ii) platelets and/or red blood cells to adhere to the platelet adhesive surface and not permit platelets and/or red blood cells from the blood to enter pores present in a first surface of the hydrogel composition, pass through the hydrogel composition, and then exit the hydrogel composition via pores present in a second surface of the hydrogel composition that opposes the first surface.

The invention provides methods of promoting hemostasis (e.g., reducing or stopping blood loss) at a location in a subject in need thereof by applying a hydrogel composition of the invention to the location to be treated in the subject.

In certain embodiments, the hemostatic hydrogel composition adheres to a tissue surface at the location. In certain embodiments, the hemostatic hydrogel composition adheres to the tissue surface at the location with average adhesion strength of from about 1.0 N to about 50.0 N, as determined using an ASTM F 2258-05 protocol.

In certain embodiments, platelets and/or red blood cells present at the location adhere to surfaces of pores in the hemostatic hydrogel.

In certain embodiments, the hemostatic hydrogel composition promotes platelet adhesion, platelet activation, and platelet aggregation at the site in need of hemostasis. During use, the hemostatic hydrogel composition promotes a blood coagulation cascade and blood clot formation at the site.

In certain embodiments, blood coagulation is achieved from about 10 seconds to about 300 seconds, from about 20 seconds to about 300 seconds, from about 30 seconds to about 300 seconds, from about 60 seconds to about 300 seconds, from about 120 seconds to about 300 seconds, from about 180 seconds to about 300 seconds, from about 240 seconds to about 300 seconds, from about 10 seconds to about 240 seconds, from about 10 seconds to about 180 seconds, from about 10 seconds to about 120 seconds, from about 10 seconds to about 60 seconds, from about 10 seconds to about 30 seconds, from about 10 seconds to about 20 seconds, from about 20 seconds to about 240 seconds, from about 20 seconds to about 180 seconds, from about 20 seconds to about 120 seconds, from about 20 seconds to about 60 seconds, from about 20 seconds to about 30 seconds, from about 30 seconds to about 240 seconds, from about 30 seconds to about 180 seconds, from about 30 seconds to about 120 seconds, from about 30 seconds to about 60 seconds, from about 60 seconds to about 240 seconds, from about 60 seconds to about 180 seconds, from about 60 seconds to about 120 seconds, from about 120 seconds to about 240 seconds, from about 120 seconds to about 180 seconds, or from about 180 seconds to about 240 seconds. In certain embodiments, when a hemostatic hydrogel composition of the present invention is applied to an abrasion, blood coagulation is achieved from about 20 seconds to about 210 seconds.

In certain embodiments, the hemostatic hydrogel compositions degrade within days, weeks (e.g., in 1 week, 2 weeks, 3 weeks, or 4 weeks) or months (e.g., two, three, four, five or six months).

In certain embodiments, the hemostatic hydrogel compositions of the present invention are biodegradable. Without wishing to be bound by theory it is believed that degradation of the hydrogels occurs by hydrolysis and enzymatic degradation. The degradation pathway may occur through a combination of two mechanisms. A first mechanism may involve cleavage of the crosslinks (e.g., the Schiff base linkages) between the polymer chains producing water soluble fragments. It is believed that the Schiff base linkages are reversible which leads to a progressive reorganization during which the polymer chains become degraded. A second mechanism may involve the degradation of the acrylated chitosan and oxidized dextran chains to produce smaller fragments (e.g., oligomers or monomers that are water soluble). Given that the hydrogel is formed from naturally occurring sugars, the products of degradation are non-toxic and are further degraded by the carbohydrate metabolism pathways or rapidly eliminated by the renal system.

It is believed that one of the rate limiting steps for the degradation process is the degree of acetylation (DA) of the acrylated chitosan. Given that certain enzymes, e.g., lysozyme, require a linear series of at least three N-acetylglucosamine units to cleave a glycidic link. Many enzymes have a hydrophobic pocket that interact with the polymer e.g., around three linear N-acetylglucosamine subunits, and catalyzes the chain cleavage. The probability of having three N-acetylglucosamine units in a row is given by DA×DA× DA=$DA^3$. As a result, as DA decreases, the probability of having three linear, adjacent N-acetylglucosamine subunits together drops as the third power DA. It is understood, however, that the rate of degradation can be modified or adjusted by altering the DA content of acrylated chitosan used to create the hydrogel.

In another aspect, provided is a hemostatic hydrogel composition comprising two or more of the following features:

(i) the hydrogel composition comprises a three-dimensional porous structure comprising layers of substantially non-interconnected pores having (a) a pore size distribution from about 10 µm to about 850 µm in diameter, (b) a platelet adhesive surface, or a combination of (a) and (b), (ii) the hydrogel composition comprises walls disposed between the substantially non-interconnected pores, the walls having a wall thickness of from 0.046 µm to 50 µm, (iii) the hydrogel composition comprises a platelet adhesive surface so that, when in contact with blood, the hydrogel composition permits platelets and/or red blood cells within the blood to adhere to platelet adhesive surface and promote blood clot formation at or within the hydrogel composition, (iv) the hydrogel composition comprises a platelet adhesive surface so that, when in contact with blood, the hydrogel composition permits platelet and/or red blood cells within the blood to adhere to the platelet adhesive surface and not permit platelets and/or red blood cells from the blood to enter pores present in a first surface of the hydrogel composition, pass through the hydrogel composition, and then exit the hydrogel composition via pores present in a second surface of the hydrogel composition that opposes the first surface, (v) at about 10 seconds after the formation of the hydrogel composition, the hydrogel composition has a burst strength of greater than 20 mmHg as determined using an ASTM F 2392-04 protocol, (vi) at about 2 minutes after the formation of the hydrogel composition, the hydrogel composition has a burst strength of greater than about 35 mmHg as determined using an ASTM F 2392-04 protocol, (vii) at about 5 minutes after the formation of the hydrogel composition, the hydrogel composition has a burst strength of greater than about 70 mmHg as determined using an ASTM F 2392-04 protocol,
(viii) the hydrogel composition has an elastic modulus of from about 500 Pa to about 5000 Pa at from about 10 seconds to about 80 seconds after the formation of the hydrogel composition,
(ix) the hydrogel composition has a compression modulus of from about 3 kPa to about 250 kPa,
(x) the hydrogel composition has an average adhesion strength of from about 1.0 N to about 50.0 N, as determined using an ASTM F 2258-05 protocol,
(xi) the volume of the hydrogel composition, when formed, does not increase upon exposure to a physiological fluid or body fluid,
(xii) the volume of the hydrogel composition shrinks by less than about 5% about 10 minutes after formation when exposed to a physiological fluid or body fluid,
(xiii) the hydrogel composition is substantially transparent when the hydrogel composition has a thickness of 2 mm to 10 mm, and
(xiv) the hydrogel composition optionally further comprises a therapeutic agent.

VIII Methods of Treatment and Administration

It is understood that the hemostatic hydrogel compositions can be used to promote hemostasis in a variety of scenarios, for example, when the blood loss is caused by trauma, abrasion, or surgical or other medical intervention at the location.

In certain embodiments, the surgical intervention is selected from an arthroscopic procedure, a cardiac surgery, a cranial surgery, an endoscopic procedure, a laparoscopic procedure, an OB-GYN surgery, an organ surgery, a plastic surgery, a sinus procedure, a spinal surgery, a thoracic surgery, or a vascular surgery. In certain circumstances, the cranial surgery can comprise a procedure to remove a hematoma or a tumor. In certain embodiments, the surgical intervention is a minimally invasive surgery, an endoscopic procedure, a laparoscopic procedure, or an arthroscopic procedure. In other approaches, the hemostatic hydrogel compositions of the present invention can be used as a topical wound dressing, for example, for the treatment of burns.

It is understood that, when appropriate, the hemostatic hydrogel composition, when applied to the site, is capable of filling a cavity at the site without inducing compression of tissue surrounding the cavity when the hemostatic composition is exposed to physiological fluid or a body fluid. This can be particularly important during brain or spinal surgery where swelling of the hemostat in these locations is undesirable as it can cause compression of surrounding tissue.

In addition, it is understood that the hemostatic hydrogel can be used to facilitate the delivery of a therapeutic agent to a site if intent, for example, during surgery. In certain embodiments, the therapeutic agent is selected from the group consisting of a small molecule drug, a growth factor, a hormone, an antibody, an anti-cancer agent, an antimicrobial. In certain embodiments, the small molecule drug compound is selected from the group comprising an antibiotic, a non-steroidal anti-inflammatory agent.

In certain embodiments, the therapeutic agent can include, without limitation, a polynucleotide (e.g., DNA, RNA), an oligonucleotide, a gene therapy agent, a nucleoside analog (e.g., Cytovene, Epivir, Gemzar, Hivid, Rebetron, Videx, Zerit, Zovirax), a polynucleic acid decoy, a peptide (e.g., peptide hormone), a protein (e.g., a therapeutic antibody, e.g., Ig A, Ig G, Ig M, Ig D, and Ig E antibodies), or a growth factor (e.g., bone morphic growth factor (BMP), angiopoietin, acidic fibroblast growth factor (aFGF), basic fibroblast growth factor (bFGF), vascular endothelial growth factor (vEGF), platelet derived growth factor (PDGF), nerve growth factor (NGF)), an anti-inflammatory drug (e.g., dexamethasone), an immune suppressive agent, an anti-neoplastic agent, an anti-cancer agent, an anti-cell proliferation agent, a nitric oxide releasing agent, an anti-diabetic drug (e.g., rosigliatazone), an antibiotic (e.g., Minocycline, Rifampin, Erythromycin, Novobiocin), an anti-microbial agent (e.g., Triclosan, Fusidic acid, Silver acetate, Polymyxin), an analgesic (e.g., codeine, meperidine, morphine, aspirin, acetaminophen, d-propoxyphene), a burn care agent (e.g., silver sulfadiazine, bacitracin, benzocaine) or any combination thereof.

In certain embodiments, the method further comprising administering a plurality of cells, for example, immune cells, e.g., engineered immune cells (e.g., CAR T cells) or stem cells to the site. In certain embodiments, the hemostatic composition comprises a plurality of stem cells. In certain embodiments, the plurality of stem cells comprise stem cells selected from mesenchymal stem cells, pancreatic stem cells, pluripotent stem cells, neural stem cells, hematopoietic stem cells or any combination thereof. In certain embodiments, the hemostatic hydrogel compositions of the present invention can be used to promote tissue regeneration.

In certain embodiments, when a hemostatic hydrogel composition of the present invention is applied to an abrasion, hemostasis is achieved, for example, from about 5 seconds to about 120 seconds, from about 10 seconds to about 120 seconds, from about 15 seconds to about 120 seconds, from about 5 seconds to about 60 seconds, from about 10 seconds to about 60 seconds, from about 15 seconds to about 60 seconds, from about 5 seconds to about 30 seconds, from about 10 seconds to about 30 seconds, from about 15 seconds to about 30 seconds, from about 5 seconds to about 15 seconds, or from about 10 seconds to about 15 seconds, after the hemostatic hydrogel composition is applied to the location. In certain embodiments, when a hemostatic hydrogel composition of the present invention is applied to an abrasion, hemostasis is achieved from about 10 seconds to about 40 seconds, after the hemostatic hydrogel composition is applied to the location.

In certain embodiments, when a hemostatic hydrogel composition of the present invention is applied to a biopsy punch, hemostasis is achieved, for example, from about 5 seconds to about 60 seconds, from about 10 seconds to about 60 seconds, from about 15 seconds to about 60 seconds, from about 20 seconds to about 60 seconds, from about 25 seconds to about 60 seconds, from about 30 seconds to about 60 seconds, from about 40 seconds to about 60 seconds, from about 50 seconds to about 60 seconds, from about 5 seconds to about 50 seconds, from about 5 seconds to about 40 seconds, from about 5 seconds to about 35 seconds, from about 5 seconds to about 30 seconds, from about 5 seconds to about 25 seconds, from about 5 seconds to about 20 seconds, from about 5 seconds to about 15 seconds, from about 5 seconds to about 10 seconds, from about 10 seconds to about 50 seconds, from about 10 seconds to about 40 seconds, from about 10 seconds to about 35 seconds, from about 10 seconds to about 30 seconds, from about 10 seconds to about 25 seconds, from about 10 seconds to about 20 seconds, from about 10 seconds to about 15 seconds, from about 15 seconds to about 50 seconds, from about 15 seconds to about 40 seconds, from about 15 seconds to about 35 seconds, from about 15 seconds to about 30 seconds, from about 15 seconds to about 25 seconds, from about 15 seconds to about 20 seconds, from about 20 seconds to about 50 seconds, from about 20 seconds to about 40 seconds, from about 20 seconds to about 35 seconds, from about 20 seconds to about 30 seconds, from about 20 seconds to about 25 seconds, from about 25 seconds to about 50 seconds, from about 25 seconds to about 40 seconds, from about 25 seconds to about 35 seconds, from about 25 seconds to about 30 seconds, from about 30 seconds to about 50 seconds, from about 30 seconds to about 40 seconds, from about 30 seconds to about 35 seconds, from about 35 seconds to about 50 seconds, from about 35 seconds to about 40 seconds, or from about 35 seconds to about 40 seconds, after the hemostatic hydrogel composition is applied to the location. In certain embodiments, when a hemostatic hydrogel composition of the present invention is applied to a biopsy punch, hemostasis is achieved from about 10 seconds to about 20 seconds, after the hemostatic hydrogel composition is applied to the location.

In certain embodiments, when a hemostatic hydrogel composition of the present invention is applied to a laceration, hemostasis is achieved, for example, from about 10 seconds to about 100 seconds, from about 20 seconds to about 100 seconds, from about 30 seconds to about 100 seconds, from about 40 seconds to about 100 seconds, from about 50 seconds to about 100 seconds, from about 70 seconds to about 100 seconds, from about 90 seconds to about 100 seconds, from about 10 seconds to about 90 seconds, from about 10 seconds to about 70 seconds, from about 10 seconds to about 50 seconds, from about 10 seconds to about 40 seconds, from about 10 seconds to about 30 seconds, from about 10 seconds to about 20 seconds, from about 20 seconds to about 90 seconds, from about 20 seconds to about 70 seconds, from about 20 seconds to about 50 seconds, from about 20 seconds to about 40 seconds, from about 20 seconds to about 30 seconds, from about 30 seconds to about 90 seconds, from about 30 seconds to about 70 seconds, from about 30 seconds to about 50 seconds, from about 30 seconds to about 40 seconds, from about 40 seconds to about 90 seconds, from about 40 seconds to about 70 seconds, from about 40 seconds to about 50 seconds, from about 50 seconds to about 90 seconds, from about 50 seconds to about 70 seconds, or from about 70 seconds to about 90 seconds, after the hemostatic hydrogel composition is applied to the location.

In certain embodiments, when a hemostatic hydrogel composition of the present invention is applied to a laceration, hemostasis is achieved, for example, from about 10 seconds to about 90 seconds, after the hemostatic hydrogel composition is applied to the location. In certain embodiments, when a hemostatic hydrogel composition of the present invention is applied to a laceration, hemostasis is achieved from about 80 seconds to about 180 seconds, after the hemostatic hydrogel composition is applied to the location.

In certain embodiments, the hemostatic hydrogel composition is applied to the location in the form of a spray. In certain embodiments, the hemostatic hydrogel composition is applied to the location in the form of a flowable gel. In certain embodiments, the hemostatic hydrogel composition is applied to the location in the form of a liquid bandage.

Kits

In various embodiments, the invention provides kits for producing hemostasis (e.g., reducing or stopping blood loss) at a location in a subject in need thereof. In certain embodiments, a kit comprises: i) instructions for producing hemostasis at a location in a subject in need thereof, ii) an acrylated chitosan composition described herein, and/or iii) an oxidized dextran composition described herein, and an optional mixing system for mixing the acrylated chitosan and oxidized dextran and an optional dispensing system for dispensing a mixture of the acrylated chitosan and the oxidized dextran.

In certain embodiments, the kit comprises a container (for example, syringe, tube, or bottle) containing the acrylated chitosan composition described herein and a container (for example, syringe, tube or bottle) containing the oxidized dextran composition described herein in respective amounts sufficient to produce a hemostatic hydrogel for facilitating hemostasis at the location in the subject in need thereof. In certain embodiments, the kit comprises on or more containers of the acrylated chitosan composition and the oxidized dextran composition described herein in respective amounts sufficient to produce a hemostatic hydrogel for facilitating hemostasis at one or more locations in the subject in need thereof. In certain embodiments, the kit comprises the acrylated chitosan composition and the oxidized dextran composition described herein in amounts sufficient to produce hemostasis at 1, 2, 3, 4, 5, 6, 7, 8, 9, or 10 locations in the subject in need thereof.

EXAMPLES

The invention now being generally described, will be more readily understood by reference to the following examples, which are included merely for purposes of illustration of certain aspects and embodiments of the present invention, and are not intended to limit the invention.

Example 1: Method of Making an Exemplary Acrylated Chitosan Composition

This example describes a method for making an acrylated chitosan for use in creating a hemostatic composition.

An exemplary acrylated chitosan was prepared as follows:

Step 1—Preparation of a Chitosan Intermediate 4.0 g of raw chitosan (Mw=162 kDa, PDI=2.3, DDA=79%) starting material was dissolved in 200 g of 1% (v/v) acetic acid solution for 30 minutes at 25° C. to produce a mixture. The mixture was then heated to 100° C. and held at this temperature for 2 hours.

Step 2—Preparation of the Acrylated Chitosan Intermediate

The mixture comprising the chitosan intermediate was then cooled to 50° C. Thereafter 5.3 g of acrylic acid was added and the mixture was then heated to 100° C. and held at this temperature for 60 minutes. The reaction was then cooled to 28° C. and then quenched by the addition of NaOH until a final pH value of 12.4 was achieved.

Step 3—Preparation of the Acrylated Chitosan Composition

The mixture comprising the acrylated chitosan intermediate was then purified by dialysis for 8 hours to remove salts and low molecular weight components from the mixture to achieve a pH value of 9.1. The purified acrylated chitosan was recovered by precipitation from isopropanol which resulted in a yield of 88%.

Finally, the material was characterized using 1H-NMR spectroscopy and was determined that the mole fraction of the monomer of formula (III) was 0.37.

Example 2: Method of Making an Exemplary Oxidized Dextran Composition

This example describes a method for making an oxidized dextran for use in creating a hemostatic composition.

An exemplary oxidized dextran was prepared as follows:
Step 1—Preparation of the Oxidized Dextran Intermediate A dextran solution was prepared by dissolving 5.0 g of raw dextran starting material (Mw=129 kDa, PDI=4.58) in 400 g of distilled water for 30 minutes at 25° C. Thereafter a sodium periodate solution was prepared by dissolving 3.28 g of sodium periodate in 50 g of distilled water. The sodium periodate solution was then added to the dextran solution and the resulting mixture was stirred for 24 hours.

Step 2—Preparation of the Oxidized Dextran Composition

The mixture comprising the oxidized dextran intermediate was then purified by dialysis for 8 hours in order to remove salts and low molecular weight components from the mixture. The purified oxidized dextran was recovered by precipitation from ethanol which resulted in a yield of 88%.

The total amount of aldehyde groups present on the oxidized dextran was measured using the following titration method:

150 mg of oxidized dextran was added to 35 ml of hydroxylamine hydrochloride solution and allowed to stir for 24 hours at room temperature. This solution was titrated with a NaOH solution. The titration was followed potentiometrically, with the pH recorded as a function NaOH volume. The volume of NaOH solution used to titrate the oxidized dextran solution was taken to be the endpoint, which was determined as the inflection point of the titrimetric curve.

The total amount of aldehyde groups present on the oxidized dextran was found to be 0.76 mol. aldehyde/mol. dextran.

Example 3: Method of Making an Exemplary Hemostatic Composition

This example describes a method for making a hemostatic composition for use in reducing/stopping bleeding at a tissue lesion.

An exemplary hemostatic composition was prepared as follows:

The acrylated chitosan of Example 1 and oxidized dextran of Example 2 were each solubilized into a buffered saline solution to give a final concentration of 7.5% (w/w) and 7.5% (w/w), respectively. Equal amounts of the aqueous solution of the oxidized dextran provided in Example 2 (concentration: 7.5% w/w) and the aqueous solution of acrylated chitosan provided in Example 1 (concentration: 7.5% w/w) were loaded in a dual barrel syringe. A mixer was attached to the top of the dual barrel syringe. The two solutions were then passed through the mixer simultaneously. The hydrogel was observed to form instantaneously at the tip of the mixer. The combined solution was further aerosolized under pressure.

The burst strength of the acrylated chitosan/oxidized dextran hydrogel was measured using ASTM F 2392-04 and found to be 96±11 mmHg (C.I of 95%).

Example 4: Characterization of the Structural Properties of an Exemplary Hemostatic Hydrogel This example describes the characterization of the structural property in an exemplary hemostatic hydrogel.

An acrylated chitosan composition was produced essentially as described in Example 1 and an oxidized dextran composition was prepared essentially as described in Example 2. When combined essentially as described in Example 3, the structural property was analyzed using Scanning Electron Microscopy (SEM).

The structure of the acrylated chitosan/oxidized dextran hydrogels were analyzed using SEM (see, FIG. 1). The hydrogels were found to have formed a three-dimensional layered structure comprising, substantially non-interconnected anisotropic cells/pores formed between the hydrogel backbone walls. The layers of cells/pores were staggered and substantially non-inter connected with layers directly above and below. As a result, the hydrogels could capture cells (e.g., red blood cells) and prevent them from passing through and exiting the hydrogel structure.

Example 5: Characterization of the Elastic Modulus of an Exemplary Hemostatic Hydrogel This example describes the characterization of the elastic modulus in an exemplary hemostatic hydrogel.

An acrylated chitosan composition was produced essentially as described in Example 1 and an oxidized dextran composition was prepared essentially as described in Example 2. When combined essentially as described in Example 3, the elastic modulus was measured using a rheometer. The results are presented in FIG. 3.

The data in FIG. 3 shows that the acrylated chitosan/oxidized dextran hydrogel achieved a desired stiffness of greater than 500 Pa that increases over time; which is required for the hemostatic hydrogel to exert an initial tamponade effect when applied to a wound.

Example 6: Characterization of the Gelation Time of an Exemplary Hemostatic Hydrogel This example describes the characterization of the gelation time of an exemplary hemostatic hydrogel.

An acrylated chitosan composition was produced essentially as described in Example 1 and an oxidized dextran composition was prepared essentially as described in Example 2. When combined essentially as described in Example 3, the gelation time was measured using stir bar stop test. The gelation time was found to be 8 seconds. This example shows that the exemplary hemostatic hydrogel forms quickly, which is important in achieving fast hemostasis.

Example 7: Characterization of the Rate of Shrinkage of an Exemplary Hemostatic Hydrogel This example describes the characterization of the rate of shrinkage of an exemplary hemostatic hydrogel.

An acrylated chitosan composition was produced essentially as described in Example 1 and an oxidized dextran composition was prepared essentially as described in Example 2. When combined essentially as described in Example 3, the rate of shrinkage was measured as function of weight loss over time. The rate of shrinkage of the hydrogel is shown in FIG. 4, which demonstrates that the hydrogel shrinks, rather than swells, overtime. This feature is particularly helpful when a hemostat is used to stop bleeding in confined spaces (e.g., a cranium or a spine) without compressing the nearby tissue.

Example 8: Characterization of the Adhesion Strength of an Exemplary Hemostatic Hydrogel This example describes the characterization of the adhesion in an exemplary hemostatic hydrogel.

An acrylated chitosan composition was produced essentially as described in Example 1 and an oxidized dextran composition was prepared essentially as described in Example 2. When combined essentially as described in Example 3, the adhesion strength was measured using ASTM F 2392-04 and found to be in the range from 16 to 27N. This example shows that the exemplary hemostatic hydrogel has enough strength to adhere to tissue and function as a hemostat.

Example 9: Method of Reducing/Stopping Bleeding Using an Exemplary Hemostatic Composition This example describes a method for reducing/stopping bleeding using an exemplary hemostatic composition. In the following studies, the exemplary hemostat was created essentially as described in Example 3, using the acrylated chitosan and oxidized dextran prepared as essentially described in Examples 1 and 2, respectively.

a) High Flow, Low Pressure Model—Liver (Abrasion Wounds)

In this example, the creation of wounds in a porcine liver was used a standard model to evaluate the effect of the acrylated chitosan/oxidized dextran hydrogel on hemostasis. A Teflon template with a 2 cm diameter circular cut-out to standardize the size of the abrasion wounds. The wound was created by swiping a Bovie scratch pad 5 times over the liver exposed in the template cut-out. The Bovie scratch pad created a bleeding effect similar to that found in human brain surgery. The bleeding wound was then blotted with dry gauze before the acrylated chitosan/oxidized dextran hydrogel was applied to the wound.

Figure 5:
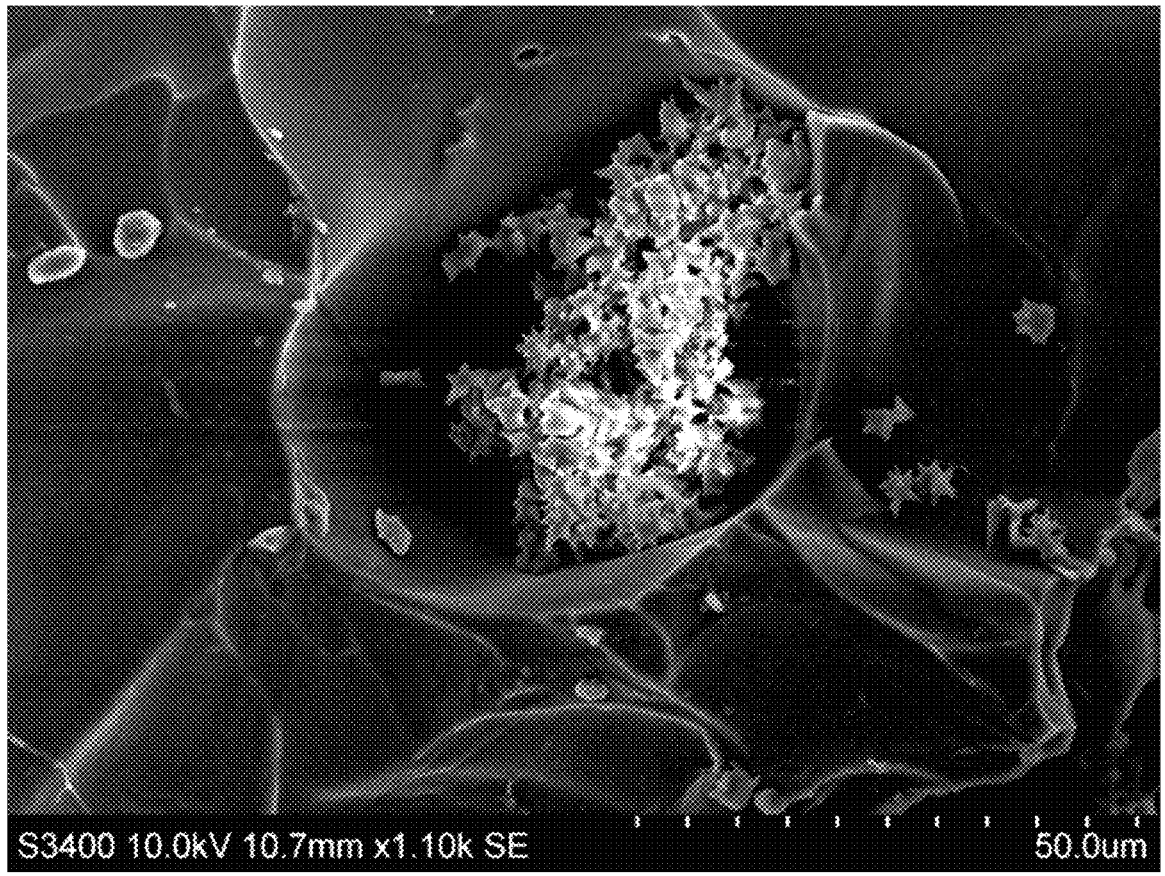
FIG. 5 is an SEM image of a blood clot formed within a pore of an exemplary acrylated chitosan/oxidized dextran hydrogel following formation of a hydrogel at an abrasion wound on a porcine liver.

The transparent hydrogel adhered to the liver tissue and stopped blood flow immediately. The time to hemostasis was found to be 19±6 seconds (C.I of 95%). Complete coagulation (formation of a clot) occurred in 103±36 seconds (C.I of 95%). The formation of a clot was later verified using SEM (see, FIG. 5). FIG. 5 shows the aggregation of activated platelets within a pore. Dendritic pseudopodia of multiple platelets were observed, demonstrating platelet activation.

b) High Flow, High Pressure Model—Liver (Biopsy Punch)

A 10 mm diameter biopsy punch was plunged into a porcine liver, creating a circular wound, 10 mm in diameter and 5-10 mm in depth. Bleeding was observed to occur immediately. The tissue plug created by the punch was removed with forceps to create an open wound with high volume, high pressure bleeding. The wound was blotted with dry gauze, and the acrylated chitosan/oxidized dextran hydrogel was filled into the wound cavity, as well as being applied over the wound surface.

Figure 6:
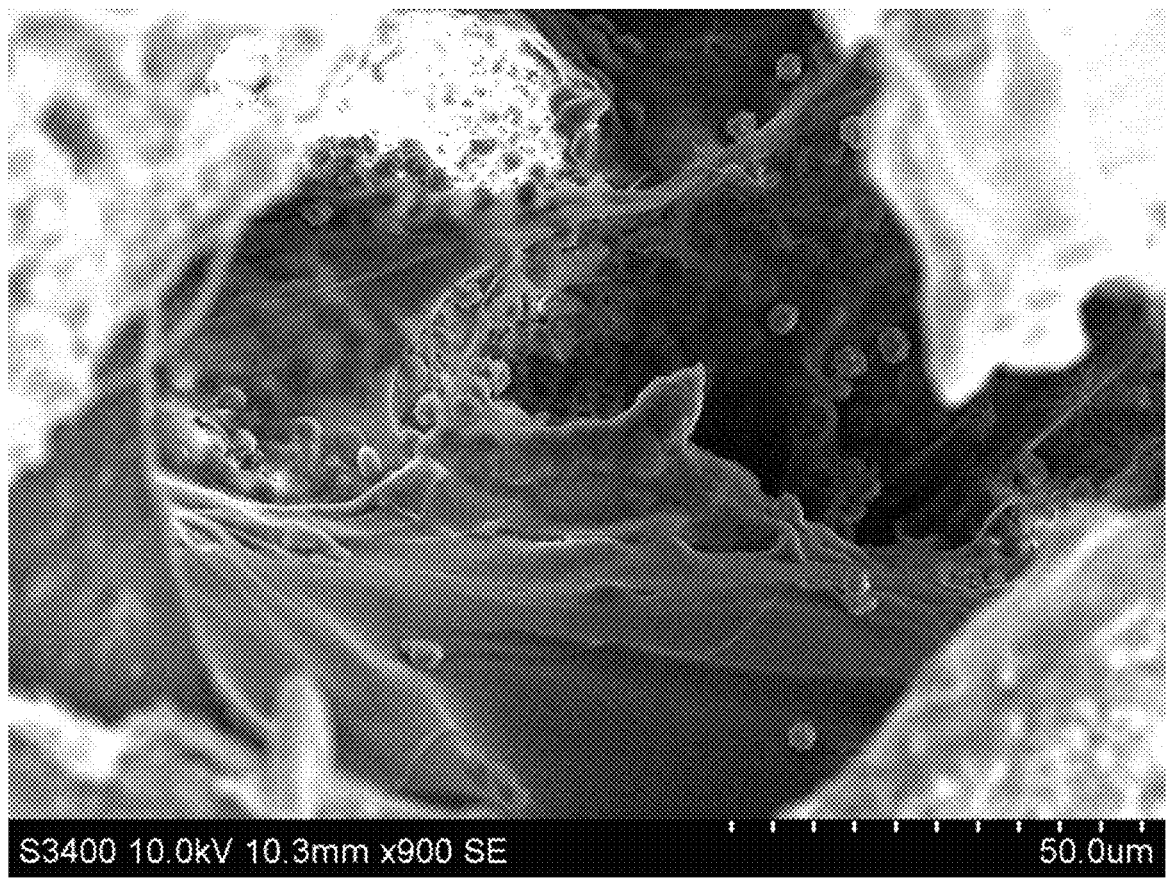
FIG. 6 is an SEM image of a blood clot formed within a pore of an exemplary acrylated chitosan/oxidized dextran hydrogel following formation of a hydrogel at a punch biopsy wound on a porcine liver.

The transparent hydrogel adhered to the tissue and stopped blood flow immediately. The time to hemostasis was found to be between 14 to 18 seconds. The formation of a clot was later verified using SEM (see, FIG. 6).

c) High Flow, High Pressure Model—Liver (Laceration)

A scalpel was used to create lacerations in a porcine liver, the approximate dimensions of the lacerations were 30 mm long×16 mm deep. High flow rate, high pressure bleeding was observed to occur immediately. The wound area was blotted with dry gauze to remove excess blood and allow for visibility. The acrylated chitosan/oxidized dextran hydrogel was filled into the wound cavity, as well as being applied over the wound surface.

Figure 7:
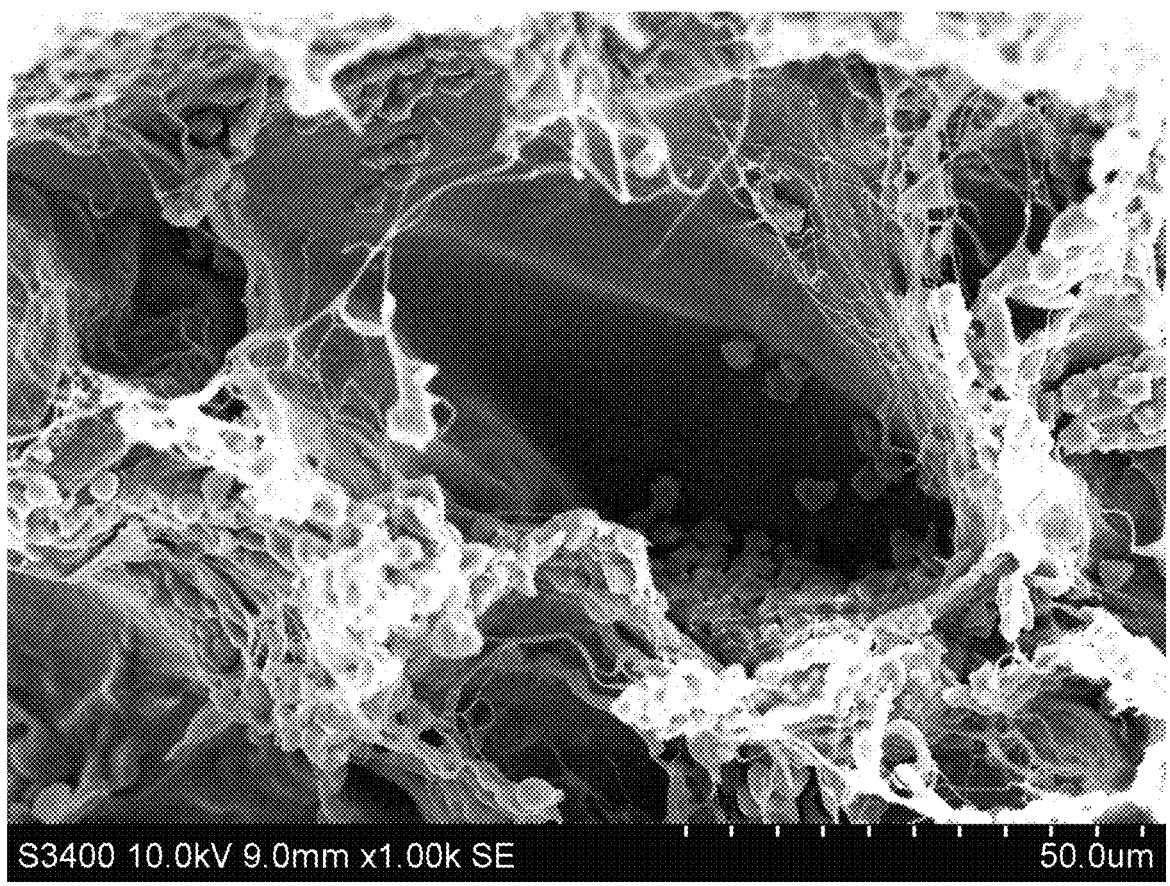
FIG. 7 is an SEM image of a blood clot formed within a pore of an acrylated chitosan/oxidized dextran hydrogel following formation of a hydrogel at a laceration on a porcine liver.

The transparent hydrogel adhered to the tissue and stopped blood flow immediately. The time to hemostasis was found to be 12 seconds. The formation of a clot was later verified using SEM (see, FIG. 7).

d) High Flow, High Pressure Model—Spleen (Laceration)

The spleen was used as a model to evaluate the effect of the acrylated chitosan/oxidized dextran hydrogel on hemostasis as the spleen is a well vascularized organ that can bleed profusely. A scalpel was used to lacerate the spleen, resulting in lacerations that were 30 mm long×16 mm deep. The wound was then blotted with dry gauze to remove excess blood and allow for visibility. The acrylated chitosan/oxidized dextran hydrogel was filled into the wound cavity, as well as applied over the wound surface.

The organ was picked up and observed visually to determine that blood flow had stopped and that hemostasis had been achieved. The time to hemostasis was found to be 82 seconds. The formation of a clot was later verified using SEM (see, FIG. 8).

Figure 8:
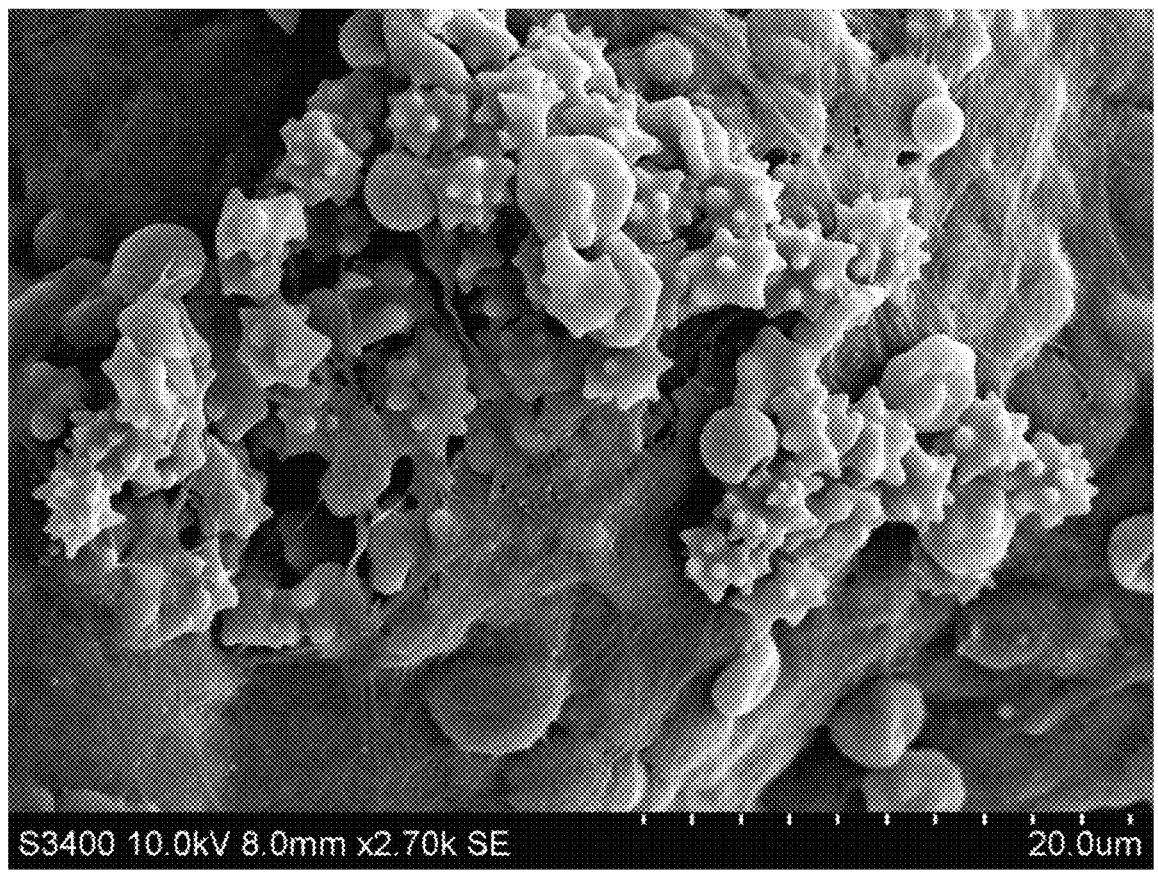
FIG. 8 is an SEM image of a blood clot formed on an acrylated chitosan/oxidized dextran hydrogel following formation of a hydrogel at a laceration on a porcine spleen.

FIG. 8 shows a thick network of fibrin strands trapping multiple activated platelets and red blood cells. Dendritic pseudopodia of multiple platelets was observed, demonstrating platelet activation.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A hemostatic hydrogel composition comprising a gel produced by combining oxidized dextran with an acrylated chitosan composition produced by dissolving chitosan in an acetic acid solution prior to acrylation, the hydrogel composition comprising a burst strength of greater than about 70 mmHg as determined using an ASTM F 2392-04 protocol at about 5 minutes after formation.

2. The hemostatic hydrogel composition of claim 1, wherein the hemostatic hydrogel composition further comprises a total amount of free aldehyde groups of from about 0.1 to about 0.7 moles aldehyde/mole oxidized dextran.

3. The hemostatic hydrogel composition of claim 1, wherein the hemostatic hydrogel composition further comprises a ratio of primary aldehydes in the oxidized dextran to the amines in the acrylated chitosan from about 1.0 to about 2.0, a ratio of total aldehydes in the oxidized dextran to amines in the acrylated chitosan from about 1.5 to about 3.0 or a combination thereof.

4. The hemostatic hydrogel composition of claim 1, wherein the hemostatic hydrogel composition further comprises a ratio of weight-average molecular weight (Mw) of the acrylated chitosan to the oxidized dextran from about 2 to about 10, a ratio of number-average molecular weight (Mn) of the acrylated chitosan to the oxidized dextran from about 4 to about 15, a ratio of z average molecular weight (Mz) of the acrylated chitosan to the oxidized dextran from about 2 to about 10, a ratio of polydispersity index (PDI) (Mw/Mn) of acrylated chitosan to oxidized dextran from about 0.5 to about 0.8, a ratio of PDI (Mz/Mw) of acrylated chitosan to oxidized dextran from about 0.5 to about 1.0, or a combination thereof.

5. The hemostatic hydrogel composition of claim 1, wherein the hemostatic hydrogel composition comprises a bound water content of from about 65% w/w to about 95% w/w.

6. The hemostatic hydrogel composition of claim 1, wherein the hemostatic hydrogel composition comprises a three-dimensional porous structure comprising layers of substantially non-interconnected pores having (a) a pore size distribution from about 10 μm to about 850 μm in diameter, (b) a platelet adhesive surface, or a combination of (a) and (b).

7. The hemostatic hydrogel composition of claim 1, wherein the hemostatic hydrogel composition comprises walls disposed between substantially non-interconnected pores, the walls having a wall thickness of from 0.046 μm to 50 μm.

8. The hemostatic hydrogel composition of claim 1, wherein the hemostatic hydrogel composition comprises a platelet adhesive surface so that, when in contact with blood, the hydrogel composition permits platelets, red blood cells, or a combination thereof within the blood to adhere to the platelet adhesive surface and promote blood clot formation at or within the hydrogel composition.

9. The hemostatic hydrogel composition of claim 1, wherein the hemostatic hydrogel composition comprises a platelet adhesive surface so that, when in contact with blood, the hydrogel composition permits platelet, red blood cells, or a combination thereof within the blood to adhere to the platelet adhesive surface and not permit platelets and/or red blood cells from the blood to enter pores present in a first surface of the hydrogel composition, pass through the hydrogel composition, and then exit the hydrogel composition via pores present in a second surface of the hydrogel composition that opposes the first surface.

10. The hemostatic hydrogel composition of claim 1 further comprising a burst strength of greater than 20 mmHg as determined using an ASTM F 2392-04 protocol at about 10 seconds after formation.

11. The hemostatic hydrogel composition of claim 1 further comprising a burst strength of greater than about 35 mmHg as determined using an ASTM F 2392-04 protocol at about two minutes after formation.

12. The hemostatic hydrogel composition of claim 1 further comprising an elastic modulus of from about 500 Pa to about 5000 Pa at from about 10 seconds to about 80 seconds after the formation of the hydrogel composition.

13. The hemostatic hydrogel composition of claim 1 further comprising a compression modulus of from about 3 kPa to about 250 kPa.

14. The hemostatic hydrogel composition of claim 1 further comprising an average adhesion strength of from about 1.0 N to about 50.0 N, as determined using an ASTM F 2258-05 protocol.

15. The hemostatic hydrogel composition of claim 1 further comprising a volume that does not increase upon exposure to a physiological fluid or body fluid.

16. The hemostatic hydrogel composition of claim 1, wherein the hemostatic hydrogel composition is substantially transparent when the hydrogel composition has a thickness of 2 mm to 10 mm.

17. The hemostatic hydrogel composition of claim 1 further comprising a therapeutic agent, a plurality of stem cells, or a combination thereof.

18. The hemostatic hydrogel composition of claim 1, wherein the hemostatic hydrogel composition has a gelation time from about 10 seconds to about 240 seconds after contacting the acrylated chitosan composition with the oxidized dextran composition.

19. The hemostatic hydrogel composition of claim 1 comprising:
(a) from about 0.00 to about 0.3 mole fraction of a first monomer of formula (I)

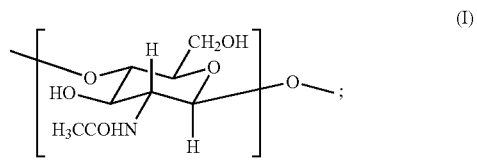

(b) from about 0.02 to about 0.7 mole fraction of a second monomer of formula (III),

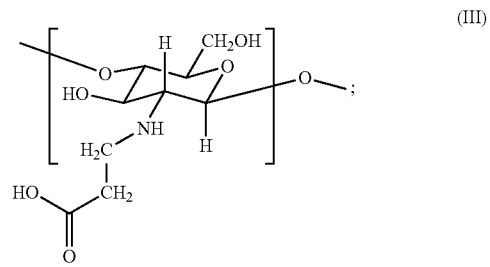

and
(c) from about 0.0 to about 0.8 mole fraction of a third monomer of formula (V),

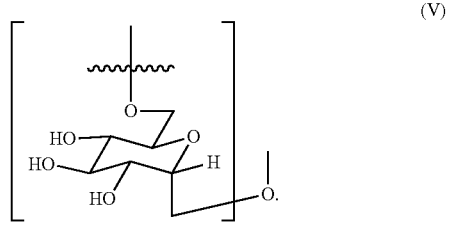

20. The hemostatic hydrogel composition of claim 19, wherein the hemostatic hydrogel composition comprises from about 0.0 to about 0.26 mole fraction of the first monomer of formula (I).

21. The hemostatic hydrogel composition of claim 19, wherein the hemostatic hydrogel composition comprises from about 0.03 to about 0.6 mole fraction of the second monomer of formula (III).

22. The hemostatic hydrogel composition of claim 19, wherein the hemostatic hydrogel composition comprises from about 0.04 to about 0.7 mole fraction of the third monomer of formula (V).

23. The hemostatic hydrogel composition of claim 19, wherein the hemostatic hydrogel composition comprises no greater than about 0.2 mole fraction of a fourth monomer of formula (IV)

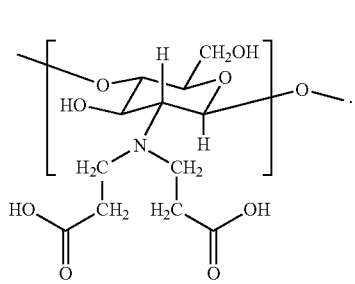

(IV)

24. The hemostatic hydrogel composition of claim 19, wherein the hemostatic hydrogel composition comprises no greater than about 0.65 mole fraction of a fifth monomer of formula (VIII)

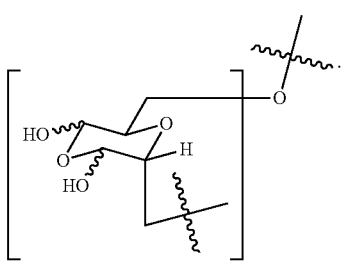

(VIII)

25. The hemostatic hydrogel composition of claim 19, wherein the hydrogel comprises a plurality of crosslinked moieties of formula (IX)

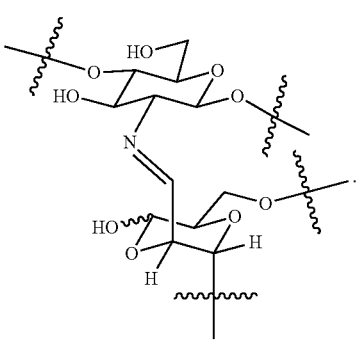

(IX)

26. A method of preparing a hemostatic hydrogel composition of claim 1, the method comprising contacting an acrylated chitosan composition produced by dissolving chitosan in an acetic acid solution prior to acrylation and comprising:
(i) from about 0.01 to about 0.3 mole fraction of a first monomer of formula (I)

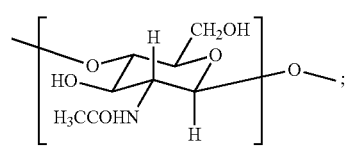

(I)

(ii) from about 0.3 to about 0.75 mole fraction of a second monomer of formula (II)

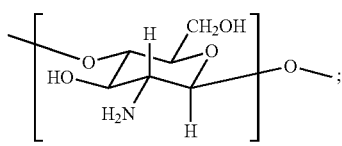

(II)

(iii) from about 0.2 to about 0.7 mole fraction of a third monomer of formula (III)

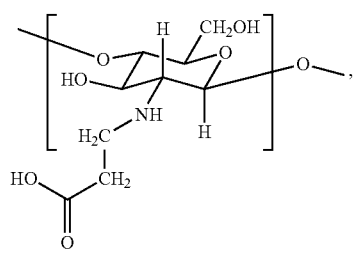

(III)

with an oxidized dextran composition comprising:
(i) less than about 0.8 mole fraction of a first monomer of formula (V)

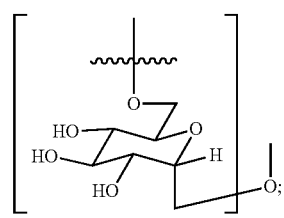

(V)

and
(ii) from about 0.1 to about 1.0 mole fraction of a second monomer, wherein the second monomer is selected from a monomer of formula (VI), a monomer of formula (VII) and a combination of formula (VI) and formula (VII)

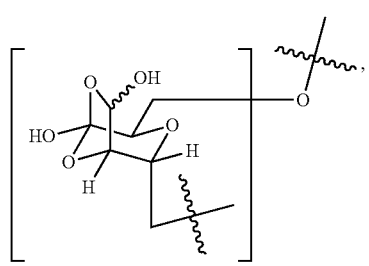

(VI)

-continued

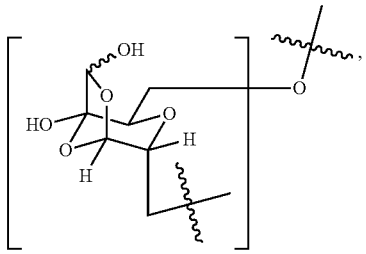
(VII)

thereby to produce the hemostatic hydrogel composition.

27. The method of claim 26, wherein the ratio of the viscosity of the acrylated chitosan composition to the oxidized dextran composition ranges from about 100:1 to about 10,000:1.

28. A method of reducing or stopping blood loss at a location in a subject in need thereof, the method comprising forming at the location in the subject the hemostatic hydrogel composition of claim 1 thereby to reduce or stop blood loss at the location.

29. The method of claim 28, wherein the hemostatic hydrogel composition comprises one or more of the following features:
   (i) the hemostatic hydrogel composition adheres to a tissue surface at the location,
   (ii) platelets, red blood cells, or a combination thereof present at the location adhere to surfaces of pores in the hemostatic hydrogel,
   (iii) the hemostatic hydrogel composition promotes platelet adhesion and collection, platelet activation, and platelet aggregation and concentration at the location,
   (iv) the hemostatic hydrogel composition promotes a blood coagulation cascade to occur at the location, and
   (v) the hemostatic hydrogel promotes blood clot formation at the location.

30. The method of claim 28, wherein the blood loss is caused by trauma, abrasion, or surgical intervention at the location.

31. The method of claim 30, wherein the surgical intervention is cardiac surgery, cranial surgery, spinal surgery, OB-GYN surgery, organ surgery, plastic surgery, a sinus procedure, thoracic surgery, a vascular surgery, a minimally invasive procedure, an arthroscopic procedure, an endoscopic procedure or a laparoscopic procedure.

32. The method of claim 28, wherein the hemostatic hydrogel composition, when formed at the location, is capable of filling a cavity at the location without inducing compression of tissue surrounding the cavity when the hemostatic hydrogel composition is exposed to physiological fluid or a body fluid.

* * * * *